US006444792B1

(12) United States Patent
Gray et al.

(10) Patent No.: US 6,444,792 B1
(45) Date of Patent: Sep. 3, 2002

(54) CTLA4-Cγ4 FUSION PROTEINS

(75) Inventors: Gary S. Gray, Brookline; Jerry Carson, Belmont; Kashi Javaherian, Lexington; Paul D. Rennert, Holliston; Sandra Silver, Boston, all of MA (US)

(73) Assignee: Repligen Corporation, Needham, MA (US)

( * ) Notice: Subject to any disclaimer, the term of this patent is extended or adjusted under 35 U.S.C. 154(b) by 0 days.

(21) Appl. No.: 09/227,595

(22) Filed: Jan. 8, 1999

Related U.S. Application Data

(62) Division of application No. 08/595,590, filed on Feb. 2, 1996.

(51) Int. Cl.⁷ .......................................... A61K 39/395
(52) U.S. Cl. ............................ 530/387.3; 530/387.1; 424/134.1
(58) Field of Search ......................... 530/387.1, 387.3, 530/388.8, 388.85; 424/134.1, 155.1, 157.1

(56) References Cited

U.S. PATENT DOCUMENTS

| | | | |
|---|---|---|---|
| 5,116,964 A | | 5/1992 | Capon et al. |
| 5,428,130 A | | 6/1995 | Capon et al. |
| 5,434,131 A | | 7/1995 | Linsley et al. |
| 5,958,403 A | * | 9/1999 | Strom et al. |

FOREIGN PATENT DOCUMENTS

| | | |
|---|---|---|
| EP | 96305298 | 7/1996 |
| WO | WO 93/00431 | 1/1993 |
| WO | WO 95/33770 | 12/1995 |
| WO | WO 96/31229 | 10/1996 |

OTHER PUBLICATIONS

Lazar et al., Molecular and Cellular Biology 8:1247–1252, 1988.*
Lin et al., Biochemistry 14:1559–1563, 1975.*
Burgess et al., The Journal of Cell Biology 111:2129–2138, 1990.*
Schwartz et al., Proc. Natl. Acad. Sci. USA 84:6408–6411, 1987.*
Baliga, P., et al., "CTLA4Ig Prolongs Allograft Survival While Suppressing Cell–Mediated Immunity," *Transplantation*, vol. 58, No. 10, 1082–1090 (1994).
Bolling, S., et al., "Inhibition of B7–Induced CD28 T–cell Activation with CTLA4Ig Prevents Cardiac Allograft Rejection: Evidence for Costimulation," *Transplantation*, vol. 43, 413–415 (1992).
Canfield, S. and Morrison, S., "The Binding Affinity of Human IgG for its High Affinity Fc Receptor is Determined by Multiple Amino Acids in the CH 2 Domain and is Modulated by the Hinge Region," *J. Exp. Med.*, vol. 173, 1483–1491 (1991).
Duncan, A. and Winter, G., "The Binding Site for C1q on IgG," *Nature*, vol. 332, 738–740 (1988).

Finck, Barbara, et al. "Treament of Murine Lupus with CTLA4Ig", *Science*, vol. 265, pp. 1225–1227, Aug. 26 (1994).
Gillies et al., "Antigen binding and biological activities of engineered mutant chimeric antibodies with human tumor specificities," *Hum. Antibodies Hybridomas.*, 1(1):47–54 (1990).
Hakim, Frances, et al. "Acute Graft–Versus–Host Reaction Can Be Aborted by Blockade of Costimulatory Molecules", *The Journal of Immunology*, vol. 155, No. 4, Aug. 15, (1995).
Lenschow, D., et al., "Long–term Survival of Xenogeneic Pancreatic Islet Grafts Induced by CTLA4Ig," *Science*, vol. 257, 789–792 (1992).
Lin, H., et al., "Long–term Acceptance of Major Histocompatibility Complex Mismatched Cardiac Allografts Induced by CTLA4Ig Plus Donor–specific Transfusion," *J. Exp. Med.*, vol. 178, 1801–1806 (1993).
Lund, J., et al., "Human FcγRI and FcγRII Interact with Distinct but Overlapping Sites on Human IgG," *The Journal of Immunology*, vol. 147, No. 8, 2657–2662 (1991).
Pearson, T., et al., "Transplantation Tolerance Induced by CTLA4–Ig," *Transplantation*, vol. 57, No. 12, 1701–1706 (1994).
Steurer, Wolfgang et al. "EX Vivo Coating of Islet Cell Allografts with Murine CTLA4/Fc Promotes Graft Tolerance", *The Journal of Immunology*, vol. 155, No. 3, Aug. 1, (1995); p. 1165–1174.
Tan, L., et al., "Influence of the Hinge Region on Complement Activation, C1q Binding, and Segmental Flexibility in Chimeric Human Immunoglobulins," *Proc. Natl. Acad. Sci. USA*, vol. 87, 162–166 (1990).

* cited by examiner

Primary Examiner—Sheela Huff
Assistant Examiner—Larry R. Helms
(74) Attorney, Agent, or Firm—Lahive & Cockfiled, LLP; Amy E. Mandragouras, Esq.; Megan E. Williams, Esq.

(57) ABSTRACT

CTLA4-immunoglobulin fusion proteins having modified immunoglobulin constant region-mediated effector functions, and nucleic acids encoding the fusion proteins, are described. The CTLA4-immunoglobulin fusion proteins comprise two components: a first peptide having a CTLA4 activity and a second peptide comprising an immunoglobulin constant region which is modified to reduce at least one constant region-mediated biological effector function relative to a CTLA4-IgG1 fusion protein. The nucleic acids of the invention can be integrated into various expression vectors, which in turn can direct the synthesis of the corresponding proteins in a variety of hosts, particularly eukaryotic cells. The CTLA4-immunoglobulin fusion proteins described herein can be administered to a subject to inhibit an interaction between a CTLA4 ligand (e.g., B7-1 and/or B7-2) on an antigen presenting cell and a receptor for the CTLA4 ligand (e.g., CD28 and/or CTLA4) on the surface of T cells to thereby suppress an immune response in the subject, for example to inhibit transplantation rejection, graft versus host disease or autoimmune responses.

1 Claim, 8 Drawing Sheets

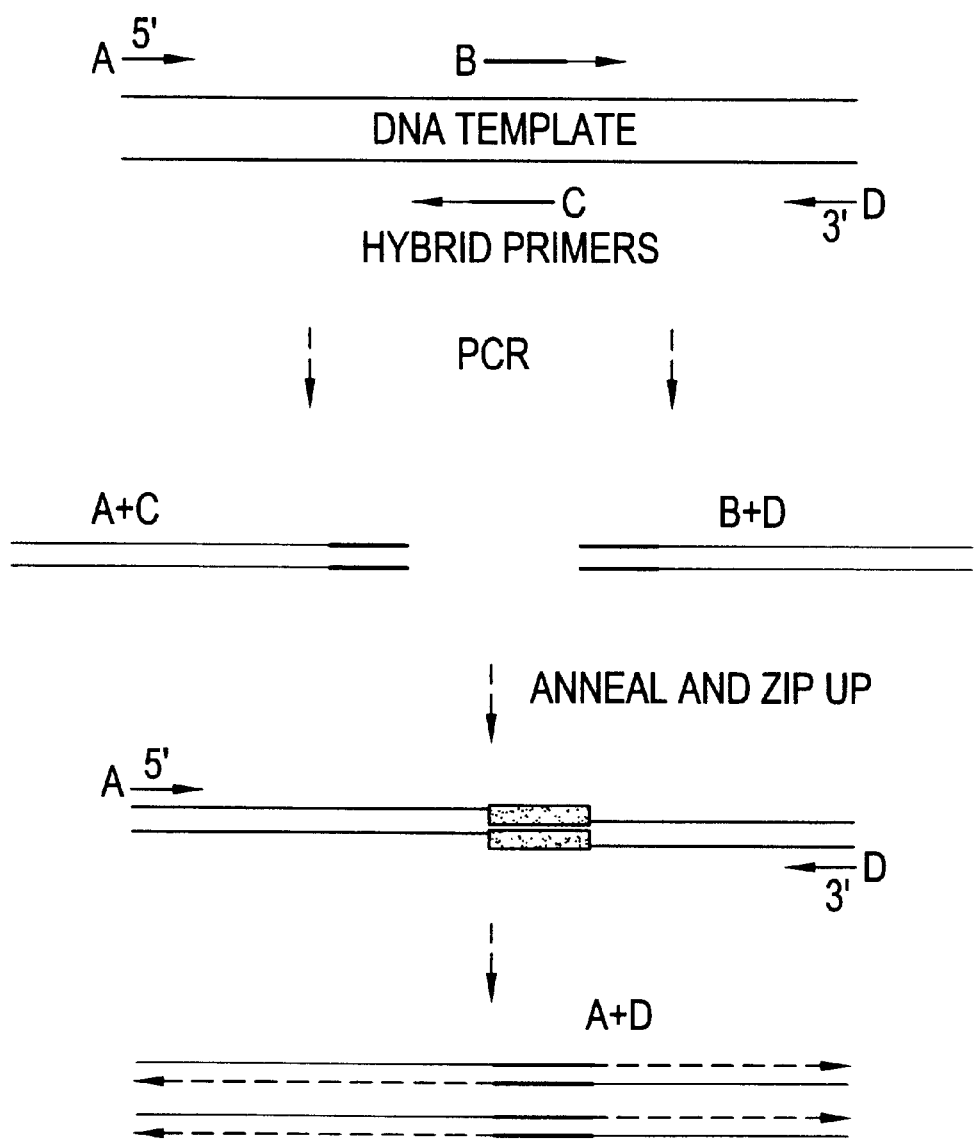

FIG. 2A

Gamma 1:

```
hinge........................................Ch2...................
Native   A E P K S C D K T H T C P P C P.......A P E L L G G P S......
                                                      234 235  237
Mutated  A E P K S S D K T H T S P P S P.......A P E A E G A P S......
                 _           _   _             234 235  237
                                                  _ _   _
```

FIG. 2B

Gamma 4:

```
hinge........................................Ch2...................
Native   A E S K Y G P P C P S C P.............A P E F L G G P S......
                                                      234 235  237
Mutated  A E S K Y G P P S P S S P.............A P E F G G A P S......
                         _   _ _               234 235  237
                                                        _   _
```

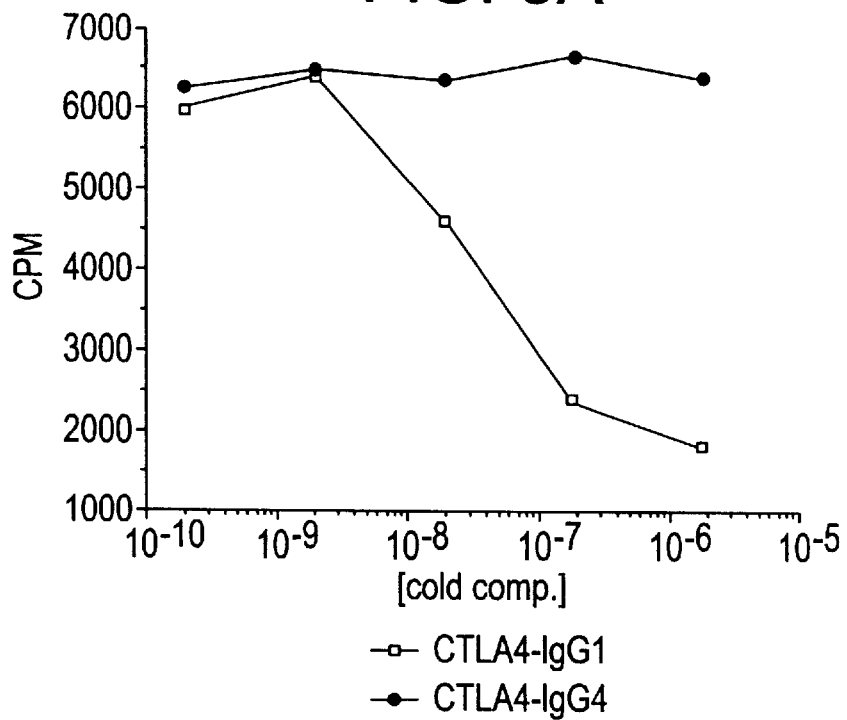
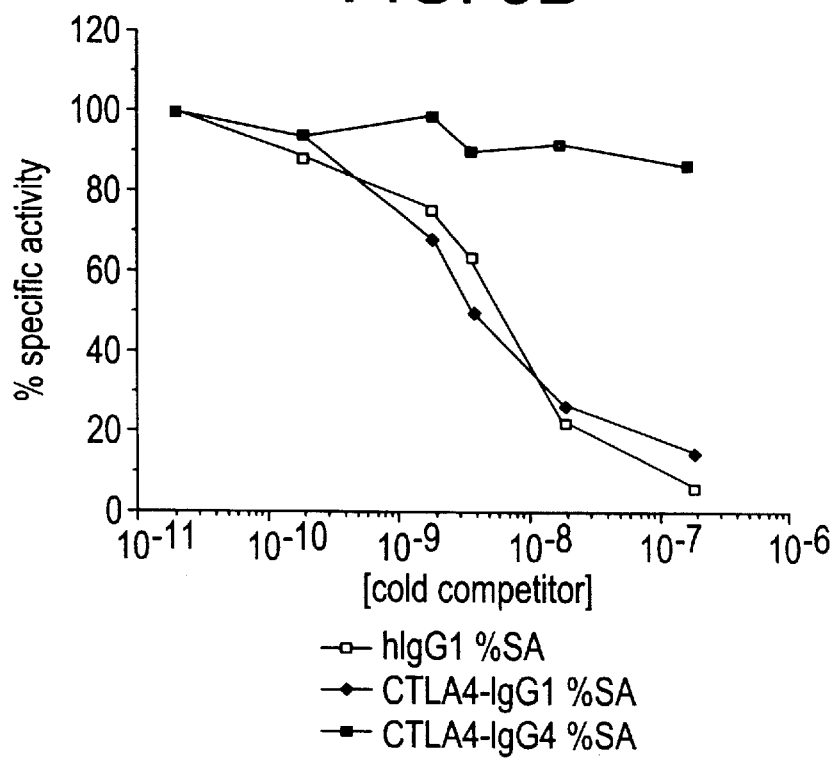

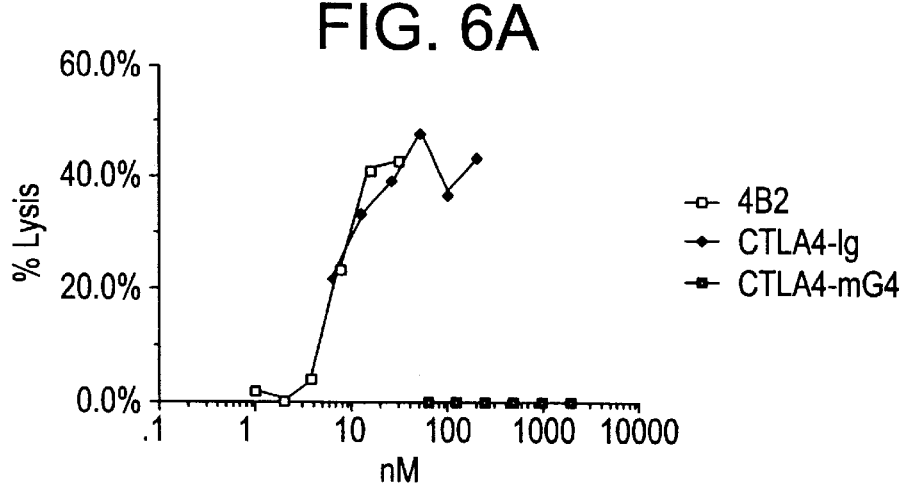
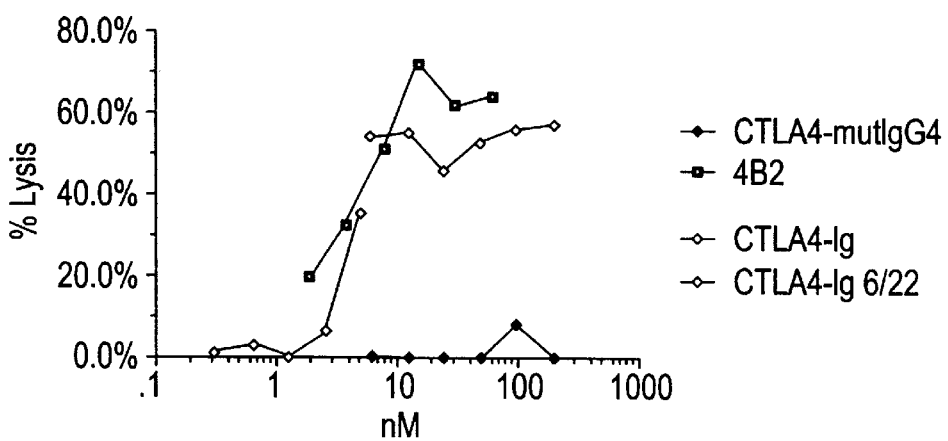
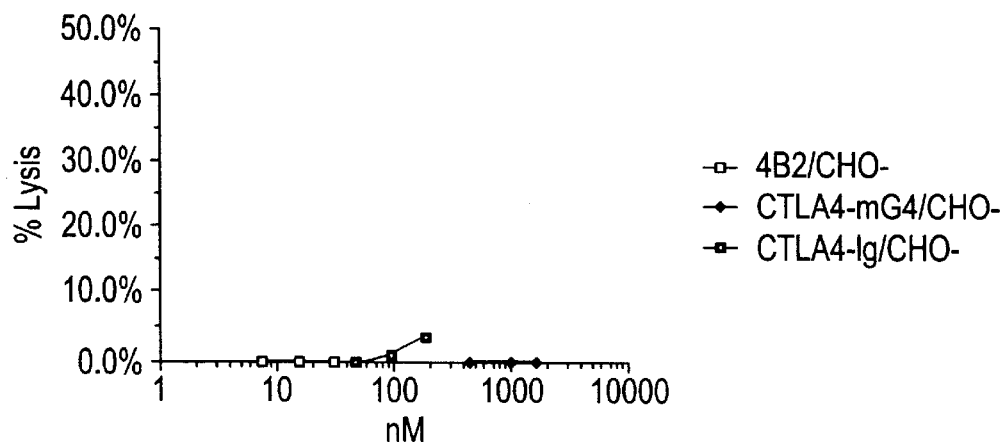

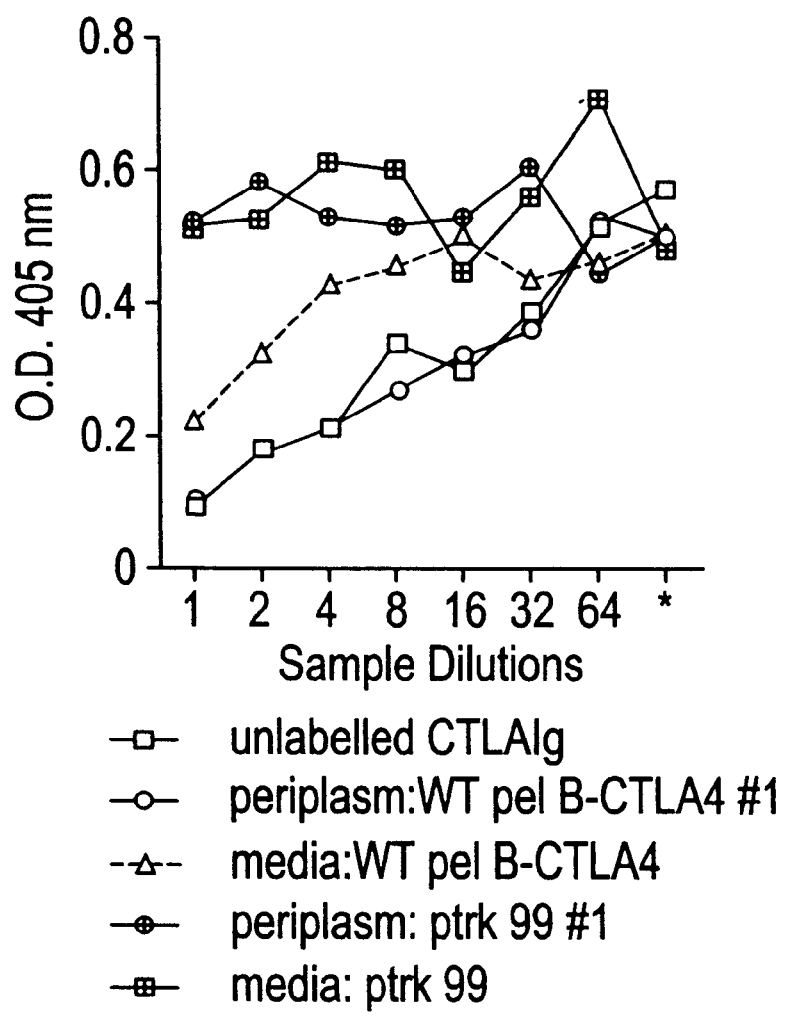

SEQUENCE LISTING (1) GENERAL INFORMATION:

(iii) NUMBER OF SEQUENCES: 32

(2) INFORMATION FOR SEQ ID NO:1:

(i) SEQUENCE CHARACTERISTICS:
       (A) LENGTH: 43 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:1:

CATTCTAGAA CCTCGACAAG CTTGAGATCA CAGTTCTCTC TAC                43

(2) INFORMATION FOR SEQ ID NO:2:

(i) SEQUENCE CHARACTERISTICS:
       (A) LENGTH: 46 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:2:

CAGCAGGCTG GGCCACGTGC ATTGCGGAGT GGACACCTGT GGAGAG            46

(2) INFORMATION FOR SEQ ID NO:3:

(i) SEQUENCE CHARACTERISTICS:
       (A) LENGTH: 46 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:3:

CTCTCCACAG GTGTCCACTC CGCAATGCAC GTGGCCCAGC CTGCTG            46

(2) INFORMATION FOR SEQ ID NO:4:

(i) SEQUENCE CHARACTERISTICS:
       (A) LENGTH: 46 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:4:

TGTGTGTGGA ATTCTCATTA CTGATCAGAA TCTGGGCACG GTTCTG            46

(2) INFORMATION FOR SEQ ID NO:5:

(i) SEQUENCE CHARACTERISTICS:
       (A) LENGTH: 78 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:5:

GCATTTTAAG CTTTTTCCTG ATCAGGAGCC CAAATCTTCT GACAAAACTC ACACATCTCC    60

ACCGTCTCCA GGTAAGCC    78

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

TAATACGACT CACTATAGGG    20

(2) INFORMATION FOR SEQ ID NO:7:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

GAGCATTTTC CTGATCAGGA GTCCAAATAT GGTCCCCCAC CCCATCATCC CCAGGTAAGC    60

CAACCC    66

(2) INFORMATION FOR SEQ ID NO:8:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

GCAGAGGAAT TCGAGCTCGG TACCCGGGGA TCCCCAGTGT GGGGACAGTG GGACCCGCTC    60

TGCCTCCC    68

(2) INFORMATION FOR SEQ ID NO:9:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

GGGTTTTGGG GGGAAGAGGA AGACTGACGG TGCCCCCTCG GCTTCAGGTG CTGAGGAAG    59

(2) INFORMATION FOR SEQ ID NO:10:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

CATCTCTTCC TCAGCACCTG AAGCCGAGGG GGCACCGTCA GTCTTCCTCT TCCCCC            56

(2) INFORMATION FOR SEQ ID NO:11:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

CGCACGTGAC CTCAGGGGTC CGGGAGATCA TGAGAGTGTC CTTGGGTTTT GGGGGGAACA            60

GGAAGACTGA TGGTGCCCCC TCGAACTCAG GTGCTGAGG                                  99

(2) INFORMATION FOR SEQ ID NO:12:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

CCTCAGCACC TGAGTTCGAG GGGGCACCAT CAGTCTTCCT GTTCCCCCA AAACCCAAGG            60

ACACTCTCAT GATCTCCCGG ACCCCTGAGG TCACGTGCG                                  99

(2) INFORMATION FOR SEQ ID NO:13:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

CATTCGCTTA CCTCGACAAG CTTGAGATCA CAGTTCTCTC TAC                             43

(2) INFORMATION FOR SEQ ID NO:14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

GGAGTGGACA CCTGTGGAGA G                                                    21

(2) INFORMATION FOR SEQ ID NO:15:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

CTCCACAGGT GTCCACTCCG CAATGCACGT GGCCCAGCC                              39

(2) INFORMATION FOR SEQ ID NO:16:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

GAGGTTGTAA GGACTCACCT GAAATCTGGG CTCCGTTGC                              39

(2) INFORMATION FOR SEQ ID NO:17:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

GCAACGGAGC CCAGATTTCA GGTGAGTCCT TACAACCTC                              39

(2) INFORMATION FOR SEQ ID NO:18:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

GGCTAGATAT CTCTAGACTA TAAATCTCTG GCCATGAAG                              39

(2) INFORMATION FOR SEQ ID NO:19:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

GGCACTAGGT CGACTCTAGA AACTGAGGAA GCAAAGTTTA AATTCTACTC ACGTTTAATC       60

TGGGCTCCGT TGC                                                          73

(2) INFORMATION FOR SEQ ID NO:20:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

-continued

```
GCAGAGAGAC ATATGGCAAT GCACGTGGCC CAGCCTGCTG TGG                 43
```

(2) INFORMATION FOR SEQ ID NO:21:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

```
GCAGAGAGAG GATCCTCAGT CAGTTAGTCA GAATCTGGGC ACGGTTCTGG          50
```

(2) INFORMATION FOR SEQ ID NO:22:

(i) SEQUENCE CHARACTERISTICS:
        (A) LENGTH: 107 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

```
GGCACTAGTC ATGAAATACC TATTGCCTAC GGCAGCCGCT GGATTGTTAT TACTCGCTGC  60
CCAACCAGCG ATGGCCGCAG CAATGCACGT GGCCCAGCCT GCTGTGG              107
```

(2) INFORMATION FOR SEQ ID NO:23:

(i) SEQUENCE CHARACTERISTICS:
        (A) LENGTH: 1705 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

```
CATTCGCTTA CCTCGAGAAG CTTGAGATCA CAGTTCTCTC TACAGTTACT GAGCACACAG   60
GACCTCACCA TGGGATGGAG CTGTATCATC CTCTTCTTGG TAGCAACAGC TACAGGTAAG  120
GGGCTCACAG TAGCAGGCTT GAGGTCTGGA CATATATATG GGTGACAATG ACATCCACTT  180
TGCCTTTCTC TCCACAGGTG TCCACTCCGC AATGCACGTG GCCCAGCCTG CTGTGGTACT  240
GGCCAGCAGC CGAGGCATCG CCAGCTTTGT GTGTGAGTAT GCATCTCCAG GCAAAGCCAC  300
TGAGGTCCGG GTGACAGTGC TTCGGCAGGC TGACAGCCAG GTGACTGAAG TCTGTGCGGC  360
AACCTACATG ATGGGGAATG AGTTGACCTT CCTAGATGAT TCCATCTGCA CGGGCACCTC  420
CAGTGGAAAT CAAGTGAACC TCACTATCCA AGGACTGAGG GCCATGGACA CGGGACTCTA  480
CATCTGCAAG GTGGAGCTCA TGTACCCACC GCCATACTAC CTGGGCATAG CAACGGAAC   540
CCAGATTTAT GTAATTGATC CAGAACCGTG CCCAGATTCT GATCAGGAGC CAAATCTTC   600
TGACAAAACT CACACATCTC CACCGTCTCC AGGTAAGCCA GCCCAGGCCT CGCCCTCCAG  660
CTCAAGGCGG GACAGGTGCC CTAGAGTAGC CTGCATCCAG GGACAGGCCC CAGCCGGGTG  720
CTGACACGTC CACCTCCATC TCTTCCTCAG CACCTGAAGC CGAGGGGCA CCGTCAGTCT   780
TCCTCTTCCC CCCAAAACCC AAGGACACCC TCATGATCTC CCGGACCCCT GAGGTCACAT  840
GCGTGGTGGT GGACGTGAGC CACGAAGACC CTGAGGTCAA GTTCAACTGG TACGTGGACG  900
GCGTGGAGGT GCATAATGCC AAGACAAAGC CGCGGGAGGA GCAGTACAAC AGCACGTACC  960
```

-continued

```
GGGTGGTCAG CGTCCTCACC GTCCTGCACC AGGACTGGCT GAATGGCAAG GAGTACAAGT    1020

GCAAGGTCTC CAACAAAGCC CTCCCAGCCC CCATCGAGAA AACCATCTCC AAAGCCAAAG    1080

GTGGGACCCG TGGGGTGCGA GGGCCACATG GACAGAGGCC GGCTCGGCCC ACCCTCTGCC    1140

CTGAGAGTGA CCGCTGTACC AACCTCTGTC CTACAGGGCA GCCCCGAGAA CCACAGGTGT    1200

ACACCCTGCC CCCATCCCGG GATGAGCTGA CCAAGAACCA GGTCAGCCTG ACCTGCCTGG    1260

TCAAAGGCTT CTATCCCAGC GACATCGCCG TGGAGTGGGA GAGCAATGGG CAGCCGGAGA    1320

ACAACTACAA GACCACGCCT CCCGTGCTGG ACTCCGACGG CTCCTTCTTC CTCTACAGCA    1380

AGCTCACCGT GGACAAGAGC AGGTGGCAGC AGGGGAACGT CTTCTCATGC TCCGTGATGC    1440

ATGAGGCTCT GCACAACCAC TACACGCAGA AGAGCCTCTC CCTGTCTCCG GGTAAATGAG    1500

TGCGACGGCC GGCAAGCCCC GCTCCCCGGG CTCTCGCGGT CGCACGAGGA TGCTTGGCAC    1560

GTACCCCCTG TACATACTTC CCGGGCGCCC AGCATGGAAA TAAAGCACCC AGCGCTGCCC    1620

TGGGCCCCTG CGAGACTGTG ATGGTTCTTT CCACGGGTCA GGCCGAGTCT GAGGCCTGAG    1680

TGGCATGAGG GAGGCAGAGC GGGTC                                         1705
```

(2) INFORMATION FOR SEQ ID NO:24:

(i) SEQUENCE CHARACTERISTICS:
        (A) LENGTH: 377 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:24:

```
Met Gly Trp Ser Cys Ile Ile Leu Phe Leu Val Ala Thr Ala Thr Gly
 1               5                  10                  15

Val His Ser Ala Met His Val Ala Gln Pro Ala Val Val Leu Ala Ser
            20                  25                  30

Ser Arg Gly Ile Ala Ser Phe Val Cys Glu Tyr Ala Ser Pro Gly Lys
        35                  40                  45

Ala Thr Glu Val Arg Val Thr Val Leu Arg Gln Ala Asp Ser Gln Val
    50                  55                  60

Thr Glu Val Cys Ala Ala Thr Tyr Met Met Gly Asn Glu Leu Thr Phe
65                  70                  75                  80

Leu Asp Asp Ser Ile Cys Thr Gly Thr Ser Ser Gly Asn Gln Val Asn
                85                  90                  95

Leu Thr Ile Gln Gly Leu Arg Ala Met Asp Thr Gly Leu Tyr Ile Cys
            100                 105                 110

Lys Val Glu Leu Met Tyr Pro Pro Pro Tyr Tyr Leu Gly Ile Gly Asn
        115                 120                 125

Gly Thr Gln Ile Tyr Val Ile Asp Pro Glu Pro Cys Pro Asp Ser Asp
    130                 135                 140

Gln Glu Pro Lys Ser Ser Asp Lys Thr His Thr Ser Pro Pro Ser Pro
145                 150                 155                 160

Ala Pro Glu Ala Glu Gly Ala Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Lys Phe Asn Trp Tyr
        195                 200                 205
```

```
Val Asp Gly Val Glu Val His Asn Ala Lys Thr Lys Pro Arg Glu Glu
    210                 215                 220
Gln Tyr Asn Ser Thr Tyr Arg Val Val Ser Val Leu Thr Val Leu His
225                 230                 235                 240
Gln Asp Trp Leu Asn Gly Lys Glu Tyr Lys Cys Lys Val Ser Asn Lys
                245                 250                 255
Ala Leu Pro Ala Pro Ile Glu Lys Thr Ile Ser Lys Ala Lys Gly Gln
            260                 265                 270
Pro Arg Glu Pro Gln Val Tyr Thr Leu Pro Pro Ser Arg Asp Glu Leu
        275                 280                 285
Thr Lys Asn Gln Val Ser Leu Thr Cys Leu Val Lys Gly Phe Tyr Pro
    290                 295                 300
Ser Asp Ile Ala Val Glu Trp Glu Ser Asn Gly Gln Pro Glu Asn Asn
305                 310                 315                 320
Tyr Lys Thr Thr Pro Pro Val Leu Asp Ser Asp Gly Ser Phe Phe Leu
                325                 330                 335
Tyr Ser Lys Leu Thr Val Asp Lys Ser Arg Trp Gln Gln Gly Asn Val
            340                 345                 350
Phe Ser Cys Ser Val Met His Glu Ala Leu His Asn His Tyr Thr Gln
        355                 360                 365
Lys Ser Leu Ser Leu Ser Pro Gly Lys
    370                 375
```

(2) INFORMATION FOR SEQ ID NO:25:

(i) SEQUENCE CHARACTERISTICS:
        (A) LENGTH: 1747 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

```
CATTCGCTTA CCTCGAGAAG CTTGAGATCA CAGTTCTCTC TACAGTTACT GAGCACACAG     60
GACCTCACCA TGGGATGGAG CTGTATCATC CTCTTCTTGG TAGCAACAGC TACAGGTAAG    120
GGGCTCACAG TAGCAGGCTT GAGGTCTGGA CATATATATG GGTGACAATG ACATCCACTT    180
TGCCTTTCTC TCCACAGGTG TCCACTCCGC AATGCACGTG GCCCAGCCTG CTGTGGTACT    240
GGCCAGCAGC CGAGGCATCG CCAGCTTTGT GTGTGAGTAT GCATCTCCAG GCAAAGCCAC    300
TGAGGTCCGG GTGACAGTGC TTCGGCAGGC TGACAGCCAG GTGACTGAAG TCTGTGCGGC    360
AACCTACATG ATGGGGAATG AGTTGACCTT CCTAGATGAT TCCATCTGCA CGGGCACCTC    420
CAGTGGAAAT CAAGTGAACC TCACTATCCA AGGACTGAGG GCCATGGACA CGGGACTCTA    480
CATCTGCAAG GTGGAGCTCA TGTACCCACC GCCATACTAC CTGGGCATAG GCAACGGAAC    540
CCAGATTTAT GTAATTGATC CAGAACCGTG CCCAGATTCT GATCAGGAGT CCAAATATGG    600
TCCCCCATCC CCATCATCCC CAGGTAAGCC AACCCAGGCC TCGCCCTCCA GCTCAAGGCG    660
GGACAGGTGC CCTAGAGTAG CCTGCATCCA GGGACAGGCC CCAGCCGGGT GCTGACGCAT    720
CCACCTCCAT CTCTTCCTCA GCACCTGAGT TCCTGGGGGG ACCATCAGTC TTCCTGTTCC    780
CCCCAAAACC CAAGGACACT CTCATGATCT CCCGGACCCC TGAGGTCACG TGCGTGGTGG    840
TGGACGTGAG CCAGGAAGAC CCCGAGGTCC AGTTCAACTG GTACGTGGAT GGCGTGGAGG    900
TGCATAATGC CAAGACAAAG CCGCGGGAGG AGCAGTTCAA CAGCACGTAC CGTGTGGTCA    960
```

-continued

```
GCGTCCTCAC CGTCCTGCAC CAGGACTGGC TGAACGGCAA GGAGTACAAG TGCAAGGTCT   1020

CCAACAAAGG CCTCCCGTCC TCCATCGAGA AAACCATCTC CAAAGCCAAA GGTGGGACCC   1080

ACGGGGTGCG AGGGCCACAC GGACAGAGGC CAGCTCGGCC CACCCTCTGC CCTGGGAGTG   1140

ACCGCTGTGC CAACCTCTGT CCCTACAGGG CAGCCCCGAG AGCCACAGGT GTACACCCTG   1200

CCCCCATCCC AGGAGGAGAT GACCAAGAAC CAGGTCAGCC TGACCTGCCT GGTCAAAGGC   1260

TTCTACCCCA GCGACATCGC CGTGGAGTGG GAGAGCAATG GGCAGCCGGA GAACAACTAC   1320

AAGACCACGC CTCCCGTGCT GGACTCCGAC GGCTCCTTCT TCCTCTACAG CAGGCTAACC   1380

GTGGACAAGA GCAGGTGGCA GGAGGGGAAT GTCTTCTCAT GCTCCGTGAT GCATGAGGCT   1440

CTGCACAACC ACTACACACA GAAGAGCCTC TCCCTGTCTC TGGGTAAATG AGTGCCAGGG   1500

CCGGCAAGCC CCCGCTCCCC GGGCTCTCGG GGTCGCGCGA GGATGCTTGG CACGTACCCC   1560

GTCTACATAC TTCCCAGGCA CCCAGCATGG AAATAAAGCA CCCACCACTG CCCTGGGCCC   1620

CTGTGAGACT GTGATGGTTC TTTCCACGGG TCAGGCCGAG TCTGAGGCCT GAGTGACATG   1680

AGGGAGGCAG AGCGGTCCCA CTGTCCCCAC ACTGGGGATC CCCGGGTACC GAGCTCGATT   1740

CCTCTGC                                                            1747
```

(2) INFORMATION FOR SEQ ID NO:26:

(i) SEQUENCE CHARACTERISTICS:
        (A) LENGTH: 374 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:26:

```
Met Gly Trp Ser Cys Ile Ile Leu Phe Leu Val Ala Thr Ala Thr Gly
1               5                   10                  15

Val His Ser Ala Met His Val Ala Gln Pro Ala Val Val Leu Ala Ser
            20                  25                  30

Ser Arg Gly Ile Ala Ser Phe Val Cys Glu Tyr Ala Ser Pro Gly Lys
        35                  40                  45

Ala Thr Glu Val Arg Val Thr Val Leu Arg Gln Ala Asp Ser Gln Val
    50                  55                  60

Thr Glu Val Cys Ala Ala Thr Tyr Met Met Gly Asn Glu Leu Thr Phe
65                  70                  75                  80

Leu Asp Asp Ser Ile Cys Thr Gly Thr Ser Ser Gly Asn Gln Val Asn
                85                  90                  95

Leu Thr Ile Gln Gly Leu Arg Ala Met Asp Thr Gly Leu Tyr Ile Cys
            100                 105                 110

Lys Val Glu Leu Met Tyr Pro Pro Pro Tyr Tyr Leu Gly Ile Gly Asn
        115                 120                 125

Gly Thr Gln Ile Tyr Val Ile Asp Pro Glu Pro Cys Pro Asp Ser Asp
    130                 135                 140

Gln Glu Ser Lys Tyr Gly Pro Pro Ser Pro Ser Pro Ala Pro Glu
145                 150                 155                 160

Phe Glu Gly Ala Pro Ser Val Phe Leu Phe Pro Lys Pro Lys Asp
                165                 170                 175

Thr Leu Met Ile Ser Arg Thr Pro Glu Val Thr Cys Val Val Val Asp
            180                 185                 190

Val Ser Gln Glu Asp Pro Glu Val Gln Phe Asn Trp Tyr Val Asp Gly
```

```
            195                 200                 205
Val Glu Val His Asn Ala Lys Thr Lys Pro Arg Glu Glu Gln Phe Asn
    210                 215                 220
Ser Thr Tyr Arg Val Val Ser Val Leu Thr Val Leu His Gln Asp Trp
225                 230                 235                 240
Leu Asn Gly Lys Glu Tyr Lys Cys Lys Val Ser Asn Lys Gly Leu Pro
                245                 250                 255
Ser Ser Ile Glu Lys Thr Ile Ser Lys Ala Lys Gly Gln Pro Arg Glu
                260                 265                 270
Pro Gln Val Tyr Thr Leu Pro Pro Ser Gln Glu Glu Met Thr Lys Asn
            275                 280                 285
Gln Val Ser Leu Thr Cys Leu Val Lys Gly Phe Tyr Pro Ser Asp Ile
            290                 295                 300
Ala Val Glu Trp Glu Ser Asn Gly Gln Pro Glu Asn Asn Tyr Lys Thr
305                 310                 315                 320
Thr Pro Pro Val Leu Asp Ser Asp Gly Ser Phe Phe Leu Tyr Ser Arg
                325                 330                 335
Leu Thr Val Asp Lys Ser Arg Trp Gln Glu Gly Asn Val Phe Ser Cys
                340                 345                 350
Ser Val Met His Glu Ala Leu His Asn His Tyr Thr Gln Lys Ser Leu
            355                 360                 365
Ser Leu Ser Leu Gly Lys
    370
```

(2) INFORMATION FOR SEQ ID NO:27:

(i) SEQUENCE CHARACTERISTICS:
        (A) LENGTH: 1747 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

```
CATTCGCTTA CCTCGAGAAG CTTGAGATCA CAGTTCTCTC TACAGTTACT GAGCACACAG    60
GACCTCACCA TGGATGGAG CTGTATCATC CTCTTCTTGG TAGCAACAGC TACAGGTAAG    120
GGGCTCACAG TAGCAGGCTT GAGGTCTGGA CATATATATG GGTGACAATG ACATCCACTT   180
TGCCTTTCTC TCCACAGGTG TCCACTCCGC AATGCACGTG GCCCAGCCTG CTGTGGTACT   240
GGCCAGCAGC CGAGGCATCG CCAGCTTTGT GTGTGAGTAT GCATCTCCAG GCAAAGCCAC   300
TGAGGTCCGG GTGACAGTGC TTCGGCAGGC TGACAGCCAG GTGACTGAAG TCTGTGCGGC   360
AACCTACATG ATGGGGAATG AGTTGACCTT CCTAGATGAT TCCATCTGCA CGGGCACCTC   420
CAGTGGAAAT CAAGTGAACC TCACTATCCA AGGACTGAGG GCCATGGACA CGGGACTCTA   480
CATCTGCAAG GTGGAGCTCA TGTACCCACC GCCATACTAC CTGGGCATAG CAACGGAAC   540
CCAGATTTAT GTAATTGATC CAGAACCGTG CCCAGATTCT GATCAGGAGT CCAAATATGG   600
TCCCCCATCC CCATCATCCC CAGGTAAGCC AACCCAGGCC TCGCCCTCCA GCTCAAGGCG   660
GGACAGGTGC CCTAGAGTAG CCTGCATCCA GGGACAGGCC CCAGCCGGGT GCTGACGCAT   720
CCACCTCCAT CTCTTCCTCA GCACCTGAGT TCGAGGGGC ACCATCAGTC TTCCTGTTCC   780
CCCCAAAACC CAAGGACACT CTCATGATCT CCCGGACCCC TGAGGTCACG TGCGTGGTGG   840
TGGACGTGAG CCAGGAAGAC CCCGAGGTCC AGTTCAACTG GTACGTGGAT GGCGTGGAGG   900
TGCATAATGC CAAGACAAAG CCGCGGGAGG AGCAGTTCAA CAGCACGTAC CGTGTGGTCA   960
```

```
GCGTCCTCAC CGTCCTGCAC CAGGACTGGC TGAACGGCAA GGAGTACAAG TGCAAGGTCT    1020

CCAACAAAGG CCTCCCGTCC TCCATCGAGA AAACCATCTC CAAAGCCAAA GGTGGGACCC    1080

ACGGGGTGCG AGGGCCACAC GGACAGAGGC CAGCTCGGCC CACCCTCTGC CCTGGGAGTG    1140

ACCGCTGTGC CAACCTCTGT CCCTACAGGG CAGCCCCGAG AGCCACAGGT GTACACCCTG    1200

CCCCCATCCC AGGAGGAGAT GACCAAGAAC CAGGTCAGCC TGACCTGCCT GGTCAAAGGC    1260

TTCTACCCCA GCGACATCGC CGTGGAGTGG GAGAGCAATG GGCAGCCGGA GAACAACTAC    1320

AAGACCACGC CTCCCGTGCT GGACTCCGAC GGCTCCTTCT TCCTCTACAG CAGGCTAACC    1380

GTGGACAAGA GCAGGTGGCA GGAGGGGAAT GTCTTCTCAT GCTCCGTGAT GCATGAGGCT    1440

CTGCACAACC ACTACACACA GAAGAGCCTC TCCCTGTCTC TGGGTAAATG AGTGCCAGGG    1500

CCGGCAAGCC CCCGCTCCCC GGGCTCTCGG GGTCGCGCGA GGATGCTTGG CACGTACCCC    1560

GTCTACATAC TTCCCAGGCA CCCAGCATGG AAATAAAGCA CCCACCACTG CCCTGGGCCC    1620

CTGTGAGACT GTGATGGTTC TTTCCACGGG TCAGGCCGAG TCTGAGGCCT GAGTGACATG    1680

AGGGAGGCAG AGCGGTCCCA CTGTCCCCAC ACTGGGGATC CCCGGGTACC GAGCTCGATT    1740

CCTCTGC                                                             1747
```

(2) INFORMATION FOR SEQ ID NO:28:

(i) SEQUENCE CHARACTERISTICS:
       (A) LENGTH: 374 amino acids
       (B) TYPE: amino acid
       (D) TOPOLOGY: linear (ii) MOLECULE TYPE: peptide (v) FRAGMENT TYPE: internal (xi) SEQUENCE DESCRIPTION: SEQ ID NO:28:

```
Met Gly Trp Ser Cys Ile Ile Leu Phe Leu Val Ala Thr Ala Thr Gly
1               5                   10                  15

Val His Ser Ala Met His Val Ala Gln Pro Ala Val Val Leu Ala Ser
            20                  25                  30

Ser Arg Gly Ile Ala Ser Phe Val Cys Glu Tyr Ala Ser Pro Gly Lys
        35                  40                  45

Ala Thr Glu Val Arg Val Thr Val Leu Arg Gln Ala Asp Ser Gln Val
    50                  55                  60

Thr Glu Val Cys Ala Ala Thr Tyr Met Met Gly Asn Glu Leu Thr Phe
65                  70                  75                  80

Leu Asp Asp Ser Ile Cys Thr Gly Thr Ser Ser Gly Asn Gln Val Asn
                85                  90                  95

Leu Thr Ile Gln Gly Leu Arg Ala Met Asp Thr Gly Leu Tyr Ile Cys
            100                 105                 110

Lys Val Glu Leu Met Tyr Pro Pro Pro Tyr Leu Gly Ile Gly Asn
        115                 120                 125

Gly Thr Gln Ile Tyr Val Ile Asp Pro Glu Pro Cys Pro Asp Ser Asp
    130                 135                 140

Gln Glu Ser Lys Tyr Gly Pro Pro Ser Pro Ser Pro Ala Pro Glu
145                 150                 155                 160

Phe Glu Gly Ala Pro Ser Val Phe Leu Phe Pro Pro Lys Pro Lys Asp
                165                 170                 175

Thr Leu Met Ile Ser Arg Thr Pro Glu Val Thr Cys Val Val Val Asp
            180                 185                 190
```

Val Ser Gln Glu Asp Pro Glu Val Gln Phe Asn Trp Tyr Val Asp Gly
        195                 200                 205

Val Glu Val His Asn Ala Lys Thr Lys Pro Arg Glu Glu Gln Phe Asn
        210                 215                 220

Ser Thr Tyr Arg Val Val Ser Val Leu Thr Val Leu His Gln Asp Trp
225                 230                 235                 240

Leu Asn Gly Lys Glu Tyr Lys Cys Lys Val Ser Asn Lys Gly Leu Pro
                245                 250                 255

Ser Ser Ile Glu Lys Thr Ile Ser Lys Ala Lys Gly Gln Pro Arg Glu
                260                 265                 270

Pro Gln Val Tyr Thr Leu Pro Pro Ser Gln Glu Glu Met Thr Lys Asn
            275                 280                 285

Gln Val Ser Leu Thr Cys Leu Val Lys Gly Phe Tyr Pro Ser Asp Ile
        290                 295                 300

Ala Val Glu Trp Glu Ser Asn Gly Gln Pro Glu Asn Asn Tyr Lys Thr
305                 310                 315                 320

Thr Pro Pro Val Leu Asp Ser Asp Gly Ser Phe Phe Leu Tyr Ser Arg
                325                 330                 335

Leu Thr Val Asp Lys Ser Arg Trp Gln Glu Gly Asn Val Phe Ser Cys
                340                 345                 350

Ser Val Met His Glu Ala Leu His Asn His Tyr Thr Gln Lys Ser Leu
            355                 360                 365

Ser Leu Ser Leu Gly Lys
        370

(2) INFORMATION FOR SEQ ID NO:29:

(i) SEQUENCE CHARACTERISTICS:
        (A) LENGTH: 2770 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

CATTCGCTTA CCTCGAGAAG CTTGAGATCA CAGTTCTCTC TACAGTTACT GAGCACACAG     60

GACCTCACCA TGGGATGGAG CTGTATCATC CTCTTCTTGG TAGCAACAGC TACAGGTAAG    120

GGGCTCACAG TAGCAGGCTT GAGGTCTGGA CATATATATG GGTGACAATG ACATCCACTT    180

TGCCTTTCTC TCCACAGGTG TCCACTCCGC AATGCACGTG GCCCAGCCTG CTGTGGTACT    240

GGCCAGCAGC CGAGGCATCG CCAGCTTTGT GTGTGAGTAT GCATCTCCAG CAAAGCCAC    300

TGAGGTCCGG GTGACAGTGC TTCGGCAGGC TGACAGCCAG GTGACTGAAG TCTGTGCGGC    360

AACCTACATG ATGGGGAATG AGTTGACCTT CCTAGATGAT TCCATCTGCA CGGGCACCTC    420

CAGTGGAAAT CAAGTGAACC TCACTATCCA AGGACTGAGG GCCATGGACA CGGGACTCTA    480

CATCTGCAAG GTGGAGCTCA TGTACCCACC GCCATACTAC CTGGGCATAG CAACGGAGC    540

CCAGATTTCA GGTGAGTCCT TACAACCTCT CTCTTCTATT CAGCTTAAAT AGATTTTACT    600

GCATTTGTTG GGGGGGAAAT GTGTGTATCT GAATTTCAGG TCATGAAGGA CTAGGGACAC    660

CTTGGGAGTC AGAAAGGGTC ATTGGGAGCC CGGGCTGATG CAGACAGACA TCCTCAGCTC    720

CCAGACTTCA TGGCCAGAGA TTTATAGTCT AGAGGATCCC CAGCTTTCTG GGGCAGGCCA    780

GGCCTGACCT TGGCTTTGGG GCAGGGAGGG GGCTAAGGTG AGGCAGGTGG CGCCAGCAGG    840

TGCACACCCA ATGCCCATGA GCCCAGACAC TGGACGCTGA ACCTCGCGGA CAGTTAAGAA    900

-continued

```
CCCAGGGGCC TCTGCGCCTG GGCCCAGCTC TGTCCCACAC CGCGGTCACA TGGCACCACC      960
TCTCTTGCAG CCTCCACCAA GGGCCCATCG GTCTTCCCCC TGGCACCCTC CTCCAAGAGC     1020
ACCTCTGGGG GCACAGCGGC CCTGGGCTGC CTGGTCAAGG ACTACTTCCC CGAACCGGTG     1080
ACGGTGTCGT GGAACTCAGG CGCCCTGACC AGCGGCGTGC ACACCTTCCC GGCTGTCCTA     1140
CAGTCCTCAG GACTCTACTC CCTCAGCAGC GTGGTGACCG TGCCCTCCAG CAGCTTGGGC     1200
ACCCAGACCT ACATCTGCAA CGTGAATCAC AAGCCCAGCA ACACCAAGGT GGACAAGAAA     1260
GTTGGTGAGA GGCCAGCACA GGGAGGGAGG GTGTCTGCTG GAAGCAGGCT CAGCGCTCCT     1320
GCCTGGACGC ATCCCGGCTA TGCAGCCCCA GTCCAGGGCA GCAAGGCAGG CCCCGTCTGC     1380
CTCTTCACCC GGAGCCTCTG CCCGCCCCAC TCATGCTCAG GGAGAGGGTC TTCTGGCTTT     1440
TTCCCAGGCT CTGGGCAGGC ACAGGCTAGG TGCCCCTAAC CCAGGCCCTG CACACAAAGG     1500
GGCAGGTGCT GGGCTCAGAC CTGCCAAGAG CCATATCCGG GAGGACCCTG CCCCTGACCT     1560
AAGCCCACCC CAAAGGCCAA ACTCTCCACT CCCTCAGCTC GGACACCTTC TCCTCCCA      1620
GATTCCAGTA ACTCCCAATC TTCTCTCTGC AGAGCCCAAA TCTTGTGACA AAACTCACAC     1680
ATGCCCACCG TGCCCAGGTA AGCCAGCCCA GGCCTCGCCC TCCAGCTCAA GGCGGGACAG     1740
GTGCCCTAGA GTAGCCTGCA TCCAGGGACA GGCCCCAGCC GGGTGCTGAC ACGTCCACCT     1800
CCATCTCTTC CTCAGCACCT GAACTCCTGG GGGGACCGTC AGTCTTCCTC TTCCCCCCAA     1860
AACCCAAGGA CACCCTCATG ATCTCCCGGA CCCCTGAGGT CACATGCGTG GTGGTGGACG     1920
TGAGCCACGA AGACCCTGAG GTCAAGTTCA ACTGGTACGT GGACGGCGTG GAGGTGCATA     1980
ATGCCAAGAC AAAGCCGCGG GAGGAGCAGT ACAACAGCAC GTACCGGGTG GTCAGCGTCC     2040
TCACCGTCCT GCACCAGGAC TGGCTGAATG GCAAGGAGTA CAAGTGCAAG GTCTCCAACA     2100
AAGCCCTCCC AGCCCCCATC GAGAAAACCA TCTCCAAAGC CAAAGGTGGG ACCCGTGGGG     2160
TGCGAGGGCC ACATGGACAG AGGCCGGCTC GGCCCACCCT CTGCCCTGAG AGTGACCGCT     2220
GTACCAACCT CTGTCCTACA GGGCAGCCCC GAGAACCACA GGTGTACACC CTGCCCCCAT     2280
CCCGGGATGA GCTGACCAAG AACCAGGTCA GCCTGACCTG CCTGGTCAAA GGCTTCTATC     2340
CCAGCGACAT CGCCGTGGAG TGGGAGAGCA ATGGGCAGCC GGAGAACAAC TACAAGACCA     2400
CGCCTCCCGT GCTGGACTCC GACGGCTCCT TCTTCCTCTA CAGCAAGCTC ACCGTGGACA     2460
AGAGCAGGTG GCAGCAGGGG AACGTCTTCT CATGCTCCGT GATGCATGAG GCTCTGCACA     2520
ACCACTACAC GCAGAAGAGC CTCTCCCTGT CTCCGGGTAA ATGAGTGCGA CGGCCGGCAA     2580
GCCCCGCTCC CCGGGCTCTC GCGGTCGCAC GAGGATGCTT GGCACGTACC CCCTGTACAT     2640
ACTTCCCGGG CGCCCAGCAT GGAAATAAAG CACCCAGCGC TGCCCTGGGC CCCTGCGAGA     2700
CTGTGATGGT TCTTTCCACG GGTCAGGCCG AGTCTGAGGC CTGAGTGGCA TGAGGGAGGC     2760
AGAGCGGGTC                                                            2770
```

(2) INFORMATION FOR SEQ ID NO:30:

(i) SEQUENCE CHARACTERISTICS:
        (A) LENGTH: 238 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:30:

Met Gly Trp Ser Cys Ile Ile Leu Phe Leu Val Ala Thr Ala Thr Gly

```
1               5                 10                15
Val His Ser Ala Met His Val Ala Gln Pro Ala Val Val Leu Ala Ser
                20                  25                  30
Ser Arg Gly Ile Ala Ser Phe Val Cys Glu Tyr Ala Ser Pro Gly Lys
            35                  40                  45
Ala Thr Glu Val Arg Val Thr Val Leu Arg Gln Ala Asp Ser Gln Val
        50                  55                  60
Thr Glu Val Cys Ala Ala Thr Tyr Met Met Gly Asn Glu Leu Thr Phe
65                  70                  75                  80
Leu Asp Asp Ser Ile Cys Thr Gly Thr Ser Gly Asn Gln Val Asn
                85                  90                  95
Leu Thr Ile Gln Gly Leu Arg Ala Met Asp Thr Gly Leu Tyr Ile Cys
                100                 105                 110
Lys Val Glu Leu Met Tyr Pro Pro Pro Tyr Tyr Leu Gly Ile Gly Asn
                115                 120                 125
Gly Ala Gln Ile Thr Val Ala Ala Pro Ser Val Phe Ile Phe Pro Pro
        130                 135                 140
Ser Asp Glu Gln Leu Lys Ser Gly Thr Ala Ser Val Val Cys Leu Leu
145                 150                 155                 160
Asn Asn Phe Tyr Pro Arg Glu Ala Lys Val Gln Trp Lys Val Asp Asn
                165                 170                 175
Ala Leu Gln Ser Gly Asn Ser Gln Glu Ser Val Thr Glu Gln Asp Ser
                180                 185                 190
Lys Asp Ser Thr Tyr Ser Leu Ser Ser Thr Leu Thr Leu Ser Lys Ala
                195                 200                 205
Asp Tyr Glu Lys His Lys Val Tyr Ala Cys Glu Val Thr His Gln Gly
        210                 215                 220
Leu Ser Ser Pro Val Thr Lys Ser Phe Asn Arg Gly Glu Cys
225                 230                 235
```

(2) INFORMATION FOR SEQ ID NO:31:

(i) SEQUENCE CHARACTERISTICS:
        (A) LENGTH: 1708 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

```
CATTCGCTTA CCTCGAGAAG CTTGAGATCA CAGTTCTCTC TACAGTTACT GAGCACACAG    60
GACCTCACCA TGGGATGGAG CTGTATCATC CTCTTCTTGG TAGCAACAGC TACAGGTAAG   120
GGGCTCACAG TAGCAGGCTT GAGGTCTGGA CATATATATG GGTGACAATG ACATCCACTT   180
TGCCTTTCTC TCCACAGGTG TCCACTCCGC AATGCACGTG GCCCAGCCTG CTGTGGTACT   240
GGCCAGCAGC CGAGGCATCG CCAGCTTTGT GTGTGAGTAT GCATCTCCAG GCAAAGCCAC   300
TGAGGTCCGG GTGACAGTGC TTCGGCAGGC TGACAGCCAG GTGACTGAAG TCTGTGCGGC   360
AACCTACATG ATGGGGAATG AGTTGACCTT CCTAGATGAT CCATCTGCA CGGGCACCTC    420
CAGTGGAAAT CAAGTGAACC TCACTATCCA AGGACTGAGG GCCATGGACA CGGGACTCTA   480
CATCTGCAAG GTGGAGCTCA TGTACCCACC GCCATACTAC CTGGGCATAG CAACGGAGC    540
CCAGATTAAA CGTGAGTAGA ATTTAAACTT TGCTTCCTCA GTTTCTAGAA GAATGGCTGC   600
AAAGAGCTCC AACAAAACAA TTTAGAACTT TATTAAGGAA TAGGGGGAAG CTAGGAAGAA   660
```

```
ACTCAAAACA TCAAGATTTT AAATACGCTT CTTGGTCTCC TTGCTATAAT TATCTGGGAT      720

AAGCATGCTG TTTTCTGTCT GTCCCTAACA TGCCCTGTGA TTATCCGCAA CAACACACC       780

CAAGGGCAGA ACTTTGTTAC TTAAACACCA TCCTGTTTGC TTCTTTCCTC AGGAACTGTG      840

GCTGCACCAT CTGTCTTCAT CTTCCCGCCA TCTGATGAGC AGTTGAAATC TGGAACTGCC      900

TCTGTTGTGT GCCTGCTGAA TAACTTCTAT CCCAGAGAGG CCAAAGTACA GTGGAAGGTG      960

GATAACGCCC TCCAATCGGG TAACTCCCAG GAGAGTGTCA CAGAGCAGGA CAGCAAGGAC     1020

AGCACCTACA GCCTCAGCAG CACCCTGACG CTGAGCAAAG CAGACTACGA GAAACACAAA     1080

GTCTACGCCT GCGAAGTCAC CCATCAGGGC CTGAGCTCGC CCGTCACAAA GAGCTTCAAC     1140

AGGGGAGAGT GTTAGAGGGA GAAGTGCCCC CACCTGCTCC TCAGTTCCAG CCTGACCCCC     1200

TCCCATCCTT TGGCCTCTGA CCCTTTTTCC ACAGGGGACC TACCCCTATT GCGGTCCTCC     1260

AGCTCATCTT TCACCTCACC CCCTCCTCC TCCTTGGCTT TAATTATGCT AATGTTGGAG      1320

GAGAATGAAT AAATAAAGTG AATCTTTGCA CCTGTGGTTT CTCTCTTTCC TCAATTTAAT     1380

AATTATTATC TGTTGTTTAC CAACTACTCA ATTTCTCTTA TAAGGGACTA AATATGTAGT     1440

CATCCTAAGG CGCATAACCA TTTATAAAAA TCATCCTTCA TTCTATTTTA CCCTATCATC     1500

CTCTGCAAGA CAGTCCTCCC TCAAACCCAC AAGCCTTCTG TCCTCACAGT CCCCTGGGCC     1560

GTGGTAGGAG AGACTTGCTT CCTTGTTTTC CCCTCCTCAG CAAGCCCTCA TAGTCCTTTT     1620

TAAGGGTGAC AGGTCTTACG GTCATATATC CTTTGATTCA ATTCCCTGGG AATCAACCAA     1680

GGCAAATTTT TCAAAAGAAG AAACCTGC                                       1708
```

(2) INFORMATION FOR SEQ ID NO:32:

(i) SEQUENCE CHARACTERISTICS:
        (A) LENGTH: 238 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:32:

```
Met Gly Trp Ser Cys Ile Ile Leu Phe Leu Val Ala Thr Ala Thr Gly
1               5                   10                  15

Val His Ser Ala Met His Val Ala Gln Pro Ala Val Val Leu Ala Ser
            20                  25                  30

Ser Arg Gly Ile Ala Ser Phe Val Cys Glu Tyr Ala Ser Pro Gly Lys
        35                  40                  45

Ala Thr Glu Val Arg Val Thr Val Leu Arg Gln Ala Asp Ser Gln Val
    50                  55                  60

Thr Glu Val Cys Ala Ala Thr Tyr Met Met Gly Asn Glu Leu Thr Phe
65                  70                  75                  80

Leu Asp Asp Ser Ile Cys Thr Gly Thr Ser Ser Gly Asn Gln Val Asn
                85                  90                  95

Leu Thr Ile Gln Gly Leu Arg Ala Met Asp Thr Gly Leu Tyr Ile Cys
            100                 105                 110

Lys Val Glu Leu Met Tyr Pro Pro Pro Tyr Tyr Leu Gly Ile Gly Asn
        115                 120                 125

Gly Ala Gln Ile Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160
```

```
Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
        210                 215                 220

Leu Ser Ser Pro Val Thr Lys Ser Phe Asn Arg Gly Glu Cys
225                 230                 235
```

CTLA4-Cγ4 FUSION PROTEINS

CROSS REFERENCE TO RELATED APPLICATIONS

This application is a divisional application of U.S. Ser. No. 08/595,590, filed on Feb. 2, 1996. The contents of that application are specifically incorporated herein by reference.

BACKGROUND OF THE INVENTION

To induce antigen-specific T cell activation and clonal expansion, two signals provided by antigen-presenting cells (APCs) must be delivered to the surface of resting T lymphocytes (Jenkins, M. and Schwartz, R. (1987) *J. Exp. Med.* 165:302–319; Mueller, D. L., et al. (1990) *J. Immunol.* 144:3701–3709; Williams, I. R. and Unanue, E. R. (1990) *J. Immunol.* 145:85–93). The first signal, which confers specificity to the immune response, is mediated via the T cell receptor (TCR) following recognition of foreign antigenic peptide presented in the context of the major histocompatibility complex (MHC). The second signal, termed costimulation, induces T cells to proliferate and become functional (Schwartz, R. H. (1990) *Science* 248:1349–1356). Costimulation is neither antigen-specific, nor MHC restricted and is thought to be provided by one or more distinct cell surface molecules expressed by APCs (Jenkins, M. K., et al. (1988) *J. Immunol.* 140:3324–3330; Linsley, P. S., et al. (1991) *J. Exp. Med.* 173:721–730; Gimmi, C. D., et al., (1991) *Proc. Natl. Acad. Sci. USA.* 88:6575–6579; Young, J. W., et al. (1992) *J. Clin. Invest.* 90:229–237; Koulova, L., et al. (1991) *J. Exp. Med.* 173:759–762; Reiser, H., et al. (1992) *Proc. Natl. Acad. Sci. USA.* 89:271–275; van-Seventer, G. A., et al. (1990) *J. Immunol.* 144:4579–4586; LaSalle, J. M., et al., (1991) *J. Immunol.* 147:774–80; Dustin, M. I., et al., (1989) *J. Exp. Med.* 169:503; Armitage, R. J., et al. (1992) *Nature* 357:80–82; Liu, Y., et al. (1992) *J. Exp. Med.* 175:437–445).

Considerable evidence suggests that the B7-1 protein (CD80; originally termed B7), expressed on APCs, is one such critical costimulatory molecule (Linsley, P. S., et al., (1991) *J. Exp. Med.* 173:721–730; Gimmi, C. D., et al., (1991) *Proc. Natl. Acad Sci. USA.* 88:6575–6579; Koulova, L., et al., (1991) *J. Exp. Med.* 173:759–762; Reiser, H., et al. (1992) *Proc. Natl. Acad Sci. USA.* 89:271–275; Linsley, P. S. et al. (1990) *Proc. Natl. Acad. Sci. USA.* 87: 5031–5035; Freeman, G. J. et al. (1991) *J. Exp. Med.* 174:625–631.). Recent evidence suggests the presence of additional costimulatory molecules on the surface of activated B lymphocytes (Boussiotis V. A., et al. (1993) *Proc. Natl. Acad Sci. USA,* 90:11059–11063; Freeman G. J., et al. (1993) *Science* 262:907–909; Freeman G. J., et al. (1993) *Science* 262:909–911; and Hathcock K. S., et al. (1993) *Science* 262:905–907). The human B lymphocyte antigen B7-2 (CD86) has been cloned and is expressed by human B cells at about 24 hours following stimulation with either anti-immunoglobulin or anti-MHC class II monoclonal antibody (Freeman G. J., et al. (1993) *Science* 262:909–911). At about 48 to 72 hours post activation, human B cells express both B7-1 and a third CTLA4 counter-receptor which is identified by a monoclonal antibody BB-1, which also binds B7-1 (Yokochi, T., et al. (1982) *J. Immunol.* 128:823–827). The BB-1 antigen is also expressed on B7-1 negative activated B cells and can costimulate T cell proliferation without detectable IL-2 production, indicating that the B7-1 and BB-1 molecules are distinct (Boussiotis V. A., et al. (1993) *Proc. Natl. Acad. Sci. USA* 90:11059–11063). The presence of these costimulatory molecules on the surface of activated B lymphocytes indicates that T cell costimulation is regulated, in part, by the temporal expression of these molecules following B cell activation.

B7-1 is a counter-receptor for two ligands expressed on T lymphocytes. The first ligand, termed CD28, is constitutively expressed on resting T cells and increases after activation. After signaling through the T cell receptor, ligation of CD28 induces T cells to proliferate and secrete IL-2 (Linsley, P.S., et al. (1991) *J. Exp. Med.* 173: 721–730; Gimmi, C. D., et al. (1991) *Proc. Natl. Acad. Sci. USA.* 88:6575–6579; Thompson, C. B., et al. (1989) *Proc. Natl. Acad. Sci. USA.* 86:1333–1337; June, C. H., et al. (1990) *Immunol. Today.* 11:211–6; Harding, F. A., et al. (1992) *Nature.* 356:607–609.). The second ligand, termed CTLA4, is homologous to CD28, but is not expressed on resting T cells and appears following T cell activation (Brunet, J. F., et al., (1987) *Nature* 328:267–270). Like B7-1, B7-2 is a counter-receptor for both CD28 and CTLA4 (Freeman G. J., et al. (1993) *Science* 262:909–911). CTLA4 was first identified as a mouse cDNA clone, in a library of cDNA from a cytotoxic T cell clone subtracted with RNA from a B cell lymphoma (Brunet, J. F., et al. (1987) supra). The mouse CTLA4 cDNA was then used as a probe to identify the human and mouse CTLA4 genes (Harper, K., et al. (1991) *J. Immunol.* 147:1037–1044; and Dariavich, et al. (1988) *Eur. J. Immunol.* 18(12):1901–1905, sequence modified by Linsley, P. S., et al. (1991) *J. Exp. Med.* 174:561–569). A probe from the V domain of the human gene was used to detect the human cDNA which allowed the identification of the CTLA4 leader sequence (Harper, K., et al. (1991) supra).

Soluble derivatives of cell surface glycoproteins in the immunoglobulin gene superfamily have been made consisting of an extracellular domain of the cell surface glycoprotein fused to an immunoglobulin constant (Fc) region (see e.g., Capon, D. J. et al. (1989) *Nature* 337:525–531 and Capon U.S. Pat. Nos. 5,116,964 and 5,428,130 [CD4-IgG1 constructs]; Linsley, P. S. et al. (1991) *J. Exp. Med.* 173:721–730 [a CD28-IgG1 construct and a B7-1-IgG1 construct]; and Linsley, P. S. et al. (1991) *J. Exp. Med.* 174:561–569 and U.S. Pat. No. 5,434,131 [a CTLA4-IgG1). Such fusion proteins have proven useful for studying receptor-ligand interactions. For example, a CTLA4-IgG immunoglobulin fusion protein was used to study interactions between CTLA4 and its natural ligands (Linsley, P. S., et al., (1991) *J. Exp. Med.* 174:561–569; International Application WO93/00431; and Freeman G. J., et al. (1993) *Science* 262:909–911).

The importance of the B7: CD28/CTLA4 costimulatory pathway has been demonstrated in vitro and in several in vivo model systems. Blockade of this costimulatory pathway results in the development of antigen specific tolerance in murine and human systems (Harding, F. A., et al. (1992) *Nature* 356:607–609; Lenschow, D. J., et al. (1992) *Science* 257:789–792; Turka, L. A., et al. (1992) *Proc. Natl. Acad. Sci. USA* 89:11102–11105; Gimmi, C. D., et al. (1993) *Proc. Natl. Acad. Sci. USA* 90:6586–6590; Boussiotis, V., et al. (1993) *J. Exp. Med.* 178:1753–1763). Conversely, transfection of a B7-1 gene into B7-1 negative murine tumor cells to thereby express B7-1 protein on the tumor cell surface induces T-cell mediated specific immunity accompanied by tumor rejection and long lasting protection to tumor challenge (Chen, L., et al. (1992) *Cell* 71: 1093–1102; Townsend, S. E. and Allison, J. P. (1993) *Science* 259:368–370; Baskar, S., et al. (1993) *Proc. Nati. Acad. Sci. USA* 90:5687–5690.). Therefore, approaches which manipulate the B7: CD28/CTLA4 interaction to thereby stimulate or suppress immune responses would be beneficial therapeutically.

SUMMARY OF THE INVENTION

This invention pertains to CTLA4-immunoglobulin fusion proteins having modified immunoglobulin constant (IgC) region-mediated effector functions and to nucleic acids encoding the proteins. In one embodiment, the fusion proteins of the present invention have been constructed by fusing a peptide having a CTLA4 activity and a second peptide comprising an immunoglobulin constant region to create a CTLA4Ig fusion protein. In another embodiment, the variable regions of immunoglobulin heavy and light chains have been replaced by the B7-binding extracellular domain of CTLA4 to create CTLA4-Ab fusion proteins. As used herein, the term "CTLA4-immunoglobulin fusion protein" refers to both the CTLA4Ig and CTLA4-Ab forms. In a preferred embodiment, the fusion proteins of the invention have been modified to reduce their ability to activate complement and/or bind to Fc receptors. In one embodiment, an IgC region of an isotype other than Cγ1 is used in the fusion protein and the modified effector function(s) can be assessed relative to a Cγ1-containing molecule (e.g., an IgG1 fusion protein). In another embodiment, a mutated IgC region (of any isotype) is used in the fusion protein and the modified effector function can be assessed relative to an antibody or Ig fusion protein containing the non-mutated form of the IgC region.

The CTLA4-immunoglobulin fusion proteins of the invention are useful for inhibiting the interaction of CTLA4 ligands (e.g., B7 family members such as B7-1 and B7-2) with receptors on T cells (e.g., CD28 and/or CTLA4) to thereby inhibit delivery of a costimulatory signal in the T cells and thus downmodulate an immune response. Use of the CTLA4-immunoglobulin fusion proteins of the invention is applicable in a variety of situations, such as to inhibit transplant rejection or autoimmune reactions in a subject. In these situations, immunoglobulin constant region-mediated biological effector mechanisms, such as complement-mediated cell lysis, Fc receptor-mediated phagocytosis or antibody-dependent cellular cytotoxicity, may induce detrimental side effects in the subject and are therefore undesirable. The CTLA4-immunoglobulin fusion proteins of the invention exhibit reduced IgC region-mediated effector functions compared to a CTLA4-immunoglobulin fusion protein in which the IgG1 constant region is used and, thus are likely to have improved immunoinhibitory properties. These compositions can also be used for immunomodulation, to produce anti-CTLA4 antibodies, to purify CTLA4 ligands and in screening assays. The CTLA4-Ab fusion proteins are particularly useful when bivalent preparations are preferred, i.e. when crosslinking is desired.

One aspect of the invention pertains to isolated nucleic acid molecules encoding modified CTLA4-immunoglobulin fusion proteins. The nucleic acids of the invention comprise a nucleotide sequence encoding a first peptide having a CTLA4 activity and a nucleotide sequence encoding a second peptide comprising an immunoglobulin constant region which is modified to reduce at least one constant region-mediated biological effector function. A peptide having a CTLA4 activity is defined herein as a peptide having at least one biological activity of the CTLA4 protein, e.g., the ability to bind to the natural ligand(s) of the CTLA4 antigen on immune cells, such as B7-1 and/or B7-2 on B cells, or other known or as yet undefined ligands on immune cells, and inhibit (e.g., block) or interfere with immune cell mediated responses. In one embodiment, the peptide having a CTLA4 activity binds B7-1 and/or B-2 and comprises an extracellular domain of the CTLA4 protein. Preferably, the extracellular domain includes amino acid residues 20–144 of the human CTLA4 protein (amino acid positions 20–144 of SEQ ID NO: 24, 26 and 28).

The present invention also contemplates forms of the extracellular domain of CTLA4 which are expressed without Ig constant regions and are expressed in *E. coli*. These soluble forms of the CTLA4 extracellular domain, although not glycosylated, are fully functional and have similar uses as the CTLA4 immunoglobulin fusion proteins of the invention.

The nucleic acids of the invention further comprise a nucleotide sequence encoding a second peptide comprising an immunoglobulin constant region which is modified to reduce at least one Ig constant region-mediated biological effector function. Preferably, the immunoglobulin constant region comprises a hinge region, a CH2 domain and a CH3 domain derived from Cγ1, Cγ2, Cγ3 or Cγ4. In one embodiment, the constant region segment is altered (e.g., mutated at specific amino acid residues by substitution, deletion or addition of amino acid residues) to reduce at least one IgC region-mediated effector function. In another embodiment, a constant region other than Cγ1 that exhibits reduced IgC region-mediated effector functions relative to Cγ1 is used in the fusion protein. In a preferred embodiment, the CH2 domain is modified to reduce a biological effector function, such as complement activation, Fc receptor interaction, or both complement activation and Fc receptor interaction. For example, to reduce Fc receptor interaction, at least one amino acid residue selected from a hinge link region of the CH2 domain (e.g., amino acid residues at positions 234–237 of an intact heavy chain protein) is modified by substitution, addition or deletion of amino acids. In another embodiment, to reduce complement activation ability, a constant region which lacks the ability to activate complement, such as Cγ4 or Cγ2 is used in the fusion protein (instead of a Cγ1 constant region which is capable of activating complement). In another embodiment the variable region of the heavy and light chain is replaced with a polypeptide having CTLA4 activity creating a CTLA4-Ab molecule. In a preferred embodiment the heavy chain constant region of the CTLA4-Ab molecule comprises a hinge region, a CH2 domain and a CH3 domain derived from Cγ1, Cγ2, Cγ3 or Cγ4. In a preferred embodiment the light chain constant region of the CTLA4-Ab molecule comprises an Ig signal sequence, the CTLA4 extracellular domain, and the light chain (kappa or lambda) constant domain.

The nucleic acids obtained in accordance with this invention can be inserted into various expression vectors, which in turn direct the synthesis of the corresponding protein in a variety of hosts, particularly eucaryotic cells, such as mammalian or insect cell culture and procaryotic cells, such as *E. coli*. Expression vectors within the scope of the invention comprise a nucleic acid as described herein and a promotor operably linked to the nucleic acid. Such expression vectors can be used to transfect host cells to thereby produce fusion proteins encoded by nucleic acids as described herein.

Another aspect of the invention pertains to isolated CTLA4-immunoglobulin fusion proteins comprising a first peptide having a CTLA4 activity and a second peptide comprising an immunoglobulin constant region which is modified to reduce at least one constant region-mediated biological effector function relative to a CTLA4-IgG1 fusion protein. A preferred CTLA4-immunoglobulin fusion protein comprises an extracellular domain of the CTLA4 protein (e.g., amino acid positions 20–144 of the human CTLA4-immunoglobulin fusion protein shown in SEQ ID NO: 24, 26 and 28) linked to an immunoglobulin constant region comprising a hinge region, a CH2 domain and a CH3 domain derived from Cγ1, Cγ2, Cγ3 or Cγ4. A preferred constant domain used to reduce the complement activating ability of the fusion protein is Cγ4. In one embodiment, the CH2 domain of the immunoglobulin constant region is modified to reduce at least one biological effector function, such as complement activation or Fc receptor interaction. In a particularly preferred embodiment, the CTLA4-immunoglobulin fusion protein includes a CH2 domain which is modified by substitution of an amino acid residue at position 234, 235 and/or 237 of an intact heavy chain protein. One example of such a protein is a CTLA4-immunoglobulin fusion protein fused to IgG4 comprising an amino acid sequence shown in SEQ ID NO: 28 or a CTLA4-immunoglobulin fused to IgG1 fusion protein comprising an amino acid sequence shown in SEQ ID NO: 24.

The CTLA4-immunoglobulin fusion proteins of the invention can be incorporated into pharmaceutical compositions and administered to a subject to inhibit an interaction between a CTLA4 ligand (e.g., B7-1 and/or B7-2) and a receptor therefor (e.g., CD28 and/or CTLA4) on the surface of a T cell, to thereby suppress cell-mediated immune responses in vivo. Inhibition of the CTLA4 ligand/receptor interaction may be useful for both general immunosuppression and to induce antigen-specific T cell tolerance in a subject for use in preventing transplantation rejection (solid organ, skin and bone marrow) or graft versus host disease, particularly in allogeneic bone marrow transplantation. The CTLA4-immunoglobulin fusion proteins can also be used therapeutically in the treatment of autoimmune diseases, allergy and allergic reactions, transplantation rejection and established graft versus host disease in a subject. Moreover, the CTLA4-immunoglobulin fusion proteins of the invention can be used as immunogens to produce anti-CTLA4 antibodies in a subject, to purify CTLA4 ligands and in screening assays to identify molecules which inhibit the interaction of CTLA4 with a CTLA4 ligand.

BRIEF DESCRIPTION OF THE DRAWINGS

FIG. 1 is a schematic diagram of the "zip up" polymerase chain reaction (PCR) procedure used to contrust gene fusions.

FIGS. 2A–B show the amino acid mutations introduced into the hinge and CH2 domains of hCTLA4-IgG1m (panel A) and hCTLA4-IgG4m (panel B). Mutated amino acid residues are underlined.

FIGS. 5A–B are graphic representations of Fc receptor binding assays depicting the ability of CTLA4-IgG1 or CTLA4-IgG4 to bind to Fc receptors. In panel A, the ability of unlabeled CTLA4-IgG1 or unlabeled CTLA4-IgG4 to compete for the binding of $^{125}$I-labeled CTLA4-IgG1 to FcRI-positive U937 cells is depicted. In panel B, the percent specific activity of unlabeled CTLA4-IgG1, CTLA4-IgG4 or hIgG1 used to compete itself for binding to U937 cells is depicted.

FIGS. 6A–C are graphic representations of complement activation assays depicting the ability of CTLA4-IgG1, CTLA4-IgG4m or anti-B7-1 mAb (4B2) to activate complement-mediated lysis of CHO-B7-1 cells. In panel A, guinea pig complement is used as the complement source. In panel B, human serum is used as the complement source. In panel C, control untransfected CHO cells are used as the target for complement-mediated lysis.

FIG. 8 is a graphic representation of a competition curve demonstrating that soluble CTLA4 expressed in *E. coli* is functional and competes with unlabeled CTLA4Ig for binding to plate-bound B7-1.

DETAILED DESCRIPTION OF THE INVENTION

Figure 3:
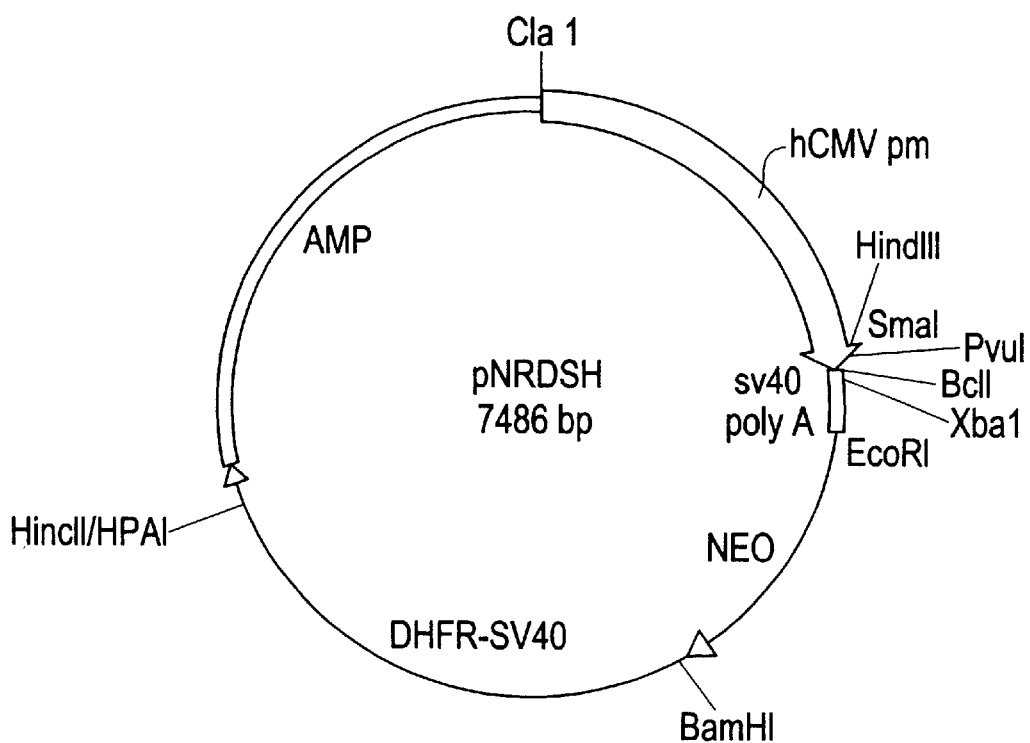
FIG. 3 is a schematic diagram of the expression vector pNRDSH.

This invention features isolated CTLA4-immunoglobulin fusion proteins which have been modified to reduce immunoglobulin constant (IgC) region-mediated effector functions. The invention also features isolated nucleic acids encoding the proteins, methods for producing the CTLA4-immunoglobulin fusion proteins of the invention and methods for using the CTLA4-immunoglobulin fusion proteins of the invention for immunomodulation. *E. coli*-expressed forms of CTLA4 are also disclosed. These and other aspects of the invention are described in further detail in the following subsections:

I. Chimeric CTLA4-immunoglobulin Gene Fusions

The invention provides isolated nucleic acids encoding CTLA4-immunoglobulin fusion proteins. The CTLA4-immunoglobulin fusion proteins are comprised of two components: a first peptide having a CTLA4 activity and a second peptide comprising an immunoglobulin constant region which, in certain embodiments is modified to reduce at least one constant region-mediated biological effector function. Accordingly, the isolated nucleic acids of the invention comprise a first nucleotide sequence encoding the first peptide having a CTLA4 activity and a second nucleotide sequence encoding the second peptide comprising an immunoglobulin constant region which, in a preferred embodiment, is modified to reduce at least one constant region-mediated biological effector function. In the case of CTLA4Ig forms, the first and second nucleotide sequences are linked (i.e., in a 5' to 3' orientation by phosphodiester bonds) such that the translational frame of the CTLA4 and IgC coding segments are maintained (i.e., the nucleotide sequences are joined together in-frame). Thus, expression (i.e., transcription and translation) of the nucleotide sequences produces a functional CTLA4Ig fusion protein. In the case of the CTLA4-Ab fusion proteins, the heavy chain gene is constructed such that the CTLA4 extracellular binding domain is linked to a 5' signal sequence and a 3' immunoglobulin CH1, hinge, CH2, and CH3 domain. CTLA4-light chain constructs are prepared in which an Ig signal sequence, an intron, the CTLA4 extracellular domain, an intron, and the light chain constant domain are linked. The DNA encoding the heavy and light chains is then expressed using an appropriate expression vector as described in the Examples.

The term "nucleic acid" as used herein is intended to include fragments or equivalents thereof. The term "equivalent" is intended to include nucleotide sequences encoding functionally equivalent CTLA4-immunoglobulin fusion proteins, i.e., proteins which have the ability to bind to the natural ligand(s) of the CTLA4 antigen on immune cells, such as B7-1 and/or B7-2 on B cells, and inhibit (e.g., block) or interfere with immune cell mediated responses.

The term "isolated" as used throughout this application refers to a nucleic acid or fusion protein substantially free of cellular material or culture medium when produced by recombinant DNA techniques, or chemical precursors or other chemicals when chemically synthesized. An isolated nucleic acid is also free of sequences which naturally flank the nucleic acid (i.e., sequences located at the 5' and 3' ends of the nucleic acid) in the organism from which the nucleic acid is derived.

The nucleic acids of the invention can be prepared by standard recombinant DNA techniques. For example, a chimeric CTLA4-immunoglobulin gene fusion can be constructed using separate template DNAs encoding CTLA4 and an immunoglobulin constant region and a "zip up" polymerase chain reaction (PCR) procedure as described in Example 1 and illustrated schematically in FIG. 1. Alternatively, a nucleic acid segment encoding CTLA4 can be ligated in-frame to a nucleic acid segment encoding an immunoglobulin constant region using standard techniques. A nucleic acid of the invention can also be chemically synthesized using standard techniques. Various methods of chemically synthesizing polydeoxynucleotides are known, including solid-phase synthesis which has been automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071, incorporated by reference herein).

The nucleic acid segments of the CTLA4-immunoglobulin gene fusions of the invention are described in further detail below:

A. CTLA4 Gene Segment

An isolated nucleic acid of the invention encodes a first peptide having a CTLA4 activity. The phrase "peptide having a CTLA4 activity" or "peptide having an activity of CTLA4" is used herein to refer to a peptide having at least one biological activity of the CTLA4 protein, i.e., the ability to bind to the natural ligand(s) of the CTLA4 antigen on immune cells, such as B7-1 and/or B7-2 on B cells, or other known or as yet undefined ligands on immune cells, and which, in soluble form, can inhibit (e.g., block) or interfere with immune cell mediated responses. In one embodiment, the CTLA4 protein is a human CTLA4 protein, the nucleotide and amino acid sequences of which are disclosed in Harper, K., et al. (1991) *J. Immunol.* 147:1037–1044 and Dariavich, et al. (1988) *Eur. J. Immunol.* 18(12):1901–1905. In another embodiment, the peptide having a CTLA4 activity binds B7-1 and/or B7-2 and comprises at least a portion of an extracellular domain of the CTLA4 protein. Preferably, the extracellular domain includes amino acid residues 1–125 of the human CTLA4 protein (amino acid positions 20–144 of SEQ ID NO: 24, 26 and 28). CTLA4 proteins from other species (e.g., mouse) are also encompassed by the invention. The nucleotide and amino acid sequences of mouse CTLA4 are disclosed in Brunet, J. F., et al., (1987) *Nature* 328:267–270.

The nucleic acids of the invention can be DNA or RNA. Nucleic acid encoding a peptide having a CTLA4 activity may be obtained from mRNA present in activated T lymphocytes. It is also possible to obtain nucleic acid encoding CTLA4 from T cell genomic DNA. For example, the gene encoding CTLA4 can be cloned from either a cDNA or a genomic library in accordance with standard protocols. A cDNA encoding CTLA4 can be obtained by isolating total mRNA from an appropriate cell line. Double stranded cDNAs can then prepared from the total mRNA. Subsequently, the cDNAs can be inserted into a suitable plasmid or bacteriophage vector using any one of a number of known techniques. Genes encoding CTLA4 can also be cloned using established polymerase chain reaction techniques in accordance with the nucleotide sequence information provided by the invention (see Example 1). For example, a DNA vector containing a CTLA4 cDNA can be used as a template in PCR reactions using oligonucleotide primers designed to amplify a desired region of the CTLA4 cDNA, e.g., the extracellular domain, to obtain an isolated DNA fragment encompassing this region using standard techniques.

It will be appreciated by those skilled in the art that various modifications and equivalents of the nucleic acids encoding the CTLA4-immunoglobulin fusion proteins of the invention exist. For example, different cell lines can be expected to yield DNA molecules having different sequences of bases. Additionally, variations may exist due to genetic polymorphisms or cell-mediated modifications of the genetic material. Furthermore, the nucleotide sequence of a CTLA4-immunoglobulin fusion protein of the invention can be modified by genetic techniques to produce proteins with altered amino acid sequences that retain the functional properties of CTLA4 (e.g., the ability to bind to B7-1 and/or B7-2). Such sequences are considered within the scope of the invention, wherein the expressed protein is capable of binding a natural ligand of CTLA4 and, when in the appropriate form (e.g., soluble) can inhibit B7: CD28/CTLA4 interactions and modulate immune responses and immune function. In addition, it will be appreciated by those of skill in the art that there are other B7-binding ligands and the fusion of these alternative molecules (such as CD28) to form immuonglobulin fusion proteins or expressed in soluble form in *E. coli* is also contemplated by the present invention.

To express a CTLA4-immunoglobulin fusion protein of the invention, the chimeric gene fusion encoding the CTLA4-immunoglobulin fusion protein typically includes a nucleotide sequence encoding a signal sequence which, upon transcription and translation of the chimeric gene, directs secretion of the fusion protein. A native CTLA4 signal sequence (e.g., the human CTLA4 signal sequence disclosed in Harper, K., et al. (1991) *J. Immunol.* 147, 1037–1044) can be used or alternatively, a heterologous signal sequence can be used. For example, the oncostatin-M signal sequence (Malik N., et al, (1989) *Mol. Cell Biol.* 9(7), 2847–2853) or an immunoglobulin signal sequence (e.g., amino acid positions 1 to 19 of SEQ ID NO: 24, 26 and 28) can be used to direct secretion of a CTLA4-immunoglobulin fusion protein of the invention. A nucleotide sequence encoding a signal sequence can be incorporated into the chimeric gene fusion by standard recombinant DNA techniques, such as by "zip up" PCR (described further in Example 1) or by ligating a nucleic acid fragment encoding the signal sequence in-frame at the 5' end of a nucleic acid fragment encoding CTLA4.

B. Immunoglobulin Gene Segment

The CTLA4-immunoglobulin fusion protein of the invention further comprises a second peptide linked to the peptide having a CTLA4 activity. In one embodiment the second peptide comprises a light chain constant region. In a preferred embodiment the light chain is a kappa light chain.

In another embodiment the second peptide comprises a heavy chain constant region. In a preferred embodiment the constant region comprises an immunoglobulin hinge region, a CH2 domain and a CH3 domain. In another embodiment the constant region also comprises a CH1 domain. The constant region is preferably derived from Cγ1, Cγ2, Cγ3 or Cγ4. In a preferred embodiment the heavy chain constant region is modified to reduce at least one constant region-mediated biological effector function. In one embodiment, the constant region segment (either Cγ1 or another isotype) is altered (e.g., mutated from the wild-type sequence at specific amino acid residues by substitution, deletion or addition of amino acid residues) to reduce at least one IgC region-mediated effector function. The effector functions of this altered fusion protein can be assessed relative to an unaltered IgC region-containing molecule (e.g., a whole antibody or Ig fusion protein). In another embodiment, a constant region other than Cγ1 that exhibits reduced IgC region-mediated effector functions is used in the fusion protein. The effector functions of this fusion protein can be assessed relative to a Cγ1-containing molecule (e.g., an IgG1 antibody or IgG1 fusion protein). In a particularly preferred embodiment, the fusion protein comprises a constant region other than Cγ1 that is also mutated to further reduce effector function. For example, a preferred IgC region is a mutated Cγ4 region.

The term "immunoglobulin constant (IgC) region-mediated biological effector function" is intended to include biological responses which require or involve, at least in part, the constant region of an immunoglobulin molecule. Examples of such effector functions include complement activation, Fc receptor interactions, opsonization and phagocytosis, antibody-dependent cellular cytotoxicity (ADCC), release of reactive oxygen intermediates and placental transfer. While such effector functions are desirable in many immune responses, they are undesirable in situations where an immune response is to be downmodulated. The CTLA4-immunoglobulin fusion proteins of the invention exhibit reduced IgC region-mediated biological effector functions and thus are efficient agents for downregulating immune responses. Additionally, the CTLA4-immunoglobulin fusion proteins of the invention display a long plasma half life in vivo. The long plasma half-life makes the proteins particularly useful as therapeutic agents.

All immunoglobulins have a common core structure of two identical light and heavy chains held together by disulfide bonds. Both the light chains and the heavy chains contain a series of repeating, homologous units, each about 110 amino acid residues in length, which fold independently in a common globular motif, called an immunoglobulin domain. In each chain, one domain (V) has a variable amino acid sequence depending on the antibody specificity of the molecule. The other domains (C) have a constant sequence common among molecules of the same isotype. Heavy chains are designated by the letter of the Greek alphabet corresponding to the overall isotype of the antibody: IgA1 contains α1 heavy chains; IgA2, α2; IgD, δ; IgE, ε; IgG1, γ1, IgG2, γ2; IgG3, γ3; IgG4, γ4; and IgM, μ. Each heavy chain includes four domains; an amino terminal variable, or VH domain which displays the greatest sequence variation among heavy chains and three domains which form the constant region (CH1, CH2 and CH3) in order from the amino to the carboxy terminus of the heavy chain. In γ, α and δ heavy chains, there is a nonglobular region of amino acid sequence, known as the hinge, located between the first and second constant region domains (CH1 and CH2) permitting motion between these two domains.

To modify a CTLA4-immunoglobulin fusion protein such that it exhibits reduced binding to the FcRI receptor, the immunoglobulin constant region segment of the CTLA4-immunoglobulin fusion protein can be mutated at particular regions necessary for Fc receptor (FcR) interactions (see Canfield, S. M. and S. L. Morrison (1991) *J. Exp. Med.* 173:1483–1491; and Lund, J. et al. (1991) *J. of immunol.* 147:2657–2662). Reduction in FcR binding ability of a CTLA4-immunoglobulin fusion protein will also reduce other effector functions which rely on FcR interactions, such as opsonization and phagocytosis and antigen-dependent cellular cytotoxicity. To reduce FcR binding, in one embodiment, the constant region is mutated within a region of the CH2 domain referred to as the "hinge link" or "lower hinge" region. This region encompasses amino acid residues 234–239 in a full-length native immunoglobulin heavy chain. It should be appreciated that all IgC region amino acid residue positions described herein refer to the position within the full-length intact native immunoglobulin heavy chain; it will be apparent to those skilled in the art that depending upon the length of the CTLA4 segment used in the CTLA4-immunoglobulin fusion protein, the positions of the corresponding IgC amino acid residues within the fusion protein will vary (Kabat, E. A, T. T. Wu, M. Reid-Miller, H. M. Perry, and K. S. Gottesman eds. (1987) "Sequences of Proteins of Immunological Interest" National Institutes of Health, Bethesda, Md.). The hinge link region can be mutated by substitution, addition or deletion of amino acid residues. A preferred CTLA4-immunoglobulin fusion protein of the invention is one in which the IgG1 constant region has substitution mutations at positions 234, 235 and/or 237 of the Cγ1 segment. Preferably, Leu at 234 is substituted with Ala, Leu at 235 is substituted with Glu and Gly at 237 is substituted with Ala (see Example 1). A preferred CTLA4-immunoglobulin fusion protein of the invention is one in which IgG4 has substitution mutations at positions 235 and/or 237 of the Cγ4 segment. Preferably, Leu at 235 is substituted with Glu and Gly at 237 is substituted with Ala (see Example 1).

In another embodiment, the Fc receptor binding capability of the CTLA4-immunoglobulin fusion protein is reduced by mutating a region of the CH2 domain referred to as the "hinge-proximal bend" region (amino acid residues at positions 328–333 within a full-length intact heavy chain). This region can be mutated by substitution, addition or deletion of amino acid residues. In a preferred embodiment, position 331 of Cγ1 or Cγ3 is mutated. A preferred mutation in Cγ1 or Cγ3 is substitution of Pro with Ser.

To modify a CTLA4-immunoglobulin fusion protein such that it exhibits reduced complement activation ability, the immunoglobulin constant region segment of the fusion protein can be mutated at particular regions important for complement activation, such as regions involved in IgC region binding to the C1q component of complement. In one embodiment, one or more residues present within the CH2 domain of IgG subclasses that are involved in C1q binding are altered. In a preferred embodiment, positions 318, 320 and/or 322 are mutated (see Duncan and Winter (1988) *Nature* 332, 738–740). Preferably, Glu at 318 is substituted with Ala or Val, Lys at 320 is substituted with Ala or Gln and/or Lys at 322 is substituted with Ala or Gln.

Alternatively, to reduce complement activation by the CTLA4-immunoglobulin fusion protein, a constant region which lacks the ability to activate complement can be used in the fusion protein. For example, it is known that both IgG1 and IgG3, but not IgG2 and IgG4 activate the classical complement cascade in the presence of human complement. Accordingly, a CTLA4-immunoglobulin fusion protein utilizing a Cγ4 constant region exhibits reduced complement activation ability relative to a CTLA4-immunoglobulin fusion protein comprising IgG1 (as demonstrated in Example 2).

In yet another embodiment, the hinge region of the IgC segment is altered to inhibit complement activation ability. The hinge regions of the human IgG molecules vary in amino acid sequence and composition as well as length. For example, IgGI, IgG2 and IgG4 have hinge regions consisting of 12 to 15 amino acids, whereas IgG3 has an extended hinge region, consisting of 62 amino acids. The hinge region is believed to be essential for binding with the first component of complement, C1q (see Tan et al. (1990) *Proc. Natl. Acad. Sci. USA* 87:162–166). A number of chimeric human IgG3 and IgG4 molecules with different hinge lengths and amino acid composition have been produced, confirming the role of the hinge region in C1q binding and complement activation. To reduce or interfere with the ability of a CTLA4-immunoglobulin (IgG1) or CTLA4-immunoglobulin (IgG3) construct to activate complement, it may be necessary to modify, by substitution, addition or deletion, at least one amino acid residue in the hinge region. In one embodiment, the hinge region of Cγ1 or Cγ3 is substituted with a hinge region derived from Cγ2 or Cγ4, each of which lack the ability to activate complement.

In addition to modifying the CTLA4-immunoglobulin fusion proteins of the invention to reduce IgC region-mediated biological effector functions, the fusion proteins can be further modified for other purposes, e.g., to increase solubility, enhance therapeutic or prophylactic efficacy, or stability (e.g., shelf life ex vivo and resistance to proteolytic degradation in vivo). Such modified proteins are considered functional equivalents of the CTLA4-immunoglobulin fusion proteins as defined herein. For example, amino acid residues of the CTLA4 portion of the fusion protein which are not essential for CTLA4 ligand interaction can be modified by being replaced by another amino acid whose incorporation may enhance, diminish, or not affect reactivity of the fusion protein. Alternatively, a CTLA4-immunoglobulin fusion protein which binds only B7-1 or B7-2 but not both could be created by mutating residues involved in binding to one ligand or the other. Another example of a modification of a CTLA4-immunoglobulin fusion protein is substitution of cysteine residues, preferably with alanine, serine, threonine, leucine or glutamic acid residues, to minimize dimerization via disulfide linkages. A particularly preferred modification is substitution of cysteine residues in the hinge region of the immunoglobulin constant region with serine. In addition, amino acid side chains of a CTLA4-immunoglobulin fusion protein can be chemically modified.

A particularly preferred embodiment of the invention features a nucleic acid encoding a CTLA4-immunoglobulin fusion protein comprising a nucleotide sequence encoding a first peptide having a CTLA4 activity and a nucleotide sequence encoding a second peptide comprising an IgG4 immunoglobulin constant region, Cγ4. Preferably, the nucleic acid is a DNA and the first peptide comprises an extracellular region of CTLA4 which binds B7-1. Such a CTLA4-IgG4 construct can comprise a nucleotide sequence show in SEQ ID NO: 25 and an amino acid sequence shown in SEQ ID NO: 26. In an even more preferred embodiment, the CH2 domain of the Cγ4 portion of this CTLA4IgG4 fusion protein is modified to reduce Fc receptor interaction. For example, the CH2 domain can be modified by substitution of Leu at position 235 (e.g., with Glu) and/or substitution of Gly at position 237 (e.g., with Ala). A particularly preferred CTLA4-IgG4 fusion protein comprises the extracellular domain of human CTLA4 (i.e., amino acid residues 1–125), has reduced Fc receptor interaction due to two substitutions in the CH2 domain (i.e., substitution of Leu at position 235 with Glu and substitution of Gly at position 237 with Ala). Such a CTLA4-IgG4 fusion protein comprises an amino acid sequence shown in SEQ ID NO: 28 and a nucleotide sequence shown in SEQ ID NO: 27. This construct, referred to as CTLA4-IgG4m, exhibits markedly reduced complement activation ability and FcR binding activity relative to a wild-type CTLA4-IgG1 construct (see Example 2).

Another preferred embodiment of the invention features a nucleic acid encoding a CTLA4-IgG1 fusion protein comprising a nucleotide sequence encoding a first peptide having a CTLA4 activity and a nucleotide sequence encoding a second peptide comprising an immunoglobulin constant region, Cγ1, which is modified to reduce at least one constant region-mediated biological effector functions. Preferably, the nucleic acid is a DNA and the first peptide comprises an extracellular region of CTLA4 which binds B7-1. To reduce Fc receptor interaction the CH2 domain of Cγ1 is modified by substitution of one or more of the following amino acid residues: Leu at position 235; Leu at position 234; and Gly at position 237. A particularly preferred CTLA4-IgG1 fusion protein comprises the extracellular domain of human CTLA4 (i.e., amino acid residues 1–125), has reduced Fc receptor interaction due to three substitutions in the CH2 domain (i.e., substitution of Leu at position 10 234 with Ala, substitution of Leu at position 235 with Glu and substitution of Gly at position 237 with Ala). Such a CTLA4-IgG1 fusion protein, referred to herein as CTLA4-IgG1m, comprises an amino acid sequence shown in SEQ ID NO: 24 and a nucleotide sequence shown in SEQ ID NO: 23.

Nucleic acid encoding a peptide comprising an immunoglobulin constant region can be obtained from human immunoglobulin mRNA present in B lymphocytes. It is also possible to obtain nucleic acid encoding an immunoglobulin constant region from B cell genomic DNA. For example, DNA encoding Cγ1 or Cγ4 can be cloned from either a cDNA or a genomic library or by polymerase chain reaction (PCR) amplification in accordance with protocols herein described. The nucleic acids of the invention can be DNA or RNA. A preferred nucleic acid encoding an immunoglobulin constant region comprises all or a portion of the following: the DNA encoding human Cγ1 (Takahashi, N. S. et al. (1982) *Cell* 29:671–679), the DNA encoding human Cγ2 (Kabat, E. A, T. T. Wu, M. Reid-Miller, H. M. Perry, and K. S. Gottesman eds. (1987) "Sequences of Proteins of Immunological Interest" National Institutes of Health, Bethesda, Md.); the DNA encoding human Cγ3 (Huck, S., et al. (1986) *Nucl. Acid Res.* 14:1779); and the DNA encoding human Cγ4 ( Kabat et al., supra).

A number of processes are known in the art for modifying a nucleotide or amino acid sequence to thereby mutate the IgC regions as described herein. For example, mutations can be introduced into a DNA by any one of a number of methods, including those for producing simple deletions or insertions, systematic deletions, insertions or substitutions of clusters of bases or substitutions of single bases, to generate CTLA4-immunoglobulin fusion proteins of the invention and equivalents thereof. Preferably, amino acid substitutions, deletions or additions, such as in the CH2 domain of the immunoglobulin constant region, are created by PCR mutagenesis as described in Example 1 or by standard site-directed mutagenesis. Site directed mutagenesis systems are well known in the art. For example, protocols and reagents can be obtained commercially from Amersham International PLC, Amersham, U.K.

II. Expression Vectors and Host Cells

The CTLA4-immunoglobulin fusion proteins of the invention can be expressed by incorporating a chimeric CTLA4-immunoglobulin fusion gene described herein into an expression vector and introducing the expression vector into an appropriate host cell. Accordingly, the invention further pertains to expression vectors containing a nucleic acid encoding a CTLA4-immunoglobulin fusion protein and to host cells into which such expression vectors have been introduced. An expression vector of the invention, as described herein, typically includes nucleotide sequences encoding the CTLA4-immunoglobulin fusion protein operably linked to at least one regulatory sequence. "Operably linked" is intended to mean that the nucleotide sequence is linked to a regulatory sequence in a manner which allows expression of the nucleotide sequence in a host cell (or by a cell extract). Regulatory sequences are art-recognized and can be selected to direct expression of the desired protein in an appropriate host cell. The term regulatory sequence is intended to include promoters, enhancers, polyadenylation signals and other expression control elements. Such regulatory sequences are known to those skilled in the art and are described in Goeddel, *Gene Expression Technology: Methods in Enzymology* 185, Academic Press, San Diego, Calif. (1990). It should be understood that the design of the expression vector may depend on such factors as the choice of the host cell to be transfected and/or the type and/or amount of protein desired to be expressed.

An expression vector of the invention can be used to transfect cells, either procaryotic or eucaryotic (e.g., mammalian, insect or yeast cells) to thereby produce fusion proteins encoded by nucleotide sequences of the vector. Expression in procaryotes is most often carried out in *E. coli* with vectors containing constitutive or inducible promoters. Certain *E. coli* expression vectors (so called fusion-vectors) are designed to add a number of amino acid residues to the expressed recombinant protein, usually to the amino terminus of the expressed protein. Such fusion vectors typically serve three purposes: 1) to increase expression of recombinant protein; 2) to increase the solubility of the target recombinant protein; and 3) to aid in the purification of the target recombinant protein by acting as a ligand in affinity purification. Examples of fusion expression vectors include pGEX (Amrad Corp., Melbourne, Australia) and pMAL (New England Biolabs, Beverly, Mass.) which fuse glutathione S-tranferase and maltose E binding protein, respectively, to the target recombinant protein. Accordingly, a chimeric CTLA4-immunoglobulin fusion gene may be linked to additional coding sequences in a procaryotic fusion vector to aid in the expression, solubility or purification of the fusion protein. Often, in fusion expression vectors, a proteolytic cleavage site is introduced at the junction of the fusion moiety and the target recombinant protein to enable separation of the target recombinant protein from the fusion moiety subsequent to purification of the fusion protein. Such enzymes, and their cognate recognition sequences, include Factor Xa, thrombin and enterokinase.

Inducible non-fusion expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from the hybrid trp-lac fusion promoter. Target gene expression from the pET 11d vector relies on transcription from the T7 gn10-lac 0 fusion promoter mediated by a coexpressed viral RNA polymerase (T7 gn1). This viral polymerase is supplied by host strains BL21(DE3) or HMS174(DE3) from a resident λ prophage harboring a T7 gn1 under the transcriptional control of the lacUV 5 promoter.

One trategy to maximize expression of recombinant CTLA4-immunoglobulin fusion protein in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy would be to alter the nucleotide sequence of the CTLA4-immunoglobulin fusion protein to be inserted into an expression vector so that the individual codons for each amino acid would be those preferentially utilized in highly expressed *E. coli* proteins (Wada et al., (1992) *Nuc. Acids Res.* 20:2111–2118). Such alteration of nucleic acid sequences are encompassed by the invention and can be carried out by standard DNA synthesis techniques.

In another preferred embodiment a soluble CTLA4 extracellular domain is expressed in *E coli* using an appropriate expression vector. These forms, although not glycosylated, remain fully functional and represent an advantage because of the ease with which hacterial cells are grown.

Alternatively, a CTLA4-immunoglobulin fusion protein can be expressed in a eucaryotic host cell, such as mammalian cells (e.g., Chinese hamster ovary cells (CHO) or NSO cells), insect cells (e.g., using a baculovirus vector) or yeast cells. Other suitable host cells may be found in Goeddel, (1990) supra or are known to those skilled in the art. Eucaryotic, rather than procaryotic, expression of a CTLA4-immunoglobulin fusion protein may be preferable since expression of eucaryotic proteins in eucaryotic cells can lead to partial or complete glycosylation and/or formation of relevant inter- or intra-chain disulfide bonds of a recombinant protein. For expression in mammalian cells, the expression vector's control functions are often provided by viral material. For example, commonly used promoters are derived from polyoma, Adenovirus 2, cytomegalovirus and Simian Virus 40. To express a CTLA4-immunoglobulin fusion protein in mammalian cells, generally COS cells (Gluzman, Y., (1981) *Cell* 23:175–182) are used in conjunction with such vectors as pCDM8 (Seed, B., (1987) *Nature* 329:840) for transient amplification/expression, while CHO (dhfr⁻ Chinese Hamster Ovary) cells are used with vectors such as pMT2PC (Kaufman et al. (1987), *EMBO J.* 6:187–195) for stable amplification/expression in mammalian cells. A preferred cell line for production of recombinant protein is the NSO myeloma cell line available from the ECACC (catalog #85110503) and described in Galfre, G. and Milstein, C. ((1 981) *Methods in Enzymology* 73(13) :3–46; and *Preparation of Monoclonal Antibodies:*

Strategies and Procedures, Academic Press, N.Y., N.Y). Examples of vectors suitable for expression of recombinant proteins in yeast (e.g., *S. cerivisae*) include pYepSec1 (Baldari. et al., (1987) *Embo J.* 6:229–234), pMFa (Kurjan and Herskowitz, (1982) *Cell* 30:933–943), pJRY88 (Schultz et al., (1987) *Gene* 54:113–123), and pYES2 (Invitrogen Corporation, San Diego, Calif.). Baculovirus vectors available for expression of proteins in cultured insect cells (SF 9 cells) include the pAc series (Smith et al., (1983) *Mol. Cell Biol.* 3:2156–2165) and the pVL series (Lucklow, V. A., and Summers, M. D., (1989) *Virology* 170:31–39).

Vector DNA can be introduced into procaryotic or eucaryotic cells via conventional transformation or transfection techniques such as calcium phosphate or calcium choloride co-precipitation, DEAE-dextran-mediated transfection, lipofection, or electroporation. Suitable methods for transforming host cells can be found in Sambrook et al. (*Molecular Cloning: A Laboratory Manual*, 2nd Edition, Cold Spring Harbor Laboratory press (1989)), and other laboratory textbooks.

For stable transfection of mammalian cells, it is known that, depending upon the expression vector and transfection technique used, only a small faction of cells may integrate DNA into their genomes. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker may be introduced into a host cell on the same plasmid as the gene of interest or may be introduced on a separate plasmid. Cells containing the gene of interest can be identified by drug selection (e.g., cells that have incorporated the selectable marker gene will survive, while the other cells die). The surviving cells can then be screened for production of CTLA4-immunoglobulin fusion proteins by, for example, immunoprecipitation from cell supernatant with an anti-CTLA4 monoclonal antibody.

The invention also features methods of producing CTLA4-immunoglobulin fusion proteins. For example, a host cell transfected with a nucleic acid vector directing expression of a nucleotide sequence encoding a CTLA4-immunoglobulin fusion protein can be cultured in a medium under appropriate conditions to allow expression of the protein to occur. In one embodiment, a recombinant expression vector containing DNA encoding a CTLA4-IgG1 fusion protein having modified constant region-mediated effector functions is produced. In another embodiment, a recombinant expression vector containing DNA encoding a CTLA4-IgG4 fusion protein having modified constant region-mediated effector functions is produced. In addition, one or more expression vectors containing DNA encoding, for example, a CTLA4-IgG1 fusion protein and another fusion protein such as a CTLA4-IgG4 fusion protein can be used to transfect a host cell to coexpress these fusion proteins. Fusion proteins produced by recombinant technique may be secreted and isolated from a mixture of cells and medium containing the protein. Alternatively, the protein may be retained cytoplasmically and the cells harvested, lysed and the protein isolated. A cell culture typically includes host cells, media and other byproducts. Suitable mediums for cell culture are well known in the art. Protein can be isolated from cell culture medium, host cells, or both using techniques known in the art for purifying proteins.

III. Isolation and Characterization of CTLA4-immunoglobulin Fusion Proteins Another aspect of the invention pertains to CTLA4-immunoglobulin fusion proteins having modified effector functions compared to a CTLA4-IgG1 protein. Such proteins comprise a first peptide having a CTLA4 activity and a second peptide comprising an immunoglobulin constant region which is modified to reduce at least one constant region-mediated biological effector function relative to a CTLA4-IgG1 fusion protein. A peptide having a CTLA4 activity has been previously defined herein. In a preferred embodiment, the first peptide comprises an extracellular domain of the human CTLA4 protein (e.g., amino acid residues 20–144 of SEQ ID NO: 24, 26 and 28) and binds B7-1 and/or B7-2. The second peptide comprising an immunoglobulin constant region preferably includes a hinge region, a CH2 domain and a CH3 domain derived from Cγ1, Cγ2, Cγ3, or Cγ4. Typically, the CH2 domain is modified to reduce constant region-mediated biological effector functions, such as complement activation and/or Fc receptor interaction as previously described in detail herein.

Another embodiment of the invention provides a substantially pure preparation of a CTLA4-immunoglobulin fusion protein as described herein. Such a preparation is substantially free of proteins and peptides with which the protein naturally occurs in a cell or with which it naturally occurs when secreted by a cell.

CTLA4-immunoglobulin fusion proteins, expressed in mammalian cells or elsewhere, can be purified according to standard procedures of the art, including ammonium sulfate precipitation, fractionation column chromatography (e.g., ion exchange, gel filtration, electrophoresis, affinity chromatography, etc.) and ultimately, crystallization (see generally, "Enzyme Purification and Related Techniques", Methods in Enzymology, 22:233–577 (1971)). Preferably, the CTLA4-immunoglobulin fusion proteins are purified using an immobilized protein A column (Repligen Corporation, Cambridge, Mass.). Once purified, partially or to homogeneity, the recombinantly produced CTLA4-immunoglobulin fusion proteins or portions thereof can be utilized in compositions suitable for pharmaceutical administration as described in detail herein.

In one embodiment the CTLA4-immunoglobulin fusion protein is an antibody form in which the heavy and light chains have been replaced with the extracellular domain of CTLA4. This molecule has a different valency and higher affinity for CTLA4 ligands, thus making it possible to obtain similar results while using less of the agent. The fact that this molecule has a true antibody tail which is fully glycosylated means that numerous cell lines for producing the CTLA4Ab fusion protein and data regarding the clinical use of antibodies may be relied on.

Screening of CTLA4-immunoglobulin fusion proteins which have been modified to reduce at least one constant region-mediated biological effector function as described herein can be accomplished using one or more of several different assays which measure different effector functions. For example, to identify a CTLA4-immunoglobulin fusion protein having reduced Fc receptor interaction, a monomeric IgG binding assay can be conducted (see Example 2). A cell which expresses an Fc receptor, such as a mononuclear phagocyte or the U937 cell line (FcγRI expression), a hematopoietic cell (FcγRII expression; Rosenfeld, S. I., et al. (1985) J. Clin. Invest. 76:2317–2322) or a neutrophil (FcγRIII expression; Fleit, H. B., et al. (1982) Proc. Natl. Acad. Sci. USA 79:3275–3279 and Petroni, K.C., et al. (1988) J. Immunol. 140:3467–3472) is contacted with, for example, $^{125}$I-labeled immunoglobulin of the IgG1 isotype in the presence or absence of a modified CTLA4-immunoglobulin fusion protein of the invention and in the presence or absence of an appropriate control molecule (e.g., an unlabeled IgG1 antibody or a CTLA4-IgG1 fusion protein). The amount of $^{125}$I-labeled IgG1 bound to the cells and/or the amount of free $^{125}$I-labeled IgG in the supernatant is determined. A CTLA4-immunoglobulin fusion protein having reduced Fc receptor binding is identified by a reduced ability (or lack of ability) to inhibit binding of the $^{125}$I-labeled IgG1 to the cells (relative to the control molecule). Monomeric IgG binding assay are described further in Lund, J., et al. (1991) J. Immunol. 147:2657–2662; and Woof, J. M., et al. (1986) Mol. Immunol. 23:319.

To identify a CTLA4-immunoglobulin fusion protein with a reduced ability to activate the complement cascade, a complement activation assay such as that described in Example 2 can be used. In this assay, a cell which expresses a CTLA4 ligand (e.g., B7-1 or B7-2) on its surface is loaded with a detectable substance, e.g., a fluorescent dye, and then contacted with the CTLA4-immunoglobulin fusion protein and a complement source (e.g., purified guinea pig complement or human serum as a source of human complement). Cell lysis, as determined by release of the fluorescent dye from the cells, is determined as an indication of activation of the complement cascade upon binding of CTLA4-immunoglobulin to the CTLA4 ligand on the cell surface. Cells which do not express a CTLA4 ligand on their surface are used as a negative control. A CTLA4-immunoglobulin fusion protein with reduced ability (or lack of the ability) to activate complement relative to an appropriate control molecule (e.g., anti-B7-1 antibody of the IgG1 isotype or a CTLA4-IgG1 fusion protein) is identified by a reduction in or absence of cell lysis of labeled, CTLA4 ligand positive cells when incubated in the presence of the CTLA4-immunoglobulin fusion protein of the invention and complement compared to cells incubated in the presence of the control molecule and complement.

In another complement activation assay, the ability of a CTLA4-immunoglobulin fusion protein to bind the first component of the complement cascade, C1q, is assessed. For example, C1q binding can be determined using a solid phase assay in which $^{125}$I-labeled human C1q is added to an amount of CTLA4-immunoglobulin fusion protein complexed with a CTLA4 ligand, such as B7-1 or B7-2, and the amount of bound $^{125}$I-labeled human C1q quantitated. A CTLA4-immunoglobulin fusion protein having a reduced complement activation activity (or lack of complement activation activity) is identified by a reduction in or absence of the ability to bind the $^{125}$I-labeled human C1q relative to an appropriate control molecule (e.g., an IgG1 antibody or a CTLA4-IgG1 fusion protein). C1q binding assays are described further in Tan. L. K., et al. (1990) *Proc. Natl. Acad. Sci. USA* 87:162–166; and Duncan, A. R. and G. Winter (1988) *Nature* 332:738–740.

Additional assays for other immunoglobulin constant region-mediated effector functions, such as opsonization and phagocytosis, antibody-dependent cellular cytotoxicity and release of reactive oxygen intermediates, have been described in the art and are known to the skilled artisan.

Screening for CTLA4-immunoglobulin fusion proteins which have a CTLA4 activity as described herein can be accomplished using one or more of several different assays. For example, the fusion proteins can be screened for specific reactivity with an anti-CTLA4 antibody (e.g., a monoclonal or polyclonal anti-CTLA4 antibody) or with a soluble fonn of a CTLA4 ligand, such as a B7-1 or B7-2 fusion protein (e.g., B7-1Ig or B7-2Ig). For exa appropriate cells, such as CHO or NS0cells, can be transfected with a DNA encoding a CTLA4-immunoglobulin fusion protein and the cell supernatant analyzed for expression of the resulting fusion protein using an anti-CTLA4 monoclonal antibody or B7-1Ig or B7-2Ig fusion protein in a standard immunoprecipitation assay. Alternatively, the binding of a CTLA4-immunoglobulin fusion protein to a cell which expresses a CTLA4 ligand, such as a B7-1 or B7-2, on its surface can be assessed. For example, a cell expressing a CTLA4 ligand, such as a CHO cell transfected to express B7-1, is contacted with the CTLA4-immunoglobulin fusion protein and binding detected by indirect immunostaining using, for example, a FITC-conjugated reagent (e.g., goat anti-mouse Ig serum for murine monoclonal antibodies or goat anti-human IgCy serum for fusion proteins) and fluorescence analyzed by FACS® analysis(Becton Dickinson & Co., Mountain View, Calif.).

Other suitable assays take advantage of the functional characteristics of the CTLA4-immunoglobulin fusion protein. As previously set forth, the ability of T cells to synthesize cytokines depends not only on occupancy or cross-linking of the T cell receptor for antigen ("the primary activation signal provided by, for example antigen bound to an MHC molecule, anti-CD3, or phorbol ester to produce an "activated T cell"), but also on the induction of a costimulatory signal, in this case, by interaction of a B7 family protein (e.g., B7-1 or B7-2) with its ligand (CD28 and/or CTLA4) on the surface of T cells. The B7: CD28/CTLA4 interaction has the effect of transmitting a signal to the T cell that induces the production of increased levels of cytokines, particularly of interleukin-2, which in turn stimulates the proliferation of the T lymphocytes. In one embodiment, the CTLA4-immunoglobulin fusion proteins of the invention have the functional property of being able to inhibit the B7: CD28/CTLA4 interaction. Accordingly, other screening assays for identifying a functional CTLA4-immunoglobulin fusion protein involve assaying for the ability of the fusion protein to inhibit synthesis of cytokines, such as interleukin-2, interleukin-4 or other known or unknown novel cytokines and/or the ability to inhibit T cell proliferation by T cells which have received a primary activation signal.

The ability of a CTLA4-immunoglobulin fusion protein of the invention to inhibit or block an interaction between a B7 family protein (e.g., B7-1 or B7-2) with its receptor on T cells (e.g., CD28 and/or CTLA4) can be assessed in an in vitro T cell culture system by stimulating T cells with a source of ligand (e.g., cells expressing B7-1 and/or B7-2 or a secreted form of B7-1 and/or B7-2) and a primary activation signal such as antigen in association with Class II MHC (or alternatively, anti-CD3 antibodies or phorbol ester) in the presence or absence of the CTLA4-immunoglobulin fusion protein. The culture supernatant is then assayed for cytokine production, such as interleukin-2, gamma interferon, or other known or unknown cytokine. For example, any one of several conventional assays for interleukin-2 can be employed, such as the assay described in *Proc. Natl. Acad. Sci. USA*, 86:1333 (1989). An assay kit for interferon production is also available from Genzyme Corporation (Cambridge, Mass.). T cell proliferation can be measured in vitro by determining the amount of $^3$H-labeled thymidine incorporated into the replicating DNA of cultured cells. The rate and amount of DNA synthesis and, in turn, the rate of cell division can thus be quantified. A lack of or reduction in the amount of cytokine production and/or T cell proliferation by stimulated T cells upon culture with a CTLA4-immunoglobulin fusion protein of the invention indicates that the fusion protein is capable of inhibiting the delivery of a costimulatory signal to the T cell by inhibiting an interaction between a CTLA4 ligand (e.g., B7-1 and/or B7-2) and a receptor therefor (e.g., CD28 and/or CTLA4).

The ability of the CTLAIg fusion protein to induce antigen-specific T cell unresponsiveness or anergy can also be assessed using the in vitro T cell culture system described above. Following stimulation of the T cells with a specific antigen bound to MHC molecules on an antigen presenting cell surface and CTLA4 ligand (e.g., B7-1 on the antigen presenting cell surface) in the presence of CTLA4-immunoglobulin fusion protein, the T cells are subsequently restimulated with the antigen in the absence of CTLA4-immunoglobulin fusion protein. A lack of cytokine production and/or T cell proliferation upon antigenic restimulation by T cells previously treated with a CTLA4-immunoglobulin fusion protein of the invention indicates that the fusion protein has induced a state of antigen-specific anergy or non-responsiveness in the T cells. See, e.g., Gimmi, C. D. et al. (1993) *Proc. Natl. Acad. Sci. USA* 90:6586–6590; and Schwartz (1990) *Science* 248:1349–1356, for assay systems that can used to examine T cell unresponsiveness in accordance with the present invention.

In yet another assay, the ability of a CTLA4-immunoglobulin fusion protein of the invention to inhibit T cell dependent immune responses in vitro is determined. The effect of a CTLA4-immunoglobulin fusion protein on Th-induced immunoglobulin production by B cells can be assessed by contacting antigen-specific CD4+T cells with syngeneic antigen-specific B cells, antigen and the CTLA4-immunoglobulin fusion protein. The cell culture supernatant is assayed for the production of immunoglobulin, such as IgG or IgM, using, for example, a solid phase ELISA or a standard plaque assay. Inhibition of B cell immunoglobulin production by treatment of the culture with the CTLA4-immunoglobulin fusion protein indicates that the protein is capable inhibiting T helper cell responses and, consequently, T cell dependent B cell responses.

IV. Compositions of CTLA4-immunolobulin Fusion Proteins

The CTLA4-immunoglobulin fusion proteins of the invention can be incorporated into compositions suitable for administration to subjects to thereby modulate immune responses or for other purposes (e.g., antibody production). The CTLA4-immunoglobulin fusion protein in such compositions is in a biologically compatible form suitable for pharmaceutical administration in vivo. By "biologically compatible form suitable for administration in vivo" is meant a form of the protein to be administered in which any toxic effects are outweighed by the therapeutic effects of the protein. The term subject is intended to include living organisms in which an immune response can be elicited, e.g., mammals. Examples of subjects include humans, monkeys, dogs, cats, mice, rats, and transgenic species thereof. Administration of a CTLA4-immunoglobulin fusion protein as described herein can be in any pharmacological form including a therapeutically active amount of protein and a pharmaceutically acceptable carrier. Administration of a therapeutically active amount of the therapeutic compositions of the invention is defined as an amount effective, at dosages and for periods of time necessary to achieve the desired result. For example, a therapeutically active amount of a CTLA4-immunoglobulin fusion protein may vary according to factors such as the disease state, age, sex, and weight of the individual, and the ability of protein to elicit a desired response in the individual. Dosage regima may be adjusted to provide the optimum therapeutic response. For example, several divided doses may be administered daily or the dose may be proportionally reduced as indicated by the exigencies of the therapeutic situation.

The active compound (e.g., CTLA4-immunoglobulin fusion protein) may be administered in a convenient manner such as by injection (subcutaneous, intravenous, etc.), oral administration, inhalation, transdermal application, or rectal administration. Depending on the route of administration, the active compound may be coated in a material to protect the compound from the action of enzymes, acids and other natural conditions which may inactivate the compound.

To administer a CTLA4-immunoglobulin fusion protein by other than parenteral administration, it may be necessary to coat the protein with, or co-administer the protein with, a material to prevent its inactivation. For example, a CTLA4-immunoglobulin fusion protein may be administered to an individual in an appropriate carrier, diluent or adjuvant, co-administered with enzyme inhibitors or in an appropriate carrier such as liposomes. Pharmaceutically acceptable diluents include saline and aqueous buffer solutions. Adjuvant is used in its broadest sense and includes any immune stimulating compound, such as interferon. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEP) and trasylol. Liposomes include water-in-oil-in-water emulsions as well as conventional liposomes (Strejan et al., (1984) *J. Neuroimmunol* 7:27).

The active compound may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., CTLA4-immunoglobulin fusion protein) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (e.g., peptide) plus any additional desired ingredient from a previously sterile-filtered solution thereof.

When the active compound is suitably protected, as described above, the protein may be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

V. Uses of CTLA4-immunoglobulin Fusion Proteins Having Reduced IgC Region-Mediated Biological Effector Functions A. Immunomodulation Given the role of CTLA4 ligands, such as B7-1 and B7-2, in T cell costimulation and the structure and function of the CTLA4-immunoglobulin fusion proteins disclosed herein, the invention provides methods for downregulating immune responses. The reduced IgC-region mediated biological effector functions exhibited by the mutated CTLA4-immunoglobulin fusion proteins of the invention compared to a CTLA4-IgG1 fusion protein may result in more effective downregulation of immune responses in vivo without unwanted side effects (e.g., complement activation, antibody-dependent cellular cytotoxicity, etc.) than if a CTLA4-IgG1 fusion protein were used. For example, improvements in mutated forms of CTLA4-immunoglobulin fusion proteins can be assessed by a variety of assays known to hose skilled in the art, including various animal organ (heart, liver, kidney, bone marrow) transplantation models and in animal autoimmune disease models including, but not limited to lupus, multiple sclerosis, diabetes, and arthritis models.

Downregulation of an immune response by a CTLA4-immunoglobulin fusion protein of the invention may be in the form of inhibiting or blocking an immune response already in progress or may involve preventing the induction of an immune response. The functions of activated T cells, such as T cell proliferation and cytokine (e.g., IL-2) secretion, may be inhibited by suppressing T cell responses or by inducing specific tolerance in T cells, or both. Immunosuppression of T cell responses is generally an active process which requires continuous exposure of the T cells to the suppressive agent and is often not antigen-specific. Tolerance, which involves inducing non-responsiveness or anergy in T cells, is distinguishable from immunosuppression in that it is generally antigen-specific and persists after exposure to the tolerizing agent has ceased. Operationally, T cell unresponsiveness or anergy can be demonstrated by the lack of a T cell response upon reexposure to specific antigen in the absence of the tolerizing agent. Immunosuppression and/or T cell unresponsiveness is achieved by blocking the interaction of a CTLA4 ligand on an antigen presenting cell with CTLA4 itself and/or with another receptor for the CTLA4 ligand (e.g., CD28) on the surface of a T cell, e.g., blocking the interaction of a B7 family protein, such as B7-1 and/or B7-2, with a counter-receptor, such as CD28 or CTLA4, on the surface of a T cell. The term "antigen presenting cell" is intended to include B lymphocytes, professional antigen presenting cells (e.g., monocytes, dendritic cells, Langerhan cells) and others cells (e.g., keratinocytes, endothelial cells, astrocytes, fibroblasts, oligodendrocytes) which can present antigen to T cells. The CTLA4-immunoglobulin fusion proteins of the invention can be used to inhibit CTLA4 ligand/receptor interactions in many clinical situations, as described further below.

1. Organ Transplantation/GVHD:

Inhibition of T cell responses by a CTLA4-immunoglobulin fusion protein of the invention is useful in situations of cellular, tissue, skin and organ transplantation and in bone marrow transplantation (e.g., to inhibit graft-versus-host disease (GVHD)). For example, inhibition of T cell proliferation and/or cytokine secretion may result in reduced tissue destruction in tissue transplantation and induction of antigen-specific T cell unresponsivenesg may result in long-term graft acceptance without the need for generalized immunosuppression. Typically, in tissue transplants, rejection of the graft is initiated through its recognition as foreign by T cells, followed by an immune reaction that destroys the graft. Administration of a CTLA4-immunoglobulin fusion protein of the invention to a transplant recipient inhibits triggering of a costimulatory signal in alloantigen-specific T cells, thereby inhibiting T cell responses to alloantigens and, moreover, may induce graft-specific T cell unresponsiveness in the recipient. The transplant recipient can be treated with the CTLA4-immunoglobulin fusion protein alone or together with one or more additional agents that inhibit the generation of stimulatory signals in the T cells (e.g., anti-B7-1 and/or anti-B7-2 antibodies, an anti-IL-2 receptor antibody) or induce general immunosuppression (e.g., cyclosporin A or FK506).

Use of a CTLA4-immunoglobulin fusion protein to inhibit triggering of a costimulatory signal in T cells can similarly be applied to the situation of bone marrow transplantation to specifically inhibit the responses of alloreactive T cells present in donor bone marrow and thus inhibit GVHD. A CTLA4-immunoglobulin fusion protein can be administered to a bone marrow transplant recipient to inhibit the alloreactivity of donor T cells. Additionally or alternatively, donor T cells within the bone marrow graft can be tolerized to recipient alloantigens ex vivo prior to transplantation. For example, donor bone marrow can be cultured with cells from the recipient (e.g., irradiated hematopoietic cells) in the presence of a CTLA4-immunoglobulin fusion protein of the invention prior to transplantation. Additional agents that inhibit the generation of stimulatory signals in the T cells (e.g., anti-B7-1 and/or anti-B7-2 antibodies, an anti-IL-2R antibody etc., as described above) can be included in the culture. After transplantation, the recipient may be further treated by in vivo administration of CTLA4-immunoglobulin (alone or together with another agent(s) which inhibits the generation of a costimulatory signal in T cells in the recipient or inhibits the production or function of a T cell growth factor(s) (e.g., IL-2) in the recipient).

The efficacy of a particular CTLA4-immunoglobulin fusion protein in inhibiting organ transplant rejection or GVHD can be assessed using animal models that may be predictive of efficacy in humans. Given the homology between CTLA4 molecules of different species, the functionally important aspects of CTLA4 are believed to be conserved structurally among species thus allowing animal systems to be used as models for efficacy in humans. Examples of appropriate systems which can be used include allogeneic cardiac grafts in rats and xenogeneic pancreatic islet cell grafts in mice, both of which have been used to examine the immunosuppressive effects of CTLA4-IgG1 fusion proteins in vivo as described in Lenschow et al., *Science*, 257: 789–792 (1992) and Turka et al., *Proc. Natl. Acad. Sci. USA*, 89: 11102–11105 (1992). In addition, murine models of GVHD (see Paul ed., *Fundamental Immunology*, Raven Press, New York, 1989, pp. 846–847) can be used to determine the effect of treatment with a CTLA4-immunoglobulin fusion protein of the invention on the development of that disease.

As an illustrative embodiment, a CTLA4-immunoglobulin fusion protein of the invention can be used in a rat model of organ transplantation to ascertain the ability of the fusion protein to inhibit alloantigen responses in vivo. Recipient Lewis rats receive a Brown-Norway rat strain cardiac allograft which is anastamosed to vessels in the neck as described in Bolling, S. F. et al., *Transplant*. 453:283–286 (1992). Grafts are monitored for mechanical function by palpation and for electrophysiologic function by electrocardiogram. Graft rejection is said to occur on the last day of palpable contractile function. As an initial test, animals are treated with daily injections of a CTLA4-immunoglobulin fusion protein of interest, an isotype-matched control Ig fusion protein and/or CTLA4-IgG1 (for comparison purposes) for 7 days. Fusion proteins are administered at a dosage range between approximately 0.015 mg/day and 0.5 mg/day. Untreated Lewis rats typically reject heterotopic Brown-Norway allografts in about 7 days. The rejection of allografts by fusion protein-treated animals is assessed in comparison to untreated controls.

An untreated animal and a fusion protein-treated animal are sacrificed for histological examination. Cardiac allografts are removed from the untreated animal and the treated animal four days after transplantation. Allografts are fixed in formalin, and tissue sections are stained with hematoxylin-eosin. The heart tissue of the untreated and treated animals is examined histologically for severe acute cellular rejection including a prominent interstitial mononuclear cell infiltrate with edema formation, myocyte destruction, and infiltration of arterlolar walls. The effectiveness of the fusion protein treatment in inhibiting graft rejection is supported by a lack of an acute cellular rejection in the heart tissue of the fusion protein treated animals.

To determine whether fusion protein therapy establishes long term graft acceptance that persists following treatment, animals treated for 7 days with daily injections of fusion protein are observed without additional therapy until cessation of graft function. Graft survival is assessed daily as described above. Allografts are examined histologically from animals in which the graft stops functioning as described above. Induction of graft tolerance by fusion protein treatment is indicated by the continued functioning of the graft following the cessation of treatment with the fusion protein.

After prolonged graft acceptance, a fusion protein-treated animal can be sacrificed and the lymphocytes from the recipient can be tested for their functional responses. These responses are compared with those of lymphocytes from a control (non-transplanted) Lewis rat, and results are normalized as a percentage of the control response. The T cell proliferative response to ConA and to cells from a Brown-Norway rat and a third party ACI rat can be examined. Additionally, the thymus and spleen from the untreated and treated animals can be compared in size, cell number and cell type (e.g. by flow cytometic analyses of thymus, lymph nodes and spleen cells). Specific nonresponsiveness in the treated animals to alloantigens, as a result of specific clonal deletion of alloreactive cells, is indicated by the ability of the T cells to respond to ConA and third party stimulators (e.g., ACI rat cells) but not to Brown-Norway rat cells. Prolonged acceptance of allografts, including continued graft acceptance following CTLA4-immunoglobulin treatment, in this model system may be predictive of the therapeutic efficacy of the CTLA4-immunoglobulin fusion proteins of the invention in human transplant situations.

2. Autoimmune Diseases:

Inhibition of T cell responses by a CTLA4-immunoglobulin fusion protein of the invention may also be therapeutically useful for treating autoimmune diseases. Many autoimmune disorders are the result of inappropriate activation of T cells that are reactive against self tissue (i.e., reactive against autoantigens) and which promote the production of cytokines and autoantibodies involved in the pathology of the diseases. Preventing the activation of autoreactive T cells thus may reduce or eliminate disease symptoms. Administration of a CTLA4-immunoglobulin fusion protein of the invention to a subject suffering from or susceptible to an autoimmune disorder may inhibit autoantigen-specific T cell responses and induce autoantigen-specific T cell unresponsiveness, thereby inhibiting or preventing production of autoantibodies or T cell-derived cytokines which may be involved in the disease process.

To treat an autoimmune disorder, a CTLA4-immunoglobulin fusion protein of the invention is administered to a subject in need of treatment. For autoimmune disorders with a known autoantigen, it may be desirable to coadminister the autoantigen with the CTLA4-immunoglobulin to the subject. This method can be used to treat a variety of autoimmune diseases and disorders having an autoimmune component, including diabetes mellitus, arthritis (including rheumatoid arthritis, juvenile rheumatoid arthritis, osteoarthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjögren's Syndrome, including keratoconjunctivitis sicca secondary to Sjögren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves ophthalmopathy, sarcoidosis, primary biliary cirrhosis, uveitis posterior, and interstitial lung fibrosis.

The efficacy of a CTLA4-immunoglobulin fusion protein of the invention in preventing or alleviating autoimmune disorders can be determined using a number of well-characterized animal models of human autoimmune diseases. Examples include murine experimental autoimmune encephalitis, systemic lupus erythmatosis in MRL/lpr/lpr mice or NZB hybrid mice, murine autoimmune collagen arthritis, diabetes mellitus in NOD mice and BB rats, and murine experimental myasthenia gravis (see Paul ed., *Fundamental Immunology*, Raven Press, New York, 1989, pp. 840–856).

Experimental Autoimmune Encephalomyelitis (EAE) is a rodent and primate model for multiple sclerosis. In an illustrative embodiment utilizing the passive EAE model, donor mice are immunized with 0.4 mg Myelin Basic Protein (MBP) in Complete Freund's Adjuvant (CFA), divided over four quadrants. The draining axillary and inguinal lymph nodes are removed eleven days later. Lymph node cells ($4 \times 10^6$/ml) are plated in 2 ml cultures in 24 well plates, in the presence of 25 µg/ml MBP. After four days in culture, $30 \times 10^6$ of the treated cells are injected into the tail vein of each naive, syngeneic recipient mouse.

The recipient mice develop a remitting, relapsing disease and are evaluated utilizing the following criteria:

0 normal, healthy
1 limp tail, incontinence; occasionally the first sign of the disease is a "tilt"
2 hind limb weakness, clumsiness
3 mild paraparesis
4 severe paraparesis
5 quadriplegia
6 death Using the passive model of EAE, the effect of CTLA4-immunoglobulin treatment of the donor cells on resulting disease severity in a recipient animal is tested in mice (e.g., the PLSJLF1/J strain). Culture of lymph node cells in vitro with MBP is performed either in the presence or the absence of about 30 μg/ml of a CTLA4-immunoglobulin fusion protein of the invention, an isotype matched control Ig fusion protein or CTLA4IgG1 (for comparison purposes). The treated cells are then introduced into a syngeneic recipient mouse. The effect of fusion protein treatment of donor cells on the severity of the recipient's first episode of disease as compared to mice receiving untreated cells can be determined using the above-described criteria to assess disease severity. In addition, ensuing relapses in the mice receiving fusion protein-treated cells versus untreated cells can be assessed using the above-described criteria.

The effect of treating both the donor mice and the cultured donor cells with CTLA4-immunoglobulin on the clinical disease severity in the recipient can further be assessed. In these experiments, donor mice (e.g., of the SJL/J strain) immunized with MBP are given either 100 μg of CTLA4-immunoglobulin fusion protein, an isotype matched control Ig fusion protein or CTLA4-IgG1 (for comparison) intraperitoneally each day for eleven days.

Cells are then isolated from lymph nodes of these donors and cultured with MBP in vitro in the presence of either 30 μg/ml of CTLA4-immunoglobulin fusion protein or control fusion proteins. The treated cells are then introduced into a syngeneic recipient. The effect of fusion protein treatment on the severity of the ensuing disease in the recipient is then assessed using the above-described criteria.

Studies using a direct (active) model of EAE can also conducted. In these experiments, a CTLA4-immunoglobulin fusion protein of the invention or control fusion protein is directly administered to mice immunized with MBP and treated with pertussis toxin (PT). Mice (e.g., the PLSJLFI/J strain) are immunized with MBP on day 0, injected with PT intravenously on days 0 and 2, and given either a CTLA4-immunoglobulin fusion protein of the invention or a control fusion protein on days 0 to 7. The effect of direct fusion protein treatment of the MBP-immunized mice on the severity of the ensuing disease is then assessed using the above-described criteria. A reduced severity in disease symptoms in the passive and/or active EAE model as a result of CTLA4-immunoglobulin treatment may be predictive of the therapeutic efficacy of the CTLA4-immunoglobulin fusion proteins of the invention in human autoimmune diseases.

3. Allergy:

The IgE antibody response in atopic allergy is highly T cell dependent and, thus, inhibition of CTLA4 ligand/receptor induced T cell activation may be useful therapeutically in the treatment of allergy and allergic reactions. A CTLA4-immunoglobulin fusion protein of the invention can be administered to an allergic subject to inhibit T cell mediated allergic responses in the subject. Inhibition of costimulation of T cells through inhibition of a CTLA4 ligand/receptor interaction may be accompanied by exposure to allergen in conjunction with appropriate MHC molecules. Exposure to the allergen may be environmental or may involve administering the allergen to the subject. Allergic reactions may be systemic or local in nature, depending on the route of entry of the allergen and the pattern of deposition of IgE on mast cells or basophils. Thus, it may be necessary to inhibit T cell mediated allergic responses locally or systemically by proper administration of a CTLA4-immunoglobulin fusion protein of the invention. For example, in one embodiment, a CTLA4-immunoglobulin fusion protein of the invention and an allergen are coadminstered subcutaneously to an allergic subject.

4. Virally Infected or Malignant T Cells:

Inhibition of T cell activation through blockage of the interaction of a CTLA4 ligand with a receptor therefor on T cells may also be important therapeutically in viral infections of T cells. For example, in the acquired immune deficiency syndrome (AIDS), viral replication is stimulated by T cell activation. Blocking a CTLA4 ligand/receptor interaction, such as the interaction of B7-1 and/or B7-2 with CD28 and/or CTLA4 could lead to a lower level of viral replication and thereby ameliorate the course of AIDS. Surprisingly, HTLV-I infected T cells express B7-1 and B7-2. This expression may be important in the growth of HTLV-I infected T cells and the blockage of B7-1 function together with the function of B7-2 with a CTLA4-immunoglobulin fusion protein, possibly in conjunction with another blocking reagent (such as an anti-B7-2 blocking antibody or a CD28Ig fusion protein) may slow the growth of HTLV-I induced leukemias. In addition, some tumor cells are responsive to cytokines and the inhibition of T cell activation and cytokine production could help to inhibit the growth of these types of cancer cells.

5. Antigen-Specific T Cell Unresponsiveness:

The methods of the invention for inhibiting T cell responses can essentially be applied to any antigen (e.g., protein) to clonally delete T cells responsive to that antigen in a subject. For example, in one study, administration of a CTLA4-IgG1 fusion protein to mice in vivo suppressed primary and secondary T cell-dependent antibody responses to antigen (Linsley P. S., et al. (1992) *Science* 257, 792–795). Thus, a subject treated with a molecule capable of inducing a T cell response can be treated with CTLA4-irnrnunoglobulin fusion protein to inhibit T cell responses to the molecule. This basic approach has widespread application as an adjunct to therapies which utilize a potentially immunogenic molecule for therapeutic purposes. For example, an increasing number of therapeutic approaches utilize a proteinaceous molecule, such as an antibody, fusion protein or the like, for treatment of a clinical disorder. A limitation to the use of such molecules therapeutically is that they can elicit an immune response directed against the therapeutic molecule in the subject being treated (e.g., the efficacy of murine monoclonal antibodies in human subjects is hindered by the induction of an immune response against the antobodies in the human subject). Administration of a CTLA4-immunoglobulin fusion protein to inhibit antigen-specific T cell responses can be applied to these therapeutic situations to enable long term usage of the therapeutic molecule in the subject without elicitation of an immune response. For example, a therapeutic antibody (e.g., murine mAb) is administered to a subject (e.g., human), which typically activates T cells specific for the antibody in the subject. To inhibit the T cell response against the therapeutic antibody, the therapeutic antibody is administered to the subject together with a CTLA4-immunoglobulin fusion protein of the invention.

When used therapeutically, a CTLA4-immunoglobulin fusion protein of the invention can be used alone or in conjunction with one or more other reagents that influence immune responses. A CTLA4-immunoglobulin fusion protein and another immunomodulating reagent can be combined as a single composition or administered separately (simultaneously or sequentially) to downregulate T cell mediated immune responses in a subject. Examples of other immunomodulating reagents include blocking antibodies, e.g., against B7-1, B7-2 or other B cell surface antigens or cytokines, other fusion proteins, e.g., CD28Ig, or immunosuppressive drugs, e.g., cyclosporine A or FK506.

The CTLA4-immunoglobulin fusion proteins of the invention may also be useful in the construction of therapeutic agents which block immune cell function by destruction of the cell. For example, by linking a CTLA4-immunoglobulin fusion protein to a toxin such as ricin or diptheria toxin, an agent capable of preventing immune cell activation would be made. Infusion of one or a combination of immunotoxins into a patient would result in the death of immune cells, particularly of activated B cells that express higher amounts of B7-1 and/or B7-2.

B. Screening Assays

Another application of the CTLA4-immunoglobulin fusion proteins of the invention is the use the protein in screening assays to discover as yet undefined molecules which inhibit an interaction between CTLA4 and a CTLA4 ligand, such as B7-1 or B7-2. For example, the CTLA4-immunoglobulin fusion protein can be used in a solid-phase binding assay in which panels of molecules are tested. In one embodiment, the screening method of the invention involves contacting a CTLA4-immunoglobulin fusion protein of the invention with a CTLA4 ligand and a molecule to be tested. Either the CTLA4-immunoglobulin fusion protein or the CTLA4 ligand is labeled with a detectable substance, such as a radiolabel or biotin, which allows for detection and quantitation of the amount of binding of CTLA4-immunoglobulin to the CTLA4 ligand. After allowing CTLA4-immunoglobulin and the CTLA4 ligand to interact in the presence of the molecule to be tested, unbound labeled CTLA4-immunoglobulin fusion protein or unbound labeled CTLA4 ligand is removed and the amount of CTLA4-immunoglobulin fusion protein bound to the CTLA4 ligand is determined. A reduced amount of binding of CTLA4-immunoglobulin fusion protein to the CTLA4 ligand in the presence of the molecule tested relative to the amount of binding in the absence of the molecule is indicative of an ability of the molecule to inhibit binding of CTLA4 to the CTLA4 ligand. Suitable CTLA4 ligands for use in the screening assay include B7-1 or B7-2 (e.g., B7-1Ig or B7-2Ig fusion proteins can be used). Preferably, either the unlabeled CTLA4-immunoglobulin fusion protein or the unlabeled CTLA4 ligand is immobilized on a solid phase support, such as a polystyrene plate or bead, to facilitate removal of the unbound labeled protein from the bound labeled protein.

C. Antibody Production

The CTLA4-immunoglobulin fusion proteins produced from the nucleic acid molecules of the invention can also be used to produce antibodies specifically reactive with the fusion protein and in particular with the CTLA4 moiety thereof (i.e., anti-CTLA4 antibodies). For example, by immunization with a CTLA4-immunoglobulin fusion protein, anti-CTLA4 polyclonal antisera or monoclonal antibodies can be made using standard methods. A mammal, (e.g., a mouse, hamster, or rabbit) can be immunized with an immunogenic form of the fusion protein which elicits an antibody response in the mammal. Techniques for conferring immunogenicity on a protein include conjugation to carriers or other techniques well known in the art. For example, the protein can be administered in the presence of adjuvant. The progress of immunization can be monitored by detection of antibody titers in plasma or serum. Standard ELISA or other immunoassay can be used with the immunogen as antigen to assess the levels of antibodies. An ELISA or other immunoassay which distinguishes antibodies reactive with the CTLA4 portion of the fusion protein from those which react with the IgC region are preferred (e.g., the extracellular domain of CTLA4 alone can be used in a standard ELISA to detect anti-CTLA4 antibodies).

Following immunization, antisera can be obtained and, if desired, polyclonal antibodies isolated from the sera. To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art. Examples include the hybridoma technique originally developed by Kohler and Milstein (*Nature* (1975) 256:495–497) as well as other techniques such as the human B-cell hybridoma technique (Kozbar et al., *Immunol. Today* (1983) 4:72), the EBV-hybridoma technique to produce human monoclonal antibodies (Cole et al. *Monoclonal Antibodies in Cancer Therapy* (1985) (Allen R. Bliss, Inc., pages 77–96), and screening of combinatorial antibody libraries (Huse et al., *Science* (1989) 246:1275). Hybridoma cells can be screened immunochemically for production of antibodies specifically reactive with CTLA4 and monoclonal antibodies isolated.

The term antibody as used herein is intended to include fragments thereof which are also specifically reactive with a CTLA4-immunoglobulin fusion protein as described herein. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments. The term "antibody" is further intended to include bispecific and chimeric molecules having an anti-CTLA4-immunoglobulin fusion protein portion, chimeric antibody derivatives, i.e., antibody molecules that combine a non-human animal variable region and a human constant region, and humanized antibodies in which parts of the variable regions, especially the conserved framework regions of the antigen-binding domain, are of human origin and only the hypervariable regions are of non-human origin. Techniques for preparing chimeric or humanized antibodies are well known in the art (see e.g., Morrison et al., *Proc. Natl. Acad. Sci. U.S.A.* 81:6851 (1985); Takeda et al., *Nature* 314:452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B, Teng et al., *Proc. Natl. Acad. Sci. U.S.A.*, 80:7308–7312 (1983); Kozbor et al., *Immunology Today*, 4:7279 (1983); Olsson et al., *Meth. Enzymol.*, 92:3–16 (1982); PCT Publication WO92/06193 and EP 0239400). Another method of generating specific antibodies, or antibody fragments, reactive against a CTLA4-immunoglobulin fusion protein is to screen expression libraries encoding immunoglobulin genes, or portions thereof, expressed in bacteria with a fusion protein produced from the nucleic acid molecules of the invention. For example, complete Fab fragments, V$_H$ regions, Fv regions and single chain Fv regions can be expressed in bacteria using phage expression libraries. See for example Ward et al., *Nature*, 341: 544–546: (1989); Huse et al., *Science*, 246: 1275–1281 (1989); and McCafferty et al., *Nature*, 348: 552–554 (1990). Screening such libraries with, for example, a CTLA4-immunoglobulin fusion protein can identify immunoglobin fragments reactive with the protein, in particular the CTLA4 portion thereof.

An anti-CTLA4 antibody generated using the CTLA4-immunoglobulin fusion proteins described herein can be used therapeutically to inhibit immune cell activation through blocking receptor:ligand interactions necessary for stimulation of the cell. These so-called "blocking antibodies" can be identified by their ability to inhibit T cell proliferation and/or cytokine production when added to an in vitro costimulation assay as described herein. The ability of blocking antibodies to inhibit T cell functions may result in immunosuppression and/or tolerance when these antibodies are administered in vivo.

D. Protein Purification

The CTLA4-immunoglobulin fusion proteins of the invention can be used to isolate CTLA4 ligands from cell extracts or other preparations. For example, a CTLA4-immunoglobulin fusion protein can be used to immunoprecipitate B7-1, B7-2 or an as yet unknown CTLA4 ligand from a whole cell, cytosolic or membrane protein extract prepared from B cells or other antigen presenting cell using standard techniques. Additionally, anti-CTLA4 polyclonal or monoclonal antibodies prepared as described herein using a CTLA4-immunoglobulin fusion protein as an immunogen can be used to isolate the native CTLA4 antigen from cells. For example, antibodies reactive with the CTLA4 portion of the CTLA4-immunoglobulin fusion protein can be used to isolate the naturally-occurring or native form of CTLA4 from activated T lymphocytes by immunoaffinity chromatography using standard techniques.

This invention is further illustrated by the following examples which should not be construed as limiting. The contents of all references and published patent applications cited throughout this application are hereby incorporated by reference.

EXAMPLE 1

Preparation of CTLA4-immunoglobulin Fusion Proteins with Reduced Effector Function The extracellular portion of the T cell surface receptor CTLA4 was prepared as a fusion protein coupled to an immunoglobulin constant region. The immunoglobulin constant region was genetically modified to reduce or eliminate effector activity inherent in the immunoglobulin structure. Briefly, DNA encoding the extracellular portion of CTLA4 was joined to DNA encoding the hinge, CH2 and CH3 regions of human IgCγ1 or IgCγ4 modified by directed mutagenesis. This was accomplished as follows:

Preparation of Gene Fusions

DNA fragments corresponding to the DNA sequences of interest were prepared by polymerase chain reaction (PCR) using primer pairs described below. In general, PCR reactions were prepared in 100 μl final volume composed of Taq polymerase buffer (Gene Amp PCR Kit, Perkin-Elmer/Cetus, Norwalk, Conn.) containing primers (1 μM each), dNTPs (200 μM each), 1 ng of template DNA, and Taq polymerase (Saiki, R.K., et al. (1988) *Science* 239:487–491). PCR DNA amplifications were run on a thermocycler (Ericomp, San Diego, Calif.) for 25 to 30 cycles each composed of a denaturation step (1 minute at 94° C.), a renaturation step (30 seconds at 54° C.), and a chain elongation step (1 minute at 72° C.).

To create gene fusions encoding hybrid proteins, "zip up" PCR was used. This procedure is diagrammed schematically in FIG. 1. A first set of forward (A) and reverse (C) primers was used to amplify the first gene segment of the gene fusion. A second set of forward (B) and reverse (D) primers was used to amplify the second gene segment of the gene fusion. Primers B and C were designed such that they contained complimentary sequences capable of annealing. The PCR products amplified by primers A+C and B+D are combined, annealed and extended ("zipped up"). The full-length gene fusion was then amplified in a third PCR reaction using the "zip up" fragment as the template and primers A and D as the forward and reverse primers, respectively.

The structure of each CTLA4 genetic fusion consisted of a signal sequence, to facilitate secretion, coupled to the extracellular domain of CTLA4 and the hinge, CH2 and CH3 domains of human IgCγ1 or IgCγ4. The IgCγ1 and IgCγ4 sequences were modified to contain nucleotide changes within the hinge region to replace cysteine residues available for disulfide bond formation and to contain nucleotide changes in the CH2 domain to replace amino acids thought to be required for IgC binding to Fc receptors and complement activation. The hinge region and CH2 domain amino acid mutations introduced into IgCγ1 and IgCγ4 are illustrated in FIGS. 2A and 2B, respectively.

A. Construction of CTLA4-Ig Fusion Genes

1. Preparation of the Signal Sequence Gene Segment

PCR amplification was used to generate an immunoglobulin signal sequence suitable for secretion of the CTLA4-Ig fusion protein from mammalian cells. The Ig signal sequence was prepared from a plasmid containing the murine IgG heavy chain gene (described in Orlandi, R., et al. (1989) *Proc. Natl. Acad. Sci. USA* 86:3833–3837) using the oligonucleotide 5'CATTCTAGAACCTCGACAAGCTTG AGATCACAGTTCTCTCTAC-3' (SEQ ID NO: 1) as the forward primer and the oligonucleotide 5'CAGCAG GCTGGGCCACGTGCATTGCGGAGTGGACACCT GTGGAGAG-3' ( SEQ ID NO: 2) as the reverse PCR primer. The forward PCR primer (SEQ ID NO: 1) contains recognition sequences for restriction enzymes XbaI and HindIII and is homologous to sequences 5' to the initiating methionine of the Ig signal sequence. The reverse PCR primer (SEQ ID NO: 2) is composed of sequences derived from the 5' end of the extracellular domain of CTLA4 and the 3' end of the Ig signal sequence. PCR amplification of the murine Ig signal template DNA using these primers resulted in a 233 bp product which is composed of XbaI and HindIII restriction sites followed by the sequence of the Ig signal region fused to the first 25 nt of the coding sequence of the extracellular domain of CTLA4. The junction between the signal sequence and CTLA4 is such that protein translation beginning at the signal sequence will continue into and through CTLA4 in the correct reading frame.

2. Preparation of the CTLA4 Gene Segment

The extracellular domain of the CTLA4 gene was prepared by PCR amplification of plasmid phCTLA4. This plasmid contained the sequences corresponding to the human CTLA4 cDNA (see Darivach, P., et al., (1988) *Eur. J. Immunol.* 18:1901 1905; Harper, K., et al., (1991) *J. Immunol.* 147: 1047–1044) inserted into the multiple eloning gite of vector pBluescript (Stratagene, La Jolla, Calif.) and served as the template for a PCR amplification using the oligonucleotide 5'-CTCTCCACAGGTGTCCACTCCGCA ATGCACGTGGCCCAGCCTGCTG-3' (SEQ ID NO: 3) as the forward PCR primer and the oligonucleotide 5'-TGTGTGTGGAATTCTCATTACTGATCAGAATCTG GGCACGGTTCTG-3' (SEQ ID NO: 4) as the reverse PCR primer. The forward PCR primer (SEQ ID NO: 3) was composed of sequences derived from the 3' end of the Ig signal sequence and the 5' end of the extracellular domain of CTLA4. This PCR primer is the complementary to murine Ig signal reverse PCR primer (SEQ ID NO: 2). The reverse PCR primer (SEQ ID NO: 4) was homologous to the 3' end of the extracellular domain of CTLA4, added a BclI restriction site and an additional G nucleotide at the end of the extracellular domain. This created a unique BclI restriction site and added a glutamine codon to the C-terminus of the extracellular domain. The final PCR product was 413 bp.

3. Fusion of the Immunoglobulin Signal Sequence and CTLA4 Gene Segments

The PCR fragments containing the signal and CTLA4 sequences were joined together via a third PCR reaction. Both PCR fragments (1 ng each) were mixed together along with the Ig signal forward PCR primer (SEQ ID NO: 1) and the CTLA4 reverse PCR primer (SEQ ID NO: 4) and PCR amplified as described. in this reaction, the 3' end of the Ig signal fragment hybridizes with the 5' end of the CTLA4 fragment and the two strands are extended to yield a full length 600 bp fragment. Subsequent PCR amplification of this fragment using forward (SEQ ID NO: 1) and reverse (SEQ ID NO: 4) yielded sufficient amounts of the signal-CTLA4 gene fusion fragment for cloning. This fragment contains a 5' XbaI and a 3' BclI restriction sites flanking the Ig signalCTLA4 gene fusion segment for subsequent cloning.

4. Cloning of Immunoglobulin Constant Domain Gene Segments

Plasmid pSP721gG1 was prepared by cloning the 2000 bp segment of human IgG1 heavy chain genomic DNA (Ellison, J. W., et al., (1982) *Nucl. Acids. Res.* 10:4071–4079) into the multiple cloning site of cloning vector pSP72 (Promega, Madison, Wis.). Plasmid pSP721gG1 contained genomic DNA encoding the CH1, hinge, CH2 and CH3 domain of the heavy chain human IgCγ1 gene. PCR primers designed to amplify the hinge-CH2-CH3 portion of the heavy chain along with the intervening genomic DNA were prepared as follows. The forward PCR primer, 5'-GCATTTTAAGCTTTTTCCTGATCA GGAGCCCAAATCTTCTGACAAAACTCACACATCTC CACCGTCTCCAGGTAAGCC-3' (SEQ ID NO: 5), contained HindIII and BclI restriction sites and was homologous to the hinge domain sequence except for five nucleotide substitutions which changed the three cysteine residues to serines. The reverse PCR primer, 5'-TAATACGA CTCACTATAGGG-3' (SEQ ID NO: 6), was identical to the commercially available T7 primer (Promega, Madison, WI). Amplification with these primers yielded a 1050 bp fragment bounded on the 5' end by HindIII and BclI restriction sites and on the 3' end by BamHI, SmaI, KpnI, SacI, EcoRI, ClaI, EcoR5 and BglII restriction sites. This fragment contained the IgCγ1 hinge domain in which the three cysteine codons had been replaced by serine codons followed by an intron, the CH2 domain, an intron, the CH3 domain and additional 3' sequences. After PCR amplification, the DNA fragment was digested with HindIII and EcoRI and cloned into expression vector pNRDSH (Repligen; Cambridge, Mass. (diagrammed in FIG. 3)) digested with the same restriction enzymes. This created plasmid pNRDSH/IgG1.

A similar PCR based strategy was used to clone the hinge-CH2-CH3 domains of human IgCγ4 constant regions. A plasmid, p428D (Medical Research Council, London, England) containing the complete IgCγ4 heavy chain genomic sequence (Ellison, J., et al., (1981) *DNA* 1: 11–18) was used as a template for PCR amplification using oligonucleotide 5'GAGCATTTTCCTGATCAGGAGTCCAAA TATGGTCCCCCACCCCATCATCCCCAGGTAAGCCAA CCC-3' (SEQ ID NO: 7) as the forward PCR primer and oligonucleotide 5'GCAGAGGAATTCGAGCTCGGTACC CGGGGATCCCCAGTGTGGGGACAGTGGGACCCGC TCTGCCTCCC-3' (SEQ ID NO: 8) as the reverse PCR primer. The forward PCR primer (SEQ ID NO: 7) contains a BclI restriction site followed by the coding sequence for the hinge domain of IgCγ4. Nucleotide substitutions have been made in the hinge region to replace the cysteines residues with serines. The reverse PCR primer (SEQ ID NO: 8) contains a PspAI restriction site. PCR amplification with these primers results in a 1179 bp DNA fragment. The PCR product was digested with BclI and PspAI and ligated to pNRDSH/IgG1 digested with the same restriction enzymes to yield plasmid pNRDSH/IgG4. In this reaction, the IgCγ4 domain replaced the IgCγ1 domain present in pNRDSH/IgG1.

5. Modification of Immunoglobulin Constant Domain Gene Segments

Modification of the CH2 domain in IgC to replace amino acids thought to be involved in binding to Fc receptor was accomplished as follows. Plasmid pNRDSH/IgG1 served as template for modifications of the IgCγ1 CH2 domain and plasmid pNRDSH/IgG4 served as template for modifications of the IgCγ4 CH2 domain. Plasmid pNRDSH/IgG1 was PCR amplified using a forward PCR primer (SEQ ID NO: 5) and oligonucleotide 5'-GGGTTTTGGGGGGAA GAGGAAGACTGACGGTGCCCCC TCGGCTTCAG GTGCTGAGGAAG-3' (SEQ ID NO: 9) as the reverse PCR primer. The forward PCR primer (SEQ ID NO: 5) has been previously described and the reverse PCR primer (SEQ ID NO: 9) was homologous to the amino terminal portion of the CH2 domain of IgG1 except for five nucleotide substitutions designed to change amino acids 234, 235, and 237 from Leu to Ala, Leu to Glu, and Gly to Ala, respectively (Canfield, S. M. and Morrison, S. L. (1991) *J. Exp. Med.* 173: 1483–1491; see FIG. 2A). Amplification with these PCR primers will yield a 239 bp DNA fragment consisting of a modified hinge domain, an intron and modified portion of the CH2 domain.

Plasmid pNRDSH/IgG1 was also PCR amplified with the oligonucleotide 5'-CATCTCTTCCTCAGCACCTGAAGC CGAGGGGGCACCGTCAGTCTTCCTCTTCCCCC-3' (SEQ ID NO: 10) as the forward primer and oligonucleotide (SEQ ID NO: 6) as the reverse PCR primer. The forward PCR primer (SEQ ID NO: 10) is complementary to primer (SEQ ID NO: 9) and contains the five complementary nucleotide changes necessary for the CH2 amino acid replacements. The reverse PCR primer (SEQ ID NO: 6) has been previously described. Amplification with these primers yields a 875 bp fragment consisting of the modified portion of the CH2 domain, an intron, the CH3 domain, and 3' additional sequences.

The complete IgCγ1 segment consisting of modified hinge domain, modified CH2 domain and CH3 domain was prepared by an additional PCR reaction. The purified products of the two PCR reactions above were mixed, denatured (95° C., 1 minute) and then renatured (54° C., 30 seconds) to allow complementary ends of the two fragments to anneal. The strands were filled in using dNTP and Taq polymerase and the entire fragment amplified using forward PCR primer (SEQ ID NO: 5) and reverse PCR primer (SEQ ID NO: 6). The resulting fragment of 1050 bp was purified, digested with HindIII and EcoRI and ligated to pNRDSH previously digested with the same restriction enzymes to yield plasmid pNRDSH/IgG1m.

Two amino acids at immunoglobulin positions 235 and 237 were changed from Leu to Glu and Gly to Ala, respectively, within the IgCγ4 CH2 domain to eliminate Fc receptor binding (see FIG. 2B). Plasmid pNRDSH/IgG4 was PCR amplified using the forward primer (SEQ ID NO: 7) and the oligonucleotide 5'CGCACGTGACCTCA GGGGTCCGGGAGATCATGAGAGTGTCCTTGGGTTT TGGGGGGAACAGGAAGACTGATGGTGCCCCCTCG AACTCAGGTGCTGAGG-3' (SEQ ID NO: 11) as the reverse primer. The forward primer has been previously described and the reverse primer was homologous to the amino terminal portion of the CH2 domain, except for three nucleotide substitutions designed to replace the amino acids described above. This primer also contained a PmlI restriction site for subsequent cloning. Amplification with these primers yields a 265 bp fragment composed of the modified hinge region, and intron, and the modified 5' portion of the CH2 domain.

Plasmid pNRDSH/IgG4 was also PCR amplified with the oligonucleotide 5'-CCTCAGCACCTGAGTTCGAGGGG GCACCATCAGTCTTCCTGTTCCCCCCAAAACCCAA GGACACTCTCATGATCTCCCGGACCCCTGAGGTCA CGTGCG-3'(SEQ ID NO: 12) as the forward primer and oligonucleotide (SEQ ID NO: 8) as the reverse PCR primer. The forward PCR primer (SEQ ID NO: 12) is complementary to primer (SEQ ID NO: 11) and contains the three complementary nucleotide changes necessary for the CH2 amino acid replacements. The reverse PCR primer (SEQ ID NO: 8) has been previously described. Amplification with these primers yields a 1012 bp fragment consisting of the modified portion of the CH2 domain, an intron, the CH3 domain, and 3' additional sequences.

The complete IgCγ4 segment consisting of modified hinge domain, modified CH2 domain and CH3 domain was prepared by an additional PCR reaction. The purified products of the two PCR reactions above were mixed, denatured (95° C., 1 minute) and then renatured (54° C., 30 seconds) to allow complementary ends of the two fragments to anneal. The strands were filled in using dNTP and Taq polymerase and the entire fragment amplified using forward PCR primer (SEQ ID NO: 7) and reverse PCR primer (SEQ ID NO: 8). The resulting fragment of 1179 bp was purified, digested with BclI and PspAI and ligated to pNRDSH previously digested with the same restriction enzymes to yield plasmid pNRDSH/IgG4m.

6. Assembly of CTLA4-Immunoglobulin Fusion Genes

The PCR fragment corresponding to the Ig signal-CTLA4 gene fusion prepared as described above (sections 1–3) was digested with HindIII and BclI restriction enzymes and ligated to pNRDSH/IgG1, pNRDSH/IgG1m, pNRDSH/IgG4, and pNRDSH/IgG4m previously digested with the same restriction enzymes to create expression plasmids in which the signal-CTLA4-IgG gene fusion segment is placed under the control of the CMV promoter. The ligated plasmids were transformed into *E. coli* JM109 using CaCl$_2$ competent cells and transformants were selected on L-agar containing ampicillin (50 μg/ml; as described in *Molecular Cloning: A Laboratory Manual* (1982) Eds. Maniatis, T., Fritsch, E. E., and Sambrook, J. Cold Spring Harbor Laboratory). Plasmids isolated from the transformed *E. coli* were analyzed by restriction enzyme digestion. Plasmids with the expected restriction pattern were sequenced to verify all portions of the signal-CTLA4-IgG gene fusion segments. The final plasmids were named pNRDSH/sigCTLA4-IgG1, pNRDSH/sigCTLA4-IgG1m, pNRDSH/sigCTLA4-IgG4 and pNRDSH/sigCTLA4-IgG4m. The signal-CTLA4-IgG gene fusion segments from each of these constructs were also transferred to the pEE12 expression vector (Biotechnology (1992) 10:169–175).

The nucleotide and predicted amino acid sequences of the signal-CTLA4-IgG gene fusion segments are shown in the Sequence Listing as follows: sigCTLA4-IgGm- SEQ ID NOS: 23 and 24, sigCTLA4-IgG4- SEQ ID NOS: 25 and 26 and sigCTLA4-IgG4m- SEQ ID NOS: 27 and 28.

B. Construction of a CTLA4Ab Fusion Gene

The extracellular domain of CTLA4 is an immunoglobulin superfamily member and is responsible for binding to its ligands B7-1 and B7-2. The replacement of the heavy and light chain variable domains of an antibody molecule with the extracellular domain of CTLA4 will result in an antibody-like protein which can bind specifically to B7-1, B7-2 and other CTLA4 ligands with high affinity. The construction of such a molecule using human IgG1 antibody heavy and light chains is described below.

1. Construction of the Heavy Chain Gene

The Ig signal sequence was prepared from template plasmid pSP72IgG1 by PCR amplification using oligonucleotide 5'CATTCGCTTACCTCGACAAGCTTGAGATC ACAGTTCTCTCTAC-3' (SEQ ID NO: 13) as the forward PCR primer and oligonucleotide 5'-GGAGTGGAC ACCTGTGGAGAG-3' (SEQ ID NO: 14) as the reverse primer. The forward PCR primer (SEQ ID NO: 13) contains a HindIII restriction site and part of the 5' untranslated segment of the Ig signal domain. The reverse PCR primer (SEQ ID NO: 14) corresponds to the C-terminus of the natural Ig signal peptide. Amplification with these primers resulted in a 208 bp fragment encoding the entire Ig signal sequence.

The CTLA4 extracellular domain was prepared from plasmid phCTLA4, which contained the entire CTLA4 cDNA sequence, by PCR amplification using oligonucleotide 5'-CTCCACAGGTGTCCACTCCGCAATGCAC GTGGCCCAGCC-3' (SEQ ID NO: 15) as the forward PCR primer and oligonucleotide 5'GAGGTTGTAAGGAC TCACCTGAAATCTGGGCTCCGTTGC-3' (SEQ ID NO: 16) as the reverse primer. The forward primer (SEQ ID NO: 15) contained sequences homologous to the 5' end of the CTLA4 extracellular domain and to the 3' end of the Ig signal domain. The reverse primer (SEQ ID NO: 16) contained the 3' end of the CTLA4 extracellular domain and intervening sequences, including a splice acceptor site. Amplification with these primers yielded a 379 bp fragment containing the CTLA4 extracellular domain.

An intervening sequence DNA fragment derived from the intron between the antibody variable and constant (CHI) domains was prepared by PCR amplification using oligonucleotide 5'GCAACGGAGCCCAGATTTCAGGTG AGTCCTTACAACCTC-3' (SEQ ID NO: 17) as the forward PCR primer and oligonucleotide 5'GGCTAGATA TCTCTAGACTATAAATCTCTGGCCATGAAG-3' (SEQ ID NO: 18) as the reverse PCR primer. The forward PCR primer (SEQ ID NO: 17) contains intron sequence and is complementary to the 3' end of the extracellular domain of CTLA4 and is complimentary to the CTLA4 reverse PCR primer (SEQ ID NO: 16). The reverse primer (SEQ ID NO: 18) contains intron sequences and an additional XbaI restriction site. Amplification with these primers yields a 197 bp fragment.

The PCR fragments encoding the Ig signal, CTLA4 extracellular domain and the intervening sequence were mixed, denatured and renatured to allow hybridization of complementary ends. The strands were filled in and the product amplified using forward (SEQ ID NO: 13) and reverse (SEQ ID NO: 18) PCR primers. The product was a 764 bp fragment which encoded the Ig signal, the CTLA4 extracellular domain, an intron sequence flanked by HindIII and XbaI restriction sites. This DNA fragment was digested with HindIII and XbaI and ligated to pSP72IgG1, resulting in the CTLA4 extracellular domain being linked to a 5' Ig signal sequence and a 3' antibody CH1, hinge, CH2, and CH3 domains.

The nucleotide and predicted amino acid sequences of the assembled CTLA4-heavy chain are shown in SEQ ID NOS: 29 and 30, respectively.

2. Construction of the Light Chain Gene

The replacement of a human immunoglobulin antibody light chain variable domain (Hieter, P. A., et al., (1980) *Cell* 22:197) with the CTLA4 extracellular domain proceeded as follows. The Ig signal fragment was prepared as for the heavy chain replacement, described above. The CTLA4 extracellular domain was prepared using a forward PCR primer (SEQ ID NO: 15) previously described and oligonucleotide 5'GGCACTAGGTCGACTCTAGAAACTG AGGAAGCAAAGTTTAAATTCTACTCACGTTTAATCT GGGCTCCGTTGC-3' (SEQ ID NO: 19) as the reverse primer. The reverse primer contained sequences of the 3' end of the CTLA4 extracellular domain, a splice receptor, and intervening sequence DNA containing an XbaI restriction site. The Ig signal fragment and the CTLA4 extracellular domain were joined by mixing the DNA fragment, denaturing, and renaturing to anneal their complementary ends. The strands were filled in and the fragment PCR amplified using forward (SEQ ID NO: 13) and reverse (SEQ ID NO: 19) PCR primers previously described. The resulting DNA fragment was digested with the HindIII and XbaI and ligated to immunoglobulin light chain vector paLYS 17 digested with the same enzymes. The resulting plasmid pCTLA4kappa contains an Ig signal sequence, an intron, the CTLA4 extracellular domain, an intron, and the light chain (kappa) constant domain.

The nucleotide and predicted amino acid sequences of the assembled CTLA4-light chain are shown in SEQ ID NOS: 31 and 32, respectively.

The DNA segments encoding the recombinant heavy and light chains were transferred to the pEE12 vector or the pNRDSH vector and stable NSO or CHO expression cell lines established as described below. CHO and NSO supernatants were assayed for the production of CTLA4 light chain and CTLA4 heavy chain fusion proteins by ELISA and binding to B7-1 was measured using CHO/hB7-1 expressing cells and FACS (as described in Example 2). It is also contemplated that the heavy and light chain constructs of the present invention be expressed in the same vector and host cells transfected in one step.

C. Expression of CTLA4 Fusion Proteins in CHO and NSO cells

The various CTLA4-immunoglobulin fusion proteins were expressed in CHO cells as follows. Briefly, $5 \times 10^5$ CHO-DG44 cells (subline of CHO-K1, available from ATCC) were transfected with 10 µg of the appropriate expression plasmid (PNRDSH series) by the calcium phosphate method (described in *Molecular Cloning: A Laboratory Manual* (1982) Eds. Maniatis, T., Fritsch, E. E., and Sambrook, J. Cold Spring Harbor Laboratory) using a commercially available kit (5 Prime to 3' Prime Inc., Boulder, Colo.) according to the manufacturer's instructions. The transfected cells were allowed to recover in nonselective media (alpha MEM medium containing 10% heat inactivate fetal bovine serum (FBS), Gibco/BRL, Gaithersburg, Md.) for two days and then plated in selective media (alpha MEM minus nucleoside medium containing 10% FBS and 550 µg/ml G418; Gibco/BRL, Gaithersburg, Md.). Individual subclones were obtained by dilution cloning in selective media. Culture media was assayed for the presence of secreted CTLA4-immunoglobulin by a standard ELISA designed to detect human IgG.

The various CTLA4-immunoglobulin and CTLA4Ab fusion proteins were expressed in NSO cells (Golfre, G. and Milstein C. P. (1981) *Methods Enzymol.* 73B: 3–46) as follows. Briefly, $10^7$ NSO cells were transfected by electroporation (using a BioRad Gene Pulser, Hercules, Calif.) with 40 µg of the appropriate expression plasmid (pEE12 series) previously linearized by digestion with SalI restriction endonuclease. The transfected cells were selected using DMEM media deficient in glutamine (Gibco/BRL, Gaithersberg Md.). Individual subclones were isolated by dilution cloning in selective media. Culture media assayed for the presence of secreted CTLA4-Ig or CTLA4Ab fusion protein by a standard ELISA assay designed to detect human IgG.

As a representative example, transfection of either the pNRDSH/sigCTLA4-IgG4m and pEE12/sigCTLA4-IgG4m expression vector into CHO or NSO host cells resulted in selected subclones that secreted hCTLA4IgG4m fusion protein into culture supernatants at a concentration of 75–100 µg/ml.

D. Purification of CTLA4 Fusion Proteins

The CTLA4-Ig and CTLA4Ab fusion proteins are purified from the culture medium of transfected CHO or NSO cells as follows. Culture medium was concentrated 10 fold by ultra filtration (Ultrasette, Filtron Technology Corp., Northborough, Mass.) and batch bound overnight to immobilized protein A (IPA-300, Repligen Corp., Cambridge, Mass.). The protein-bound resin was poured into a chromatography column, washed with 10 column volumes of optimal binding buffer (1.5 M glycine, 3M NaCl, pH 8.9) and the bound CTLA4-Ig or CTLA4Ab was eluted by the addition of 0.1 M Na citrate, pH 3.0. Fractions were collected and neutralized with the addition of 1 M Tris base to pH of 7.0. The $Abs_{280nm}$ was monitored for each fraction and peak fractions were analyzed by SDS-PAGE, followed by Coomassie Blue staining and Western blot analysis using an anti-CTLA4 polyclonal antiserum (described in Lindsten, T. et al. (1993) *J. Immunol.* 151:3489–3499). Fractions containing CTLA4-Ig or CTLA4Ab were pooled and dialyzed against 200 volumes of 0.5×PBS overnight at 4° C. The purified protein was assayed for binding to its ligand (B7-1 and/or B7-2) as described in Example 2.

EXAMPLE 2

Characterization of CTLA4 Fusion Proteins

The ability of the various CTLA4-Ig forms and CTLA4Ab to bind to their counter receptors B7-1 (Freeman, G. F., et al. (1988) *J. Immunol.* 143:2714–2722) and B7-2 (Freeman, G. F., et al., (1993) *Science* 262: 909–91 1) was demonstrated using the following assays.

A. Fluorescence Activated Cell Staining (FACS).

Purified preparations of the various recombinant CTLA4 forms were tested for their ability to bind to transfected COS cell transiently expressing hB7-1 or hB7-2 or transfected CHO cells stably expressing hB7-1 or hB7-2. The recombinant CTLA4 protein (10 µg/ml) was incubated with B7 expressing cells ($2 \times 10^6$ cells) for 1 hr on ice in FACS wash solution (1% bovine serum albumin in PBS). The cells were washed 3 times with FACS wash solution. The cell bound CTLA4 was detected by reaction with anti-human Ig-FITC (Dako Corporation, Carpintera, Calif.) or protein A-FITC (Dako) for 30 mintues on ice in the dark. The cells were washed twice with FACS wash solution and then fixed in 1% parafornaldehyde in PBS. The cells were analyzed for fluorescence intensity using a Becton Dickinson (San Jose, Calif.) FACS analyzer. Murine anti-human mAbs reactive with either hB7-1 or hB7-2 served as positive control reagents for the hB7-1 and hB7-2 receptor expressing cells. These mAbs were detected using goat anti-murine IgG-FITC (Dako corporation, Carpintera, Calif.) and analyzed as above. Untransfected COS and CHO cells served as negative controls for each cell line. The results of this experiment demonstrated that CTLA4 immunoglobulin fusion proteins bind to CHO cells transfected to express CTLA4 ligands.

B. Competitive Binding ELISA

The ability of the various recombinant CTLA4 forms to bind to hB7-1 or hB7-2 was assessed in a competitive binding ELISA assay. This assay was established as follows. Purified recombinant hB7-Ig (50 μl at 20 μg/ml in PBS) was bound to a Costar EIA/RIA 96 well microtiter dish (Costar Corp, Cambridge Mass., USA) overnight at room temperature. The wells were washed three times with 200 μl of PBS and the unbound sites blocked by the addition of 1% BSA in PBS (200 μl/well) for 1 hour at room temperature. The wells were washed again as above. Biotinylated hCTLA4-IgG1 (prepared according to manufacturers instructions (Pierce, Rockford, IL) at 10 μg/ml serially diluted in twofold steps to 15.6 ng/ml; 50 μl/well) was added to each well and incubated for 2.5 hours at room temperature. The wells were washed again as above. The bound biotinylated hCTLA4IgG1 was detected by the addition of 50 μl of a 1:2000 dilution of streptavidin-HRP (Pierce Chemical Co., Rockford, Ill.) for 30 minutes at room temperature. The wells were washed as above and 50 μl of ABTS (Zymed, California) added and the developing blue color monitored at 405 nm after 30 min.

Figure 4A:
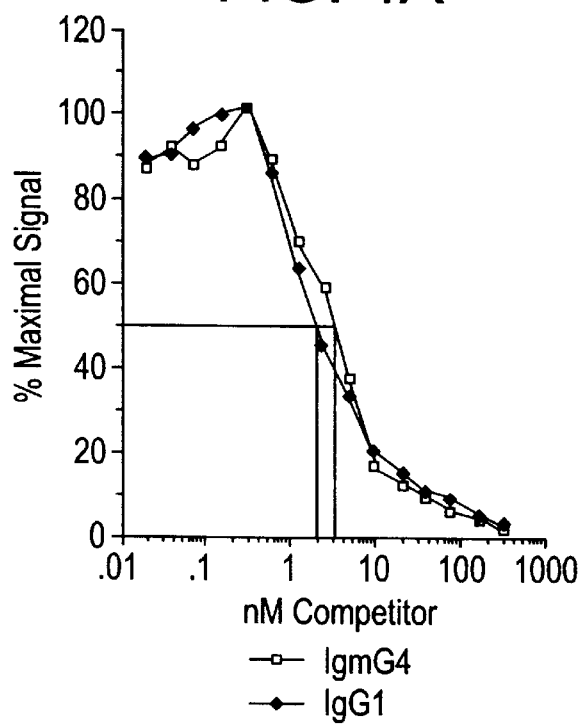
FIGS. 4A–B are graphic representations of competition ELISAs depicting the ability of unlabeled hCTLA4-IgG1 or unlabeled hCTLA4-IgG4m to compete for the binding of biotinylated hCTLA4-IgG1 to hB7-1-Ig (panel A) or hB7-2-Ig (panel B).
Figure 4B:
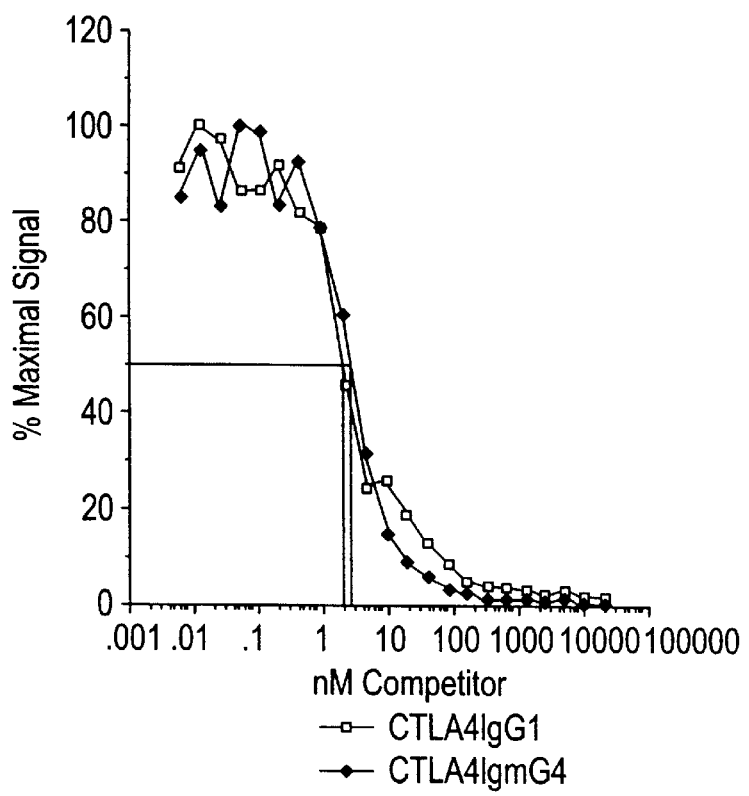

The ability of the various forms of CTLA4 to compete with biotinylated CTLA4-IgG1 was assessed by mixing varying amounts of the competing protein with a quantity of biotinylated CTLA4-IgG1 shown to be non-saturating (i.e., 70 ng/ml; 1.5nM) and performing the binding assays as described above. A reduction in the signal ($Abs_{405}$nm) expected for biotinylated CTLA4-IgG1 indicated a competition for binding to plate-bound hB7-1 or hB7-2. A graphic representation of a typical binding assay illustrating the competition of biotinylated hCTLA4-IgG1 with hCTLA4-IgG1 (itself) or hCTLA4-IgG4m is shown in FIG. 4A for binding to hB7-1 and FIG. 4B for binding to hB7-2. The competition curves show that the mutant IgG4 form competes with hCTLA4-IgG1 for binding to B7-1 or B7-2 with the same binding kinetics as the unlabeled IgG1 form itself. Accordingly, mutation of the hinge region and CH2 domain of IgCγ4 in the CTLA4 fusion protein as described herein does not detrimentally affect the ligand binding activity of the CTLA4 fusion protein.

C. SDS-PAGE and Western Blotting

The various CTLA4 forms were analyzed by SDS-PAGE followed by detection using Coomassie Blue staining or Western blotting. The CTLA4 proteins were separated on both reducing and non-reducing SDS-PAGE gels (9, 12, or 15% gels with 5% stacking gel) and stained with Coomassie Blue using standard methods. Protein size was estimated from comparison to commercial size standards (BioRad, Hercules, Calif.). Western blots were performed using standard procedures and Immobilon blotting membranes (Millipore, New Bedford, Mass.). The CTLA4 was detected using a polyclonal antisera raised in rabbit immunized with the extracellular domain of CTLA4 produced in E. coli (described in Lindsten, T. et al. (1993) J. Immunol. 151:3489–3499). The CTLA4 was visualized using [$^{125}$I]-protein A (Dupont NEN, Boston, Mass.) followed by autoradiography or using protein A-HRP. The results indicated the presence of an immunoreactive band at approximately 50 kD.

D. Measurement of Fc Receptor Binding

The binding of the various CTLA4-Ig forms and CTLA4Ab to Fc receptors was assessed by using a competitive binding assay as described in Alegre, M.-L., et al.,. (1992) J. Immunol. 148:3461 3468. Human cell line U937 was used as a source of the FcRI and FcRII receptors (Looney, R. J., et al., (1986) J. Immunol. 136:1641). U937 cells were grown with 500 U/ml IFN-γ to upregulate expression of FcR1. The U937 cells were used at a concentration of $6.25 \times 10^6$ cells/ml. Preparations of unlabeled CTLA4-IgG1, CTLA4-IgG4 and human IgG1 were serially diluted to a concentration of $2 \times 10^{-10}$ M. To each serial dilution, a fixed amount of $^{125}$I-labeled protein (e.g., CTLA4-IgG1, CTLA4-IgG4 or human IgG1) was added. The U937 cells were then added to the mixture and incubated for three hours. The cells were separated from unbound labeled and unlabeled protein by centrifugation through silicone oil for one minute at 14000×g. The tips of the tubes with the pelleted cells were then cut off and analyzed in a gamma counter. Maximal binding of labeled protein to U937 cells was determined in the absence of unlabeled competitor protein. Percent specific activity represents the percentage of labeled protein bound in the presence of unlabeled competitor protein relative to maximal binding. FIG. 5A graphically illustrates the amount of labeled CTLA4-IgG1 bound to U937 cells (expressed in counts per minute) in the presence of unlabeled CTLA4-IgG1 or CTLA4-IgG4. Unlabeled CTLA4-IgG1 was able to compete with labeled CTLA4-IgG for binding to FcR1 on U937 cells (i.e., the amount of bound labeled protein was reduced), whereas unlabeled CTLA4-IgG4 did not compete for binding. FIG. 5B graphically illustrates the percent specific activity of labeled human IgG1, CTLA4-IgG1 and CTLA4-IgG4 being competed with themselves (unlabeled). The $IC_{50}$ for human IgG1 was approximately $7.5 \times 10^{-8}$ M. The $IC_{50}$ for CTLA4-IgG1 was approximately $7 \times 10^{-8}$ M. An $IC_{50}$ for CTLA4-IgG4 could not be determined because this protein did not bind to the FcR1. These results demonstrate that use of an IgCγ4 constant region in a CTLA4-Ig fusion protein essentially eliminates the ability of the fusion protein to bind to Fc receptors.

E. Measurement of Complement Activation

CTLA4-immunoglobulin forms were tested in a ligand-specific assay for complement activation. CHO cells expressing hB7-1 on their surface were grown to confluence in tissue culture dishes. After washing away serum and medium, the cells were exposed to BCECF/AM ([2',7-bis-(carboxyethyl)-5,(6')-carboxylfluorescein acetoxymethyl)-ester] Calbiochem, La Jolla, Calif.) a fluorescent dye that irreversibly loads into the cells. The cells ($5 \times 10^5$) were then incubated with hCTLA4-immunoglobulin fusion proteins or a monoclonal antibody specific for hB7-1 (4B2). Unbound protein was washed away and a complement source was added and allowed to react with the cells for 30 minutes. Complement sources tested included guinea pig complement and human serum (as a source of human complement). After incubation with the complement source, lysis was measured by monitoring the release of the fluorescent dye from the cells using a fluorometer. Controls included parallel experiments with hB7-1 negative CHO cells. Identical cultures were also tested for their ability to bind the hCTLA4 forms under similar assay conditions. Additionally, to distinguish a lack of an ability to activate complement from a lack of an ability to bind B7-1, an ELISA-type assay of CTLA4 binding to CHO-B7-1 cells was performed as a control (described further below).

The results of typical complement activation assays are shown in FIGS. 6A–C. FIG. 6A graphically illustrates guinea pig complement-mediated lysis of CHO-B7-1 cells by CTLA4-IgG1, CTLA4-IgG4m and the anti-B7-1 monoclonal antibody 4B2. hCTLA4-IgG1 reproducibly activated guinea pig complement as well or better than the 4B2 mAb. The hCTLA4-IgG4m did not activate complement in this assay, even at concentration 100-fold higher than that needed for CTLA4-IgG1. The results were confirmed by repeating the work with human serum as the complement source, shown in FIG. 6B. Human complement produced a higher percentage lysis than the guinea pig complement, however, otherwise the results were the same, with the hCTLA4-IgG4m exhibiting a markedly reduced ability to activate complement in comparison to CTLA4-IgG1. The effect of the CTLA4 fusion proteins on complement activation is specific for the B7-1 ligand, as untransfected CHO cells were not substrates for complement activation by any of the proteins tested, illustrated in FIG. 6C (using guinea pig complement as the complement source).

Figure 7:
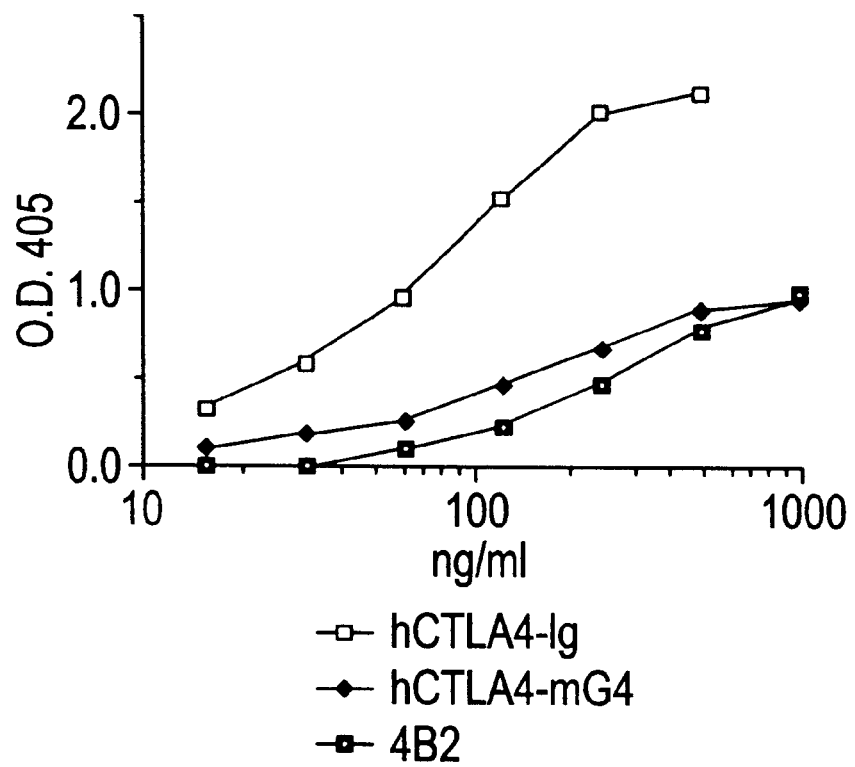
FIG. 7 is a graphic representation of the binding of CTLA4-IgG1, CTLA4-IgG4m or anti-B7-1 mAb (4B2) to CHO-B7-1 cells, demonstrating that despite the inability of CTLA4-IgG4m to activate complement it can still bind to CHO-B7-1 cells.

In order to verify that the hCTLA4-IgG4m form was still able to bind to membrane bound hB7-1, an experiment was performed by a similar method as for the complement activation study. Antibody or hCTLA4 forms were bound to washed CHO-B7-1 cells under conditions identical to those used in the complement activation studies except that instead of adding complement in the final step, an HRP-conjugated anti-Ig Fc (Calbiochem, La Jolla, Calif.) was used. Bound HRP was detected by washing the cells, adding ABTS substrate and measuring absorbence at 405 nm (as described above for the competition ELISA assay). The results are shown graphically in FIG. 7. All three B7-1 specific proteins (mAb 4B2, hCTLA4-IgG1 and hCTLA4-IgG4m) bound to the cells. The corresponding experiment using untransfected CHO cells showed no binding of the proteins to the cells. The difference in the maximal O.D. signals for the different proteins is likely due to the different affinities of the forms of Fc regions for the HRP-conjugated secondary antibodies.

F. Inhibition of T Cell Proliferation

The ability of the CTLA4-Ig forms and CTLA4Ab to inhibit the proliferation of T cells in a costimulation proliferation assay was measured. CD4$^+$ T cells are prepared from human blood by density gradient centrifugation on Ficoll-Hypaque (Sigma, St. Louis, Mo.). Monocytes were removed by adherence to plastic and the CD4$^+$ cells further enriched by removal of residual monocytes, B cells, NK cells and CD8+ T cells by lysis with complement and mAbs (anti-CD14, antiCD11b, anti-CD20, anti-CD16 and anti-CD8) or by negative selection using the same immunomagnetic beads (Advanced Magnetics, Cambridge, Mass.) (as described in Boussioutis, Va., et al., (1993) *J. Exp. Med.* 178:1758–1763). CD4+T cells ($10^5$) were cultured in the presence of immobilized anti-CD3 mAb (coated at 1 ug/well, overnight) and CHO cells expressing hB7-1 or hB7-2 ($2\times10^4$) in a microtiter plate with or without one of the CTLA4 forms and incubated for 3 days. Thymidine incorporation as a measure of mitogenic activity was assessed after overnight incubation in the presence of [$^3$H] thymidine (Gimmi, C. D., et al., (1991) *Proc. Natl. Acad. Sci USA* 88:6575–6579). Inhibition was calculated as a percent of proliferation in control cultures. The data show that both the CTLA4IgG1 and CTLA4Ig4m performed well, inhibiting T cell proliferation to the same extent when used in equivalent amounts, i.e. the two compounds were indistinguishable in potentcy.

G. Pharmacokinetic Studies

The effect of mutating the IgG4 heavy chain, as described herein, on the pharmacokinetics of a CTLA4Ig in rats was examined. Pharmacokinetics were performed on two CTLA4If differing only in their heavy chain constant domains, where one form contained the wild type human IgGlIg (referred to as hCTLA4IgG1) and the second antibody contained the mutated version of human IgG4 (referred to as hCTLA4IgG4m). Two Sprague-Dawley male rats weighing 0.3–0.4 kg were used for each protein. The CTLA4Ig forms were infused at a dose of 2 mg/kg via a Teflon angiocath which was placed in the marginal ear vein. Two control animals received an infusion of PBS (Ca$^{++}$ Mg$^{++}$free) in the same manner. Blood samples were drawn at 0, 15, 30, 60, 90, 360, 480 minutes, 24, 36, 48 hours, 7, 14 and 28 days. The concentration of free antibody in heparinized plasma was determined by a standard ELISA. Antibody clearance rates were determined. $\alpha$ and $\beta$ tl/2 values were calculated using the P-Fit subroutine of the BIOSOFT Fig-p figure processor/parameter fitter. The results are shown below:

hCTLA4IgG1
  $\alpha$ t1/2=4.2min
  $\beta$ t1/2=288 min
hCTLA4IgG4m
  $\alpha$ t1/2=16.6 min
  $\beta$ t 1/2=214.2min Both CTLA4IgG1 and CTLA4IgG4m have similar clearance rates, with a rapid (4–16 min) $\alpha$ phase and a more prolonged (214–288 min) $\beta$ phase indicating a serum half life of approximately 4 hours.

EXAMPLE 3

Preparation of *E, coli*-Expressed Human CTLA4

A. Intracellular Expression of CTLA4 in *E. coli*

1. Cloning and Expression of CTLA4 Extracellular Domain

The extracellular domain of CTLA4 was expressed in *E. coli* after cloning into expression vector pETCm11a. This vector was derived from expression vector pET-11a (Novagen Inc., Madison Wis.) by cloning a chloramphenicol resistance gene cassette into the ScaI restriction site within the ampicillin resistance gene. The extracellular domain of CTLA4 was prepared from plasmid phCTLA4 by PCR amplification using oligonucleotide 5'GCAGAGAGACAT ATGGCAATGCACGTGGCCCAGCCTGCTGTGG-3' (SEQ ID NO: 20) as forward primer and oligonucleotide 5'-GCAGAGAGAGGATCCTCAGTCAGTTAGTCAGAA TCTGGGCACGGTTCTGG-3' (SEQID NO: 21) as reverse primer. The forward PCR primer (SEQ ID NO: 20) contains an NdeI restriction site in which the ATG sequence in the NdeI restriction site is followed immediately by the codon for the first amino acid of mature CTLA4 (Dariavach, P., et al. (1988) *Eur. J. Immunol.* 18:1901). The reverse PCR primer (SEQ ID NO: 21) contains a BamHI restriction site preceded by translation stop codons in all three reading frames preceded by the last amino acid just prior to the CTLA4 transmembrane domain. PCR amplification with these primers yields a 416 bp fragment bounded by NdeI and BamHI restriction sites which contains DNA sequences encoding the extracellular domain of CTLA4 preceded by a methionine codon. The PCR product was digested with NdeI plus BamHI and ligated to expression vector pETCm11a digested with the same restriction enzymes.

The ligated DNA was transfected into *E. coli* strains BL2 1, HMS174, RGN714 and RGN715 containing the lambda DE3 helper phage by standard techniques. Transformants were selected in L-agar containing chloramphenicol at 50 ug/ml. Individual transformants were selected and tested for CTLA4 expression after induction by treatment of cells with 0.5 mM IPTG. Whole cell extracts were analyzed on SDS-PAGE gel followed by Coomassie Blue staining and Western blot analysis. The majority of the CTLA4 protein in these cells was found in inclusion bodies.

2. Purification of CTLA4 from Inclusion Bodies

Recombinant CTLA4 was recovered from cell pellets by treating the washed cells in lysis buffer (50 mM Tris-HCl pH 8.0, 1 mM PMSF, 5 mM EDTA, 0.5% Triton X-100, and lysozyme at 0.3 mg/ml) followed by sonication. The inclusion bodies were recovered by centrifugation at 20,000×g and solubilized by treatment with solubilization buffer (50 mM Tris-HCl pH8.0, 8 M urea, 50 mM 2-mercaptoethanol (2-ME)). The solubilization was assisted by mixing for two hours at room temperature. The soluble fraction contained CTLA4. The CTLA4 was purified by chromatography on S-sepharose (Pharmacia, Piscataway, N.J.) as follows. The CTLA4 containing supernatant was adjusted to pH 3.4 by the addition of glacial acetic and applied to a S-sepharose column equilibrated in column buffer (100 mM Na-acetate, pH6.5, 8 M urea, 50 mM 2-ME, and 5 mM EDTA). The column was washed with column buffer and the bound CTLA4 eluted with a linear salt gradient (NaCl, 0 to 1 M) prepared in column buffer. Peak fractions exhibiting high $Abs_{280nm}$ values were pooled and dialyzed against dialysis buffer (100 mM Tris-HCl, pH8.0, 8 M urea, 50 mM, 2-ME, 5 mM EDTA). Remaining contaminating proteins were eliminated by chromatography on a Sephacryl S-100 (Pharmacia, Piscataway, NJ) sizing column. The resulting preparation was greater than 95% pure CTLA4 as estimated by SDS-PAGE followed by Coomassie Blue staining and Western blot analysis. Since the estimated size of monomeric recombinant CTLA4 produced in *E. coli* was approximately 15 kDa, all steps of the purification protocol were tested for the presence of a 15 kDa protein by SDS-PAGE and the presence of CTLA4 verified by Western blotting.

3. Refolding of Denatured CTLA4

The CTLA4 protein purified from inclusion bodies is fully reduced and denatured and must be properly refolded in a physiological buffer, with intact disulfide bridges, to be in "active" form (i.e., able to bind hB7-1). To avoid solubility problems a step gradient dialysis procedure was used to remove urea, detergents and reductants. The most successful refolding was obtained when the secondary and tertiary protein structure was encouraged first, by gradient dialysis, removing all urea and detergent while in the presence of the reductant DTT. Subsequent slow removal of the DTT appeared to reduce the number of random intradisulfide bonds. As a control, a sample of CTLA4 was dialyzed directly from gel filtration buffer to PBS.

The success of refolding was estimated by immunoprecipitation. 5μg of hB7-1-Ig, bound to protein A resin, was used to pull down active CTLA4 from a 10 μg aliquot of each refolding trial. Precipitated protein was run on a reducing SDS-PAGE, transferred to an Immobilon membrane (Millipore, New Bedford, Mass.) and probed with polyclonal antisera to CTLA4 (antisera 1438, described in Lindsten, T. et al. (1993) *J. Immunol.* 151:3489–3499). The relative amount of protein detected at 15 kDa was indicative of the success of the refolding process. Refolding was also evaluated by assaying CTLA4 binding activity in a competition ELISA as described in Example 2. A successful refolding consisted of approximately 5% active protein, or about 2 mg of active protein from a 1 L bacterial culture.

B. Preparation of Secreted CTLA4 from *E. coli*

A secreted form of CTLA4 was prepared from *E. coli* as follows. The extracellular domain of CTLA4 was joined to the pelB signal sequence (Lei. S.-P., et al., (1987) *J. Bacteriol.* 169: 4379–4383) by PCR using plasmid phCTLA4 as template and oligonucleotide 5'GGCACTAGTCATGA AATACCTATTGCCTACGGCAGCCGCTGGATTGTTAT TACTCGCTGCCCAACCAGCGATGGCCGCAGCAAT GCACGTGGCCCAGCCTGCTGTGG3' (SEQ ID NO: 20) as the forward primer and a reverse primer (SEQ ID NO: 21) previously described. The forward PCR primer 5'-GGCACTAGTCATGAAATACCTATTGCCTACGGCA GCCGCTGGATTGTTATTACTCGCTGCCCAACCAGC GATGGCCGCAGCAATGCACGTGGCCCAGCCTGCTG TGG-3' (SEQ ID NO: 22) contains a unique BspHI restriction site, the complete pelB signal sequence and the 5' end of the extracellular domain of CTLA4. The reverse PCR primer (SEQ ID NO: 21) contains a unique BamH1 restriction site preceded by translational stop codons in all three reading frames preceded by the last amino acid before the transmembrane domain of CTLA4. PCR amplification with these primers yielded a 480 by fragment bounded by unique BspHI and BamHI restriction sites encoding the pelB signal sequence joined to the CTLA4 extracellular domain.

After PCR amplification, the DNA fragment was digested with BspHI and BamHI and ligated to expression vector pTrc99A (Pharmacia, Piscataway, N.J.) previously digested with NcoI and BamHI. This resulted in a plasmid in which the expression of the pelB-CTLA4 protein was driven by the pTrc promoter present in the pTrc99A expression vector. *E. coli* host strains transformed with the ligated DNA were selected on L-agar containing ampicillin (50 μg/ml) and individual clones isolated. The expression of CTLA4 in these strains was induced by the treatment of exponentially growing cultures with IPTG (0.5 mM) overnight. Extracts were prepared from the culture medium after concentration or by release from periplasm. To prepare periplasmic extracts, cells were incubated in 20% sucrose, 10 mM Tris-HCl pH7.5 for 15 minutes at room temperature, collected by centrifugation, and resuspended in 4° C. water and held on ice for 10 min. Extracts were assayed for the presence of CTLA4 by SDS-PAGE, Western blotting and competitive B7-1binding ELISA (as described in Example 2). As shown in FIG. 8, soluble CTLA4 prepared from periplasmic extracts of *E. coli* or from the media of these cultures was able to compete for binding to B7-1 with unlabelled CTLA4Ig. In contrast, periplasmic extracts from *E coli* transfected with the vector alone or media from these cultures was not able to compete for binding to B7-1.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A CTLA4-immunoglobulin fusion protein, comprising:
   a) a first peptide having at least one CTLA4 activity and a second peptide, wherein the second peptide comprises:
      i) an immunoglobulin constant region, wherein the immunoglobulin constant region comprises:
         1) the CH1 domain, hinge region, CH2 domain, and CH3 domain from a Cγ4 heavy chain; and
         2) a Leu to Glu substitution at position 235, and a Gly to Ala substitution at position 237 of the Cγ74 heavy chain.

* * * * *

UNITED STATES PATENT AND TRADEMARK OFFICE
CERTIFICATE OF CORRECTION

PATENT NO.    : 6,444,792 B1
DATED         : September 3, 2002
INVENTOR(S)   : Gary S. Gray et al.

It is certified that error appears in the above-identified patent and that said Letters Patent is hereby corrected as shown below:

Column 72,
Line 21, "...substitution at position 237 of the Cγ74 heavy chain." should read
-- ...substitution at position 237 of the Cγ4 heavy chain. --

Signed and Sealed this

Eleventh Day of February, 2003

JAMES E. ROGAN
*Director of the United States Patent and Trademark Office*